(12) United States Patent
Steinhagen et al.

(10) Patent No.: US 8,143,242 B2
(45) Date of Patent: Mar. 27, 2012

(54) MALONAMIDE DERIVATIVES WITH ANTITHROMBOTIC ACTIVITY

(75) Inventors: Henning Steinhagen, Frankfurt am Main (DE); Hauke Szillat, Frankfurt am Main (DE); Markus Follmann, Wülfrath (DE); Reinhard Kirsch, Frankfurt am Main (DE); Volkmar Wehner, Frankfurt am Main (DE); Hans Matter, Frankfurt am Main (DE); Martin Lorenz, Frankfurt am Main (DE); Kent W. Neuenschwander, Bridgewater, NJ (US); Anthony C. Scotese, Bridgewater, NJ (US)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/683,736

(22) Filed: Jan. 7, 2010

(65) Prior Publication Data
US 2010/0249101 A1 Sep. 30, 2010

Related U.S. Application Data

(63) Continuation of application No. PCT/EP2008/005187, filed on Jun. 26, 2008.

(30) Foreign Application Priority Data
Jul. 10, 2007 (EP) .................................. 07290877

(51) Int. Cl.
| | |
|---|---|
| A61K 31/553 | (2006.01) |
| A61K 31/4965 | (2006.01) |
| A61K 31/44 | (2006.01) |
| A61K 31/426 | (2006.01) |
| A61K 31/381 | (2006.01) |
| A61K 31/167 | (2006.01) |
| C07D 281/06 | (2006.01) |
| C07D 241/04 | (2006.01) |
| C07D 213/65 | (2006.01) |
| C07D 277/24 | (2006.01) |
| C07D 409/02 | (2006.01) |
| C07C 237/20 | (2006.01) |

(52) U.S. Cl. ............ 514/211.01; 514/255.02; 514/350; 514/365; 514/444; 514/616; 540/544; 544/383; 546/298; 548/205; 549/60; 564/157

(58) Field of Classification Search ............. 514/212.01, 514/350, 616, 357, 230.8, 460, 354, 351, 514/444, 424, 365, 255.02, 252.1; 546/298, 546/332, 245, 242; 564/157; 544/160, 383, 544/408; 549/416, 60; 548/543, 205; 540/544
See application file for complete search history.

(56) References Cited

U.S. PATENT DOCUMENTS
7,153,876 B2 * 12/2006 Schudok et al. .............. 514/345
2003/0162814 A1 8/2003 Juraszyk et al.

FOREIGN PATENT DOCUMENTS
| | | |
|---|---|---|
| DE | 10117823 A1 | 10/2002 |
| EP | 1193248 | 4/2002 |
| WO | WO 02/08177 | 1/2002 |

OTHER PUBLICATIONS

International Preliminary Report on Patentability related to DE2007/032; dated Jul. 15, 2009.

* cited by examiner

*Primary Examiner* — Kamal Saeed
*Assistant Examiner* — Kristin Bianchi
(74) *Attorney, Agent, or Firm* — Scully, Scott, Murphy & Presser, P.C.

(57) ABSTRACT

The present invention relates to compounds of formula I, (I)

The compounds of formula I are valuable pharmacologically active compounds. They exhibit a strong anti-thrombotic effect and are suitable, for example, for the therapy and prophylaxis of cardio-vascular disorders like thromboembolic diseases or restenoses. They are inhibitors of the blood clotting enzymes, especially factor VIIa and can in general be applied in conditions in which an undesired activity of factor VIIa is present or for the cure or prevention of which an inhibition of factor VIIa is intended. The invention furthermore relates to processes for the preparation of compounds of formula I, their use, in particular as active ingredients in pharmaceuticals, and pharmaceutical preparations comprising them.

10 Claims, No Drawings

MALONAMIDE DERIVATIVES WITH ANTITHROMBOTIC ACTIVITY

FIELD OF THE INVENTION

The present invention relates to compounds of the formula I,

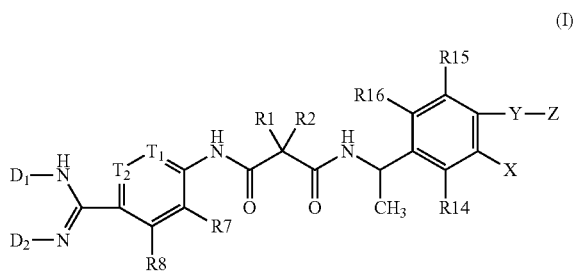

in which D1, D2, X and Y have the meanings indicated below. The compounds of the formula I are valuable pharmacologically active compounds. They exhibit a strong anti-thrombotic effect and are suitable, for example, for the therapy and prophylaxis of cardio-vascular disorders like thromboembolic diseases or restenoses. They are inhibitors of the blood clotting enzymes, especially factor VIIa and can in general be applied in conditions in which an undesired activity of factor VIIa is present or for the cure or prevention of which an inhibition of factor VIIa is intended. The invention furthermore relates to processes for the preparation of compounds of the formula I, their use, in particular as active ingredients in pharmaceuticals, and pharmaceutical preparations comprising them.

BACKGROUND OF THE INVENTION

Normal haemostasis is the result of a complex balance between the processes of clot initiation, formation and clot dissolution. The complex interactions between blood cells, specific plasma proteins and the vascular surface maintain the fluidity of blood unless injury and blood loss occurs (EP-A-987274). Many significant disease states are related to abnormal haemostasis. For example, local thrombus formation due to rupture of atherosclerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation. It is most desirable to develop agents that inhibit coagulation without directly inhibiting thrombin but by inhibiting other steps in the coagulation cascade like factor VIIa activity. Preclinical studies in baboons and dogs have shown that targeting enzymes involved at earlier stages of the coagulation cascade, such as factor Xa or factor VIIa, prevents clot formation without producing the bleeding side effects observed with direct thrombin inhibitors (L. A. Harker et al., Thromb. Hemostas. 74 (1995) 464). There is also experimental evidence suggesting that inhibition of factor VIIa/tissue factor activity inhibits restenosis following balloon angioplasty (L. A. Harker et al., Haemostasis 26 (1996) S1:76).

A specific inhibitor of factor VIIa which has a favourable property profile would have substantial practical value in the practice of medicine. In particular, a factor VIIa inhibitor would be effective under circumstances where the present drugs of choice, like heparin and related sulphated polysaccharides, are ineffective or only marginally effective.

Certain inhibitors of factor VIIa have already been described in WO02/28823, which disclose compounds inhibiting factor VIIa. However, the property profile of these compounds is still not ideal, and there is a need for further low molecular weight factor VIIa-specific blood clotting inhibitors especially with improved activity. The present inventions satisfy the above needs by providing novel compounds of the formulae I and Ia, which exhibit factor VIIa inhibitory activity and are favourable agents with better selectivity and high activity. Especially, the combination of the methyl residue between malonamide and phenyl residue in combination with X, Y and Z offers compounds with high selectivity and activity.

DESCRIPTION OF THE INVENTION

Thus, the present invention relates to compounds of the formula I,

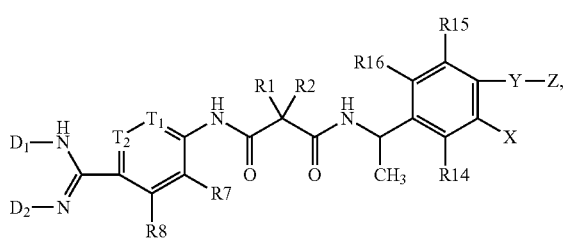

wherein

T1 and T2 independent from one another are selected from the group consisting of carbon atom, which is unsubstituted or substituted by R12, and nitrogen atom, D1 and D2 independently from one another are
1) hydrogen atom,
2) —C(O)—($C_1$-$C_6$)-alkyl,
3) —C(O)—($C_0$-$C_6$)-alkylene-aryl,
4) —C(O)—O—($C_1$-$C_6$)-alkyl or
5) —C(O)—O—($C_0$-$C_6$)-alkylene-aryl,
6) —C(O)—O—($C_1$-$C_6$)-alkylene-O—C(O)—($C_1$-$C_6$)-alkyl D1 is hydrogen atom, when D2 is
1) —OH,
2) —O—C(O)—($C_1$-$C_6$)-alkyl or
3) —O—C(O)—($C_0$-$C_6$)-alkylene-aryl,
4) —C(O)—O—($C_1$-$C_6$)-alkylene-O—C(O)—($C_1$-$C_6$)-alkyl R1 and R2 independent from one another are
1) hydrogen atom,
2) —OH or
3) —($C_0$-$C_6$)-alkylene-T-($C_0$-$C_6$)-alkylene-W,
wherein T is oxygen atom, sulfur atom, —$SO_2$— or —N(R17)-,
R17 is hydrogen atom or —($C_1$-$C_6$)-alkyl, wherein alkyl is unsubstituted or mono-,
di-, tri- or tetra-substituted independently of one another by R13,
W is hydrogen atom or aryl, wherein aryl is unsubstituted or mono-, di-, tri- or tetra-substituted independently of one another by R13, R7, R8, R12, R14, R15 and R16 independent from one another are
1) hydrogen atom,
2) —$(C_1\text{-}C_6)$-alkyl,
3) —OH,
4) —O—$(C_1\text{-}C_6)$-alkyl,
5) halogen or
6) —$NH_2$, X is 1) halogen,
2) —$(C_1\text{-}C_3)$-perfluoroalkyl,
3) —O—$(C_1\text{-}C_3)$-perfluoroalkyl,
4) —$S(O)_n$—$(C_1\text{-}C_3)$-perfluoroalkyl, wherein n is the integer 1 or 2,
5) —$(C_0\text{-}C_4)$-alkylene-aryl, wherein aryl is unsubstituted or mono-, di-, tri- or tetra-substituted independently of one another by R13,
wherein R13 is halogen, —$(C_1\text{-}C_3)$-perfluoroalkyl, —$(C_1\text{-}C_4)$-alkyl,
—$(C_0\text{-}C_6)$-alkylene-O—R6, —$(C_0\text{-}C_6)$-alkylene-C(O)—R6, —$(C_0\text{-}C_6)$-alkylene-C(O)—O—R6, —O—$(C_1\text{-}C_3)$-perfluoroalkyl, —$S(O)_r$—$(C_1\text{-}C_4)$-alkyl, wherein r is the integer 1 or 2 or —$(C_0\text{-}C_4)$-alkylene-$(C_3\text{-}C_7)$-cycloalkyl,
wherein R6 is hydrogen atom or —$(C_1\text{-}C_6)$-alkyl,
6) —$(C_0\text{-}C_4)$-alkylene-Het, wherein Het is a heterocycle consisting of 1, 2 or 3 rings, in which one or more of the 4 to 15 ring carbon atoms are replaced by at least 1 heteroatom selected out of the group nitrogen, oxygen or sulfur and wherein Het is unsubstituted or mono-, di-, tri- or tetra-substituted independently of one another by R5, wherein R5 is —$(C_1\text{-}C_4)$-alkyl, halogen, =O, —$(C_0\text{-}C_6)$-alkylene-O—R6, —$(C_0\text{-}C_6)$-alkylene-C(O)—R6,
—$(C_0\text{-}C_6)$-alkylene-C(O)—O—R6, —$(C_0\text{-}C_4)$-alkylene-$(C_3\text{-}C_7)$-cycloalkyl, or
—$(C_0\text{-}C_4)$-alkylene-aryl, wherein aryl is unsubstituted or mono-, di-, tri- or tetra-substituted independently of one another by R13, or
7) hydrogen atom, Y is 1) —N(R4)-, wherein R4 is hydrogen atom or —$(C_1\text{-}C_6)$-alkyl,
2) —C(O)—,
3) —C(O)—N(R4)-,
4) —N(R4)-C(O)—,
5) —O—,
6) —$S(O)_n$—, wherein n is the integer zero, 1 or 2, or
7) —$S(O)_m$—N(R4)-, wherein m is the integer zero, 1 or 2, Z is 1) —$(C_0\text{-}C_4)$-alkylene-Het, wherein Het is unsubstituted or mono-, di-, tri- or tetra-substituted independently of one another by R5,
2) —$(C_1\text{-}C_6)$-alkylene-C(O)—O—R6,
3) —$(C_1\text{-}C_6)$-alkylene-O—R9,
wherein R9 is hydrogen atom or —$(C_1\text{-}C_6)$-alkyl,
4) —$(C_1\text{-}C_6)$-alkylene-N(R10)-R11,
wherein R10 and R11 independently from one another are hydrogen atom, —$(C_0\text{-}C_4)$-alkylene-C(O)—R6, -$(C_0\text{-}C_4)$-alkylene-O—R6 or -$(C_1\text{-}C_6)$-alkyl,
5) —$(C_0\text{-}C_4)$-alkylene-C(O)—R6,
6) —$(C_2\text{-}C_6)$-alkynyl,
7) —$(C_1\text{-}C_3)$-perfluoroalkyl,
8) —$(C_0\text{-}C_4)$-alkylene-$(C_3\text{-}C_7)$-cycloalkyl-R5,
9) —$(C_1\text{-}C_4)$-alkylene-aryl, wherein aryl is unsubstituted or mono-, di-, tri- or tetra-substituted independently of one another by R13,
10) phenyl, wherein phenyl is mono-, di-, tri- or tetra-substituted independently of one another by —$(C_0\text{-}C_4)$-alkylene-$(C_3\text{-}C_7)$-cycloalkyl, =O, —$(C_0\text{-}C_6)$-alkylene-C(O)—O—R6, —$(C_1\text{-}C_6)$-alkylene-O—R6 or —$S(O)_s$—$(C_1\text{-}C_3)$-alkyl, wherein s is the integer zero, 1 or 2,
11) —$S(O)_r$—$(C_1\text{-}C_3)$-alkyl, wherein r is the integer zero, 1 or 2, provided Y is —N(R4)-, or
12) —$(C_1\text{-}C_3)$-perfluoroalkyl, or Y and Z together are hydrogen atom and X is
1) —$(C_1\text{-}C_3)$-alkyl-CN,
2) —$(C_1\text{-}C_3)$-perfluoroalkyl,
3) —O—$(C_1\text{-}C_3)$—,
4) —$S(O)_m$—$(C_1\text{-}C_3)$-perfluoroalkyl, wherein m is the integer 1 or 2,
5) —$(C_0\text{-}C_4)$-alkylene-Het, wherein Het is mono-, di-, tri- or tetra-substituted independently of one another by aryl, or
6) phenyl substituted by —N(R3)-$S(O)_p$, wherein R3 is hydrogen atom or —$(C_1\text{-}C_6)$-alkyl and p is the integer 1 or 2, in all its stereoisomeric forms and mixtures thereof in any ratio, and its physiologically tolerable salts.

2) The present invention also relates to the compounds of the formula Ia,

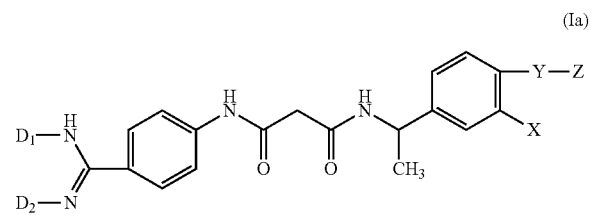

(Ia)

wherein
D1 and D2 are each hydrogen atom,
X is 1) halogen, selected out of the group fluorine, chlorine, bromine and iodine,
2) —$(C_1\text{-}C_3)$-perfluoroalkyl,
3) —O—$(C_1\text{-}C_3)$-perfluoroalkyl,
4) —$S(O)_n$—$(C_1\text{-}C_3)$-perfluoroalkyl, wherein n is the integer 1 or 2,
5) —$(C_0\text{-}C_4)$-alkylene-aryl, wherein aryl is selected out of the group phenyl, naphthyl, biphenylyl, anthryl or fluorenyl unsubstituted or mono-, di-, tri- or tetra-substituted independently of one another by R13,
wherein R13 is halogen, —$(C_1\text{-}C_3)$-perfluoroalkyl, —$(C_1\text{-}C_4)$-alkyl, —$(C_0\text{-}C_6)$-alkylene-O—R6, —$(C_0\text{-}C_6)$-alkylene-C(O)—R6, —$(C_0\text{-}C_6)$-alkylene-C(O)—O—R6, —O—$(C_1\text{-}C_3)$-perfluoroalkyl, —$S(O)_r$—$(C_1\text{-}C_4)$-alkyl, wherein r is the integer 1 or 2 or —$(C_0\text{-}C_4)$-alkylene-$(C_3\text{-}C_7)$-cycloalkyl,
wherein R6 is hydrogen atom or —$(C_1\text{-}C_6)$-alkyl,
6) —$(C_0\text{-}C_4)$-alkylene-Het, wherein Het is selected out of the group acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl and wherein Het is unsubstituted or mono-, di-, tri- or tetra-substituted independently of one another by R5, wherein R5 is —($C_1$-$C_4$)-alkyl, halogen, =O, —($C_0$-$C_6$)-alkylene-O—R6, —($C_0$-$C_6$)-alkylene-C(O)-R6, —($C_0$-$C_6$)-alkylene-C(O)—O—R6, —($C_0$-$C_4$)-alkylene-($C_3$-$C_7$)-cycloalkyl, or —($C_0$-$C_4$)-alkylene-aryl, wherein aryl is unsubstituted or mono-, di-, tri- or tetra-substituted independently of one another by R13, or 7) hydrogen atom, Y is 1) —N(R4)-, wherein R4 is hydrogen atom or —($C_1$-$C_6$)-alkyl,
2) —C(O)—,
3) —C(O)—N(R4)-,
4) —N(R4)-C(O)—,
5) —O—,
6) —S(O)$_n$—, wherein n is the integer zero, 1 or 2, or
7) —S(O)$_m$—N(R4)-, wherein m is the integer zero, 1 or 2, Z is 1) —($C_0$-$C_4$)-alkylene-Het, wherein Het is unsubstituted or mono-, di-, tri- or tetra-substituted independently of one another by R5,
2) —($C_1$-$C_6$)-alkylene-C(O)—O—R6,
3) —($C_1$-$C_6$)-alkylene-O—R9,
wherein R9 is hydrogen atom or —($C_1$-$C_6$)-alkyl,
4) —($C_1$-$C_6$)-alkylene-N(R10)-R11,
wherein R10 and R11 independently from one another are hydrogen atom, —($C_0$-$C_4$)-alkylene-C(O)—R6, —($C_0$-$C_4$)-alkylene-O—R6 or —($C_1$-$C_6$)-alkyl,
5) —($C_0$-$C_4$)-alkylene-C(O)—R6,
6) —($C_2$-$C_6$)-alkynyl,
7) —($C_1$-$C_3$)-perfluoroalkyl,
8) —($C_0$-$C_4$)-alkylene-($C_3$-$C_7$)-cycloalkyl-R5,
9) —($C_1$-$C_4$)-alkylene-aryl, wherein aryl is as defined above and is unsubstituted or mono-, di-, tri- or tetra-substituted independently of one another by R13,
10) phenyl, wherein phenyl is mono-, di-, tri- or tetra-substituted independently of one another by —($C_0$-$C_4$)-alkylene-($C_3$-$C_7$)-cycloalkyl, =O, —($C_0$-$C_6$)-alkylene-C(O)—O—R6, —($C_1$-$C_6$)-alkylene-O—R6 or —S(O)$_s$—($C_1$-$C_3$)-alkyl, wherein s is the integer zero, 1 or 2,
11) —S(O)$_r$—($C_1$-$C_3$)-alkyl, wherein r is the integer zero, 1 or 2, provided Y is —N(R4)-, or
12) —($C_1$-$C_3$)-perfluoroalkyl, or Y and Z together are hydrogen atom and X is
1) —($C_1$-$C_3$)-alkyl-CN,
2) —($C_1$-$C_3$)-perfluoroalkyl,
3) —O—($C_1$-$C_3$)-perfluoroalkyl,
4) —S(O)$_m$—($C_1$-$C_3$)-perfluoroalkyl, wherein m is the integer 1 or 2,
5) —($C_0$-$C_4$)-alkylene-Het, wherein Het is mono-, di-, tri- or tetra-substituted independently of one another by aryl, wherein aryl is selected out of the group phenyl, naphthyl, biphenylyl, anthryl or fluorenyl, or
6) phenyl substituted by —N(R3)-S(O)$_p$-, wherein R3 is hydrogen atom or —($C_1$-$C_6$)-alkyl and p is the integer 1 or 2, in all its stereoisomeric forms and mixtures thereof in any ratio, and its physiologically tolerable salts.

3) The present invention also relates to the compounds of the formula Ia, wherein D1 and D2 are each hydrogen atom, X is 1) chlorine, bromine or fluorine,
2) —($C_1$-$C_3$)-perfluoroalkyl,
3) —O—($C_1$-$C_3$)-perfluoroalkyl,
4) —S(O)$_n$—($C_1$-$C_3$)-perfluoroalkyl, wherein n is the integer 1 or 2,
5) —($C_0$-$C_4$)-alkylene-phenyl, wherein phenyl is unsubstituted or mono-, di-, tri- or tetra-substituted independently of one another by R13,
wherein R13 is chlorine, bromine, fluorine, —($C_1$-$C_3$)-perfluoroalkyl, —($C_1$-$C_4$)-alkyl, —($C_0$-$C_6$)-alkylene-O—R6, —($C_0$-$C_6$)-alkylene-C(O)—R6, —($C_0$-$C_6$)-alkylene-C(O)—O—R6, —O—($C_1$-$C_3$)-perfluoroalkyl, —S(O)$_r$—($C_1$-$C_4$)-alkyl,
wherein r is the integer 1 or 2 or —($C_0$-$C_4$)-alkylene-($C_3$-$C_7$)-cycloalkyl,
wherein R6 is hydrogen atom or —($C_1$-$C_4$)-alkyl,
6) —($C_0$-$C_4$)-alkylene-Het, wherein Het is selected out of the group acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydro-furanyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl and wherein Het is unsubstituted or mono-, di-, tri- or tetra-substituted independently of one another by R5, wherein R5 is —$(C_1$-$C_4)$-alkyl, chlorine, bromine, fluorine, =O, —$(C_0$-$C_6)$-alkylene-O—R6, —$(C_0$-$C_6)$-alkylene-C(O)—R6, —$(C_0$-$C_6)$-alkylene-C(O)—O—R6, —$(C_0$-$C_4)$-alkylene-$(C_3$-$C_7)$-cycloalkyl, or —$(C_0$-$C_4)$-alkylene-phenyl, wherein phenyl is unsubstituted or mono-, di-, tri- or tetra-substituted independently of one another by R13, Y is 1) —N(R4)-, wherein R4 is hydrogen atom or —$(C_1$-$C_4)$-alkyl,
2) —C(O)—,
3) —C(O)—N(R4)-,
4) —N(R4)-C(O)—,
5) —O—,
6) —S(O)$_n$—, wherein n is the integer zero, 1 or 2, or
7) —S(O)$_m$—N(R4)-, wherein m is the integer zero, 1 or 2, Z is 1) —$(C_0$-$C_4)$-alkylene-Het, wherein Het is as defined above and wherein Het is unsubstituted or mono-, di-, tri- or tetra-substituted independently of one another by R5,
2) —$(C_1$-$C_6)$-alkylene-C(O)—O—R6,
3) —$(C_1$-$C_6)$-alkylene-O—R9,
   wherein R9 is hydrogen atom or —$(C_1$-$C_6)$-alkyl,
4) —$(C_1$-$C_6)$-alkylene-N(R10)-R11,
   wherein R10 and R11 independently from one another are hydrogen atom, —$(C_0$-$C_4)$-alkylene-C(O)—R6, —$(C_0$-$C_4)$-alkylene-O—R6 or —$(C_1$-$C_6)$-alkyl,
5) —$(C_0$-$C_4)$-alkylene-C(O)—R6,
6) —$(C_0$-$C_4)$-alkylene-$(C_3$-$C_7)$-cycloalkyl-R5, or
7) —$(C_0$-$C_4)$-alkylene-aryl, wherein aryl is selected out of the group phenyl, naphthyl, biphenylyl, anthryl or fluorenyl and wherein aryl is mono-, di-, tri- or tetra-substituted independently of one another by R13,
   wherein R13 is —$(C_0$-$C_4)$-alkylene-$(C_3$-$C_7)$-cycloalkyl, =O, —$(C_1$-$C_6)$-alkylene-C(O)—O—R6 or —$(C_1$-$C_4)$-alkylene-O—R6, in all its stereoisomeric forms and mixtures thereof in any ratio, and its physiologically tolerable salts.

4) The present invention also relates to the compounds of the formula Ia, wherein D1 and D2 are each hydrogen atom,
X is 1) chlorine, bromine or fluorine,
2) —CF$_3$,
3) —O—CF$_3$,
4) —O—CH$_2$—CHF$_2$,
5) —O—CH$_2$—CH$_2$—CH$_2$F,
6) —O—CH$_2$—CF$_3$,
7) phenyl, wherein phenyl is unsubstituted or mono- or di-substituted independently of one another by R13,
   wherein R13 is chlorine, bromine, fluorine, —O—$(C_1$-$C_3)$-perfluoroalkyl, —O—R6, —C(O)—O—R6 or —S(O)$_2$—$(C_1$-$C_2)$-alkyl
   wherein R6 is hydrogen atom or —$(C_1$-$C_4)$-alkyl, or
8) Het$_1$, wherein Het$_1$ is selected out of the group pyridine, pyrimidine, thiazole or thienyl, wherein Het is unsubstituted or substituted by chlorine, bromine, fluorine or —C(O)—O—R6, Y is 1) —N(R4)-, wherein R4 is hydrogen atom or methyl,
2) —C(O)—,
3) —C(O)—N(R4)-,
4) —NH—C(O)—,
5) —O—,
6) —S(O)—,
7) —S(O)$_2$—, or
8) —S(O)$_2$—N(R4)-, Z is 1) —$(C_0$-$C_3)$-alkylene-Het, wherein Het is selected out of the group 1,3-dioxolanyl, furanyl, morpholinyl, [1,4]-oxazepanyl, oxetanyl, piperazinyl, piperidinyl, pyrazinyl, pyridyl, pyrimidinyl, pyrrolidinyl, tetrahydrofuranyl, tetrahydropyranyl, thiazolyl, thienyl and wherein Het is unsubstituted or mono-, di- or tri-substituted independently of one another by R5,
   wherein R5 is hydrogen atom, —$(C_1$-$C_2)$-alkyl, -cyclopropyl, =O, phenyl, fluorine, —$(C_0$-$C_2)$-alkylene-C(O)—O—R6, —O—R6, C(O)—R6, or —$(C_1$-$C_2)$-alkylene-O—R6,
   wherein R6 is hydrogen atom or —$(C_1$-$C_4)$-alkyl,
2) —$(C_1$-$C_6)$-alkylene-C(O)—O—R6,
3) —$(C_1$-$C_6)$-alkylene-O—R9,
   wherein R9 is hydrogen atom or —$(C_1$-$C_3)$-alkyl,
4) —$(C_1$-$C_4)$-alkylene-N(R10)-R11,
   wherein R10 and R11 independently from one another are hydrogen atom, —$(C_0$-$C_4)$-alkylene-O—R6 or —$(C_1$-$C_2)$-alkyl,
5) —$(C_0$-$C_2)$-alkylene-C(O)—R6, or
6) —$(C_0$-$C_2)$-alkylene-cyclohexyl-R5, in all its stereoisomeric forms and mixtures thereof in any ratio, and its physiologically tolerable salts.

5) The present invention also relates to the compounds of the formula Ia, wherein D1 and D2 are each hydrogen atom,
X is 1) chlorine, bromine or fluorine,
2) —CF$_3$,
3) —O—CF$_3$,
4) —O—CH$_2$—CHF$_2$,
5) —O—CH$_2$—CH$_2$—CH$_2$F,
6) —O—CH$_2$—CF$_3$,
7) phenyl, wherein phenyl is unsubstituted or mono- or di-substituted independently of one another by R13,
   wherein R13 is chlorine, bromine, fluorine, —O—$(C_1$-$C_3)$-perfluoroalkyl, —O—R6, —C(O)—O—R6 or —S(O)$_2$—$(C_1$-$C_2)$-alkyl
   wherein R6 is hydrogen atom or —$(C_1$-$C_4)$-alkyl, or
8) Het$_1$, wherein Het$_1$ is selected out of the group pyridine, pyrimidine, thiazole or thienyl, wherein Het is unsubstituted or substituted by chlorine, bromine, fluorine or —C(O)—O—R6, Y is —O—,
Z is 1) —$(C_0$-$C_3)$-alkylene-Het, wherein Het is selected out of the group 1,3-dioxolanyl, furanyl, morpholinyl, [1,4]-oxazepanyl, oxetanyl, piperazinyl, piperidinyl, pyrazinyl, pyridyl, pyrimidinyl, pyrrolidinyl, tetrahydrofuranyl, tetrahydropyranyl, thiazolyl, thienyl and wherein Het is unsubstituted or mono-, di- or tri-substituted independently of one another by R5,
   wherein R5 is hydrogen atom, —$(C_1$-$C_2)$-alkyl, -cyclopropyl, =O, phenyl, fluorine, —$(C_0$-$C_2)$-alkylene-C(O)—O—R6, —O—R6, C(O)—R6 or —$(C_1$-$C_2)$-alkylene-O—R6,
   wherein R6 is hydrogen atom or —$(C_1$-$C_4)$-alkyl, 2) —(C$_1$-C$_6$)-alkylene-C(O)—O—R6,
3) —(C$_1$-C$_6$)-alkylene-O—R9,
   wherein R9 is hydrogen atom or —(C$_1$-C$_3$)-alkyl,
4) —(C$_1$-C$_4$)-alkylene-N(R10)-R11,
   wherein R10 and R11 independently from one another are hydrogen atom, —(C$_0$-C$_4$)-alkylene-O—R6 or —(C$_1$-C$_2$)-alkyl,
5) —(C$_0$-C$_2$)-alkylene-C(O)—R6, or 6) —(C$_0$-C$_2$)-alkylene-cyclohexyl-R5, in all its stereoisomeric forms and mixtures thereof in any ratio, and its physiologically tolerable salts.

6) The present invention also relates to the compounds of the formula Ia, wherein D1 and D2 are each hydrogen atom,
X is 1) chlorine, bromine or fluorine,
   2) —CF$_3$,
   3) —O—CF$_3$,
   4) —O—CH$_2$—CHF$_2$,
   5) —O—CH$_2$—CH$_2$—CH$_2$F,
   6) —O—CH$_2$—CF$_3$,
   7) phenyl, wherein phenyl is unsubstituted or mono- or di-substituted independently of one another by R13,
      wherein R13 is chlorine, bromine, fluorine, —O—(C$_1$-C$_3$)-perfluoroalkyl, —O—R6, —C(O)—O—R6 or —S(O)$_2$—(C$_1$-C$_2$)-alkyl,
      wherein R6 is hydrogen atom or —(C$_1$-C$_4$)-alkyl, or
   8) Het$_1$, wherein Het$_1$ is selected out of the group pyridine, pyrimidine, thiazole or thienyl, wherein Het is unsubstituted or substituted by chlorine, bromine, fluorine or —C(O)—O—R6,
Y is —S(O)$_2$—,
Z is 1) —(C$_0$-C$_3$)-alkylene-Het, wherein Het is selected out of the group 1,3-dioxolanyl, furanyl, morpholinyl, [1,4]-oxazepanyl, oxetanyl, piperazinyl, piperidinyl, pyrazinyl, pyridyl, pyrimidinyl, pyrrolidinyl, tetrahydrofuranyl, tetrahydropyranyl, thiazolyl, thienyl and wherein Het is unsubstituted or mono-, di- or tri-substituted independently of one another by R5,
   wherein R5 is hydrogen atom, —(C$_1$-C$_2$)-alkyl, -cyclopropyl, =O, phenyl, fluorine, —(C$_0$-C$_2$)-alkylene-C(O)—O—R6, —O—R6, C(O)—R6, or —(C$_1$-C$_2$)-alkylene-O—R6,
   wherein R6 is hydrogen atom or —(C$_1$-C$_4$)-alkyl,
2) —(C$_1$-C$_6$)-alkylene-C(O)—O—R6,
3) —(C$_1$-C$_6$)-alkylene-O—R9,
   wherein R9 is hydrogen atom or —(C$_1$-C$_3$)-alkyl,
4) —(C$_1$-C$_4$)-alkylene-N(R10)-R11,
   wherein R10 and R11 independently from one another are hydrogen atom, —(C$_0$-C$_4$)-alkylene-O—R6 or —(C$_1$-C$_2$)-alkyl,
5) —(C$_0$-C$_2$)-alkylene-C(O)—R6, or
6) —(C$_0$-C$_2$)-alkylene-cyclohexyl-R5, in all its stereoisomeric forms and mixtures thereof in any ratio, and its physiologically tolerable salts.

7) The present invention also relates to the compounds of the formula Ia, wherein D1 and D2 are each hydrogen atom,
Y and Z together are hydrogen atom,
X is 1) —(C$_1$-C$_3$)-alkyl-CN,
   2) —CF$_2$—CF$_3$,
   3) —O—CF$_2$—CHF$_2$,
   4) —O—CH$_2$—CF$_3$,
   5) —S(O)—CF$_3$,
   6) —S(O)$_2$—CF$_3$,
   7) imidazolyl, substituted by phenyl, or
   8) phenyl substituted by —NH—S(O)$_2$-methyl.

in all its stereoisomeric forms and mixtures thereof in any ratio, and its physiologically tolerable salts.

8) The present invention also relates to the compounds of the formula Ia, wherein D1 and D2 are each hydrogen atom,
X is hydrogen atom,
Y is 1) —NH—,
   2) —NH—C(O)— or
   3) —S(O)$_2$—,
Z is 1) Het, wherein Het is selected out of the group morholinyl and piperidinyl, or
   2) —S(O)$_2$-methyl, provided Y is —NH—, in all its stereoisomeric forms and mixtures thereof in any ratio, and its physiologically tolerable salts.

As used herein, the term alkyl is to be understood to mean hydrocarbon residues, which have a straight chain or are branched. Examples for "—(C$_1$-C$_6$)-alkyl" are hydrocarbon residues containing 1, 2, 3, 4, 5 or 6 carbon atoms e.g. methyl, ethyl, propyl, isobutyl, butyl, isobutyl, secundary-butyl, tertiary-butyl, pentyl, isopentyl, neopentyl, 1-ethylpropyl, hexyl, 2,3-dimethylbutyl or neohexyl. Examples for "—(C$_1$-C$_6$)-alkylene" are hydrocarbon residues containing 1, 2, 3, 4, 5 or 6 carbon atoms with two covalent bonds such as methylene, ethylene, propylene, butylene, pentylene or hexylene.

The term "—C$_0$-alkyl" or "—C$_0$-alkylene" is each a covalent bond.

The term "—(C$_2$-C$_6$)-alkynyl" refers to alkyl residues containing 2, 3, 4, 5 or 6 carbon atoms and 1 or 2 triple bonds, for example alkynyl residues such as ethynyl, 1-propynyl, 2-propynyl (=propargyl) or 2-butynyl.

Examples of -(C$_3$-C$_7$)-cycloalkyl are cycloalkyl residues containing 3, 4, 5, 6 or 7 ring carbon atoms like cyclopropyl, cyclobutyl, cyclopentyl, cyclohexyl or cyloheptyl.

Examples of —(C$_3$-C$_7$)-cycloalkyl, which are partially unsaturated, are groups such as cyclopentenyl or cyclohexenyl, which can be bonded via any carbon atom.

The term "aryl" is understood as meaning aromatic hydrocarbon radicals containing from 6 to 14 carbon atoms in the ring. Examples of aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The term "halogen" is fluorine, chlorine, bromine or iodine, preferably fluorine, chlorine or bromine.

The term "-Het" refers to a heterocycle consisting of 1, 2 or 3 rings, in which one or more of the 4 to 15 ring carbon atoms are replaced by at least 1 heteroatom selected out of the group nitrogen, oxygen or sulfur. Examples are acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The terms "oxo-residue" or "=O" refer to residues such as carbonyl (—C(O)—) or nitroso (—N=O).

The term "—($C_1$-$C_3$)-perfluoroalkyl" is a partial or totally fluorinated alkyl-residue, which can be derived from residues such as —$CF_3$, —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF-$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The fact that many of the before-listed names of heterocycles are the chemical names of unsaturated or aromatic ring systems does not imply that the Het groups could only be derived from the respective unsaturated ring system. The names here only serve to describe the ring system with respect to ring size and the number of the heteroatoms and their relative positions. As explained above, for example a Het group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which a Het group and any other heterocyclic group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), 2,3-dihydrobenzo[1,4]dioxine, 3,4-dihydro-2H-benzo[1,4]oxazine, perhydro-1,4-thiazine (=thiomorpholine), perhydroazepine, indoline, isoindoline, 1,2,3,4-tetrahydro-quinoline or 1,2,3,4-tetrahydroisoquinoline.

Optically active carbon atoms present in the compounds of the formulae I and Ia can independently of each other have R configuration or S configuration. The compounds of the formulae I and Ia can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or more stereoisomers of the formulae I and Ia, and it comprises all ratios of the stereoisomers in the mixtures. In case the compounds of the formulae I and Ia can be present as E isomers or Z isomers (or cis isomers or trans isomers) the invention relates both to pure E isomers and pure Z isomers and to E/Z mixtures in all ratios. The invention also comprises all tautomeric forms of the compounds of the formulae I and Ia.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formulae I and Ia can also be obtained by employing stereochemically uniform starting materials or by using stereoselective reactions.

Physiologically tolerable salts of the compounds of formulae I and Ia are nontoxic salts that are physiologically acceptable, in particular pharmaceutically utilizable salts. Such salts of compounds of the formulae I and Ia containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethyl-ammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)-amine. Basic groups contained in the compounds of the formulae I and Ia, for example amino groups or amidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. The present invention also includes acid addition salts of compounds of the formulae I and Ia, which contain, for example, two basic groups, with one or two acid equivalents.

Salts of compounds of the formulae I and Ia can be obtained by customary methods known to those skilled in the art, for example by combining a compound of the formulae I and Ia with an inorganic or organic acid or base in a solvent or diluent, or from other salts by cation exchange or anion exchange. The present invention also includes all salts of the compounds of the formulae I and Ia which, because of low physiological tolerability, are not directly suitable for use in pharmaceuticals but are suitable, for example, as intermediates for carrying out further chemical modifications of the compounds of the formulae I and Ia or as starting materials for the preparation of physiologically tolerable salts.

The anions of the mentioned acids that may be present in acid addition salts of the compounds of the formulae I and Ia, are also examples of anions that may be present in the compounds of the formulae I and Ia if they contain one or more positively charged groups like trialkylammonio-substituents, e.g. groups of the formula $(alkyl)_3N^+$ bonded via the positively charged nitrogen atom, or quaternized ring nitrogen atoms in heterocyclic groups. In general a compound of the formulae I and Ia contains one or more physiologically tolerable anions or anion equivalents as counter ions, if it contains one or more permanently positively charged groups like trialkylammonio. Compounds of the formulae I and Ia, which simultaneously contain a basic group or a positively charged group and an acidic group, for example an amidino group and a carboxy group, can also be present as zwitterions (betaines) which are likewise included in the present invention.

The present invention also relates to processes of preparation by which the compounds of the formulae I and Ia are obtainable. The compounds of the formulae I and Ia can generally be prepared by coupling of two or more fragments (or building blocks), which can be derived retrosynthetically from formulae I and Ia. In the preparation of the compounds of the formulae I and Ia it can generally be advantageous or necessary in the course of the synthesis to introduce functional groups, which could lead to undesired reactions or side reactions in a synthesis step, in the form of precursors which are later converted into the desired functional groups. As examples of precursor groups cyano groups may be mentioned which may later be converted into amidino groups, or nitro groups, which may be converted into amino groups. Protecting groups (or blocking groups) that may be present on functional groups include allyl, tert.-butyl, benzyl, allyloxycarbonyl (Alloc), tert-butoxycarbonyl (Boc), benzyloxycarbonyl (Z) and 9-fluorenylmethoxycarbonyl (Fmoc) as protecting groups for amino and amidino groups. Ester, alkyl, aryl and silyl protecting groups may be used to block hydroxyl groups. Carboxylic acids may be protected as esters for example methyl, ethyl and benzyl.

In particular, in the preparation of the compounds of the formulae I and Ia building blocks can be connected by performing one or more condensation reactions and/or addition reactions such as amide couplings, e.g. by forming an amide bond between a carboxylic acid group of one building block and an amino group of another building block. For example, compounds of the formulae I and Ia can be prepared by coupling

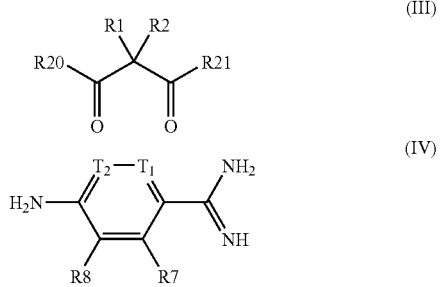

(III)

(IV)

of building blocks of the formulae III, IV, and V,

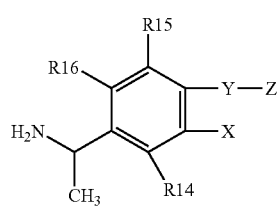

(V)

wherein R20 and R21 are independently from each other —OH, F, Cl or together with the carbonyl group form an ester, or an activated ester, or a mixed anhydride, or any other activated species resulting from the reaction of the carboxylic acid with coupling reagents, and X, Y and Z are as defined for formulae I and Ia, by means of forming, in a manner known per se, an amide bond between the carboxylic acid derivative depicted in formula III and the $NH_2$-group depicted in formula IV and an amide bond or ester bond between the carboxylic acid derivative depicted in formula III and the $NH_2$-group depicted in formula V.

The starting compounds of the formulae III, IV and V, and other compounds which are employed in the synthesis of the compounds of formulae I and Ia for introducing certain structural units, are commercially available or can be readily prepared from commercially available compounds or by analogously procedures described below or in the literature which is readily available to those skilled in the art.

For the preparation of the compounds of formulae I and Ia the compounds of the formulae III and IV may be linked first and the resulting intermediate product may then be condensed with a compound of the formula V to give a compound of the formulae I and Ia. Alternatively, the compounds of the formulae III and V may be condensed first and the resulting intermediate product may then be linked to a compound of the formula IV to give a compound of the formulae I and Ia. After any such reaction step in the course of such syntheses protecting and deprotecting steps and conversions of precursor groups into the desired final groups may be carried out and further modifications may be made.

Various general methods for the formation of an amide bond that can be employed in the synthesis of the compounds of formulae I and Ia are just so well known to those skilled in the art, for example from peptide chemistry. An amide coupling step can favorably be carried out by employing a free carboxylic acid, e. g. a compound of the formula III, activating that carboxylic acid group, preferably in situ, by means of a customary coupling reagent such as a carbodiimide like dicyclohexylcarbodiimide (DCC) or diisopropylcarbodiimide (DIC), or an N,N'-carbonyldiazole like N,N'-carbonyldiimidazole, or a uronium salt like O-((cyano(ethoxycarbonyl)methylene)-amino)-1,1,3,3-tetramethyluronium tetrafluoroborate (TOTU) or O-(7-azabenzotriazol-1-yl)-1,1,3,3-tetramethyluronium hexafluorophosphate (HATU), or a chloroformic acid ester like ethyl chloroformate or isobutyl chloroformate, or tosyl chloride, or propylphosphonic acid anhydride, or others, and then reacting the activated carboxylic acid derivative with an amino compound of the formula IV. An amide bond can also be formed by reacting an amino compound with a carboxylic acid halide, in particular a carboxylic acid chloride, which can be prepared in a separate step or in situ from a carboxylic acid and, for example, thionyl chloride, or an carboxylic acid ester or thioester, for example a methyl ester, ethyl ester, phenyl ester, nitrophenyl ester, pentafluorophenyl ester, methylthio ester, phenylthio ester or pyridin-2-ylthio ester, i. e. with a compound of the formula III.

The activation reactions and coupling reactions are usually performed in the presence of an inert solvent (or diluent), for example in the presence of an aprotic solvent like dimethylformamide (DMF), tetrahydrofuran (THF), dichloromethane (DCM), dimethylsulfoxide (DMSO), hexamethyl phosphoric triamide (HMPT), 1,2-dimethoxyethane (DME), dioxane, or others, or in a mixture of such solvents. Depending on the specific process, the reaction temperature may be varied over a wide range and be, for example, from about −20° C. to the boiling temperature of the solvent or diluent. Also depending on the specific process, it may be necessary or advantageous to add in a suitable amount of one or more auxiliary agents, for example a base like a tertiary amine, such as triethylamine or diisopropylethylamine, or an alkali metal alcoholate, such as sodium methoxide or potassium tert-butoxide, for adjusting the pH or neutralizing an acid that is formed or for liberating the free base of an amino compound that is employed in the form of an acid addition salt, or an N-hydroxyazole like 1-hydroxybenzotriazole, or a catalyst like 4-dimethylaminopyridine. Details on methods for the preparation of activated carboxylic acid derivatives and the formation of amide bonds and ester bonds as well as source literature are given in various standard references like, for example, J. March, Advanced Organic Chemistry, 4th ed., John Wiley & Sons, 1992.

Protective groups that may still be present in the products obtained in the coupling reaction are then removed by standard procedures. For example, tert-butyl protecting groups, in particular a tert-butoxycarbonyl group which is used for protection of an amino group, can be deprotected, i. e. converted into the amino group, by treatment with strong acids (e.g. hydrochloric acid, trifluoroacetic acid). As already explained, after the coupling reaction also functional groups can be generated from suitable precursor groups. In addition, a conversion into a physiologically tolerable salt can then be carried out by known processes.

In general, a reaction mixture containing a final compound of the formulae I and Ia or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

The compounds of the formulae I and Ia, which on account of its chemical structure occur in enantiomeric forms, can be resolved into the pure enantiomers by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups.

The compounds of the formulae I and Ia can be isolated either in free form or, in the case of the presence of acidic or basic groups, converted into physiologically tolerable salts.

The preparation of physiologically tolerable salts of compounds of the formulae I and Ia capable of salt formation, including their stereoisomeric forms, is carried out in a manner known per se. With basic reagents such as hydroxides, carbonates, hydrogencarbonates, alkoxides and also ammonia or organic bases, for example trimethyl- or triethylamine, ethanolamine or triethanolamine or alternatively basic amino acids, for example lysine, ornithine or arginine, the carboxylic acids form stable alkali metal, alkaline earth metal or optionally substituted ammonium salts. If the compounds of the formulae I and Ia contain basic groups, stable acid addition salts can be prepared using strong acids e.g. both inorganic and organic acids such as hydrochloric, hydrobromic, sulfuric, phosphoric, methanesulfonic, benzenesulfonic, p-toluenesulfonic, 4-bromobenzenesulfonic, cyclohexylamido-sulfonic, trifluoromethyl-sulfonic, acetic, oxalic, tartaric, succinic or trifluoroacetic acid are suitable.

The compounds of the formulae I and Ia can especially be prepared by coupling of compounds of formula V to N-(4-carbamimidoyl-phenyl)-malonamic acid VI which is prepared by standard procedures in three steps from commercially available starting materials as illustrated in scheme 1:

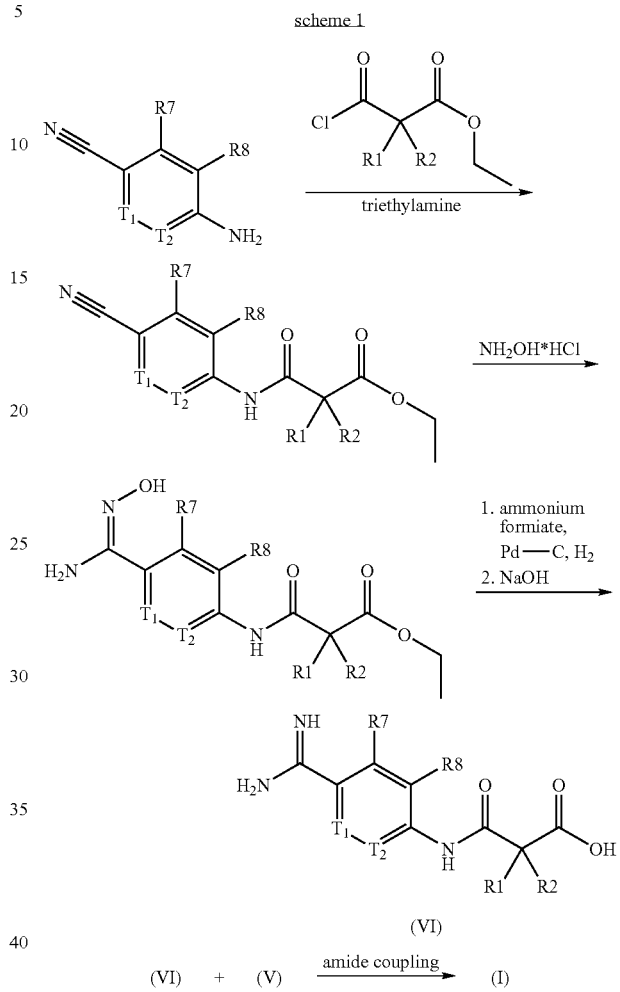

As an alternative, suitable protected derivatives, cyano or hydroxyamidine as precursors of the amidino group can be used. The conversion of the precursor to the amidine is then carried out as the final step. The resulting synthetic plan is illustrated in scheme 2 for the compound of formula Ia:

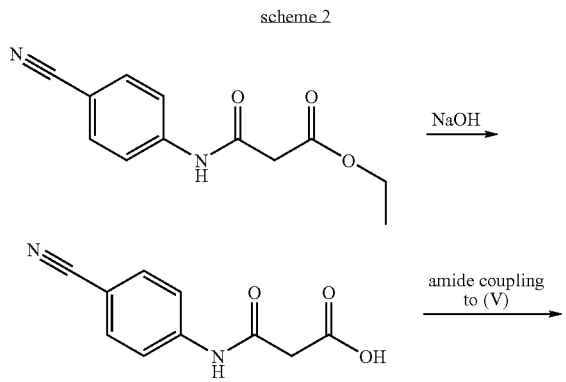

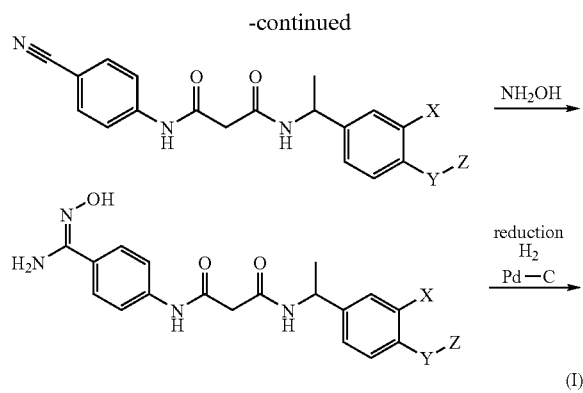

(I)

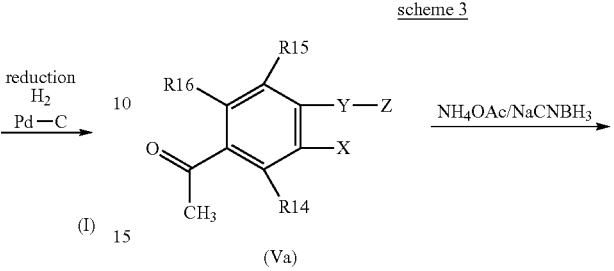

Amidine precursors are usually the corresponding nitriles. For synthetic reasons it might sometimes be advisable to do the transformation to the amidine in any later stage of the synthesis or, often most convenient, even on the last stage, therefore eventually circumventing problems during synthesis.

Several methods for the transformation of the cyanide to the amidine are known; the choice of method depends on the specific chemistry of the transformation and the potential interactions with other functional groups in the targeted molecule. Particularly useful in the present case is the well known Pinner reaction or the nucleophilic addition of hydroxylamine to the nitrile, followed by hydrogenation of the hydroxyamidine. If the latter method is used, it is as well possible, to use the intermediate hydroxyamidine in e. g. coupling reactions, doing the hydrogenation on a latter stage or the last stage of the synthesis (as illustrated in scheme 2).

Amidines and hydroxyamidines might as well be used in a protected state. Amidines and hydroxyamidines can be modified by special residues, which will function as protecting group during synthesis.

Known groups of that kind are especially derivatives of carboxylic acids and carbamic acids like phenoxycarbonyl, benzyloxycarbonyl, 4-methoxybenzyloxy-carbonyl, methoxycarbonyl, ethoxycarbonyl, benzoyl or acetyl.

Compounds of formula V are either commercially available or prepared according to the procedures (Iiven in the schemes and examples below.

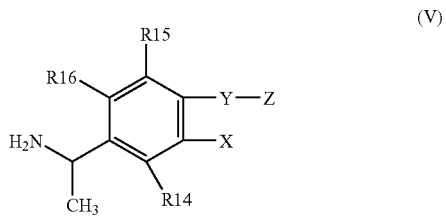

(V)

In general, functionalized amines of formula V can be prepared by many routes described in the literature. For example a suitable precursor for the amines of formula V can be the corresponding acetophenones Va which are commercially available or prepared according to the procedures given in the schemes and examples below. Such acetophenones Va can be transformed to the corresponding amines of formula V by means of a reductive amination procedure employing an ammonia source, for example ammonia or ammonium acetate, in combination with a suitable hydride donor or hydrogen in combination with a suitable catalyst, for example sodium cyanoborohydride, sodium triacetoxyborohydride or $H_2/Pd$—C, $H_2/Raney$-Ni as illustrated in scheme 3:

scheme 3

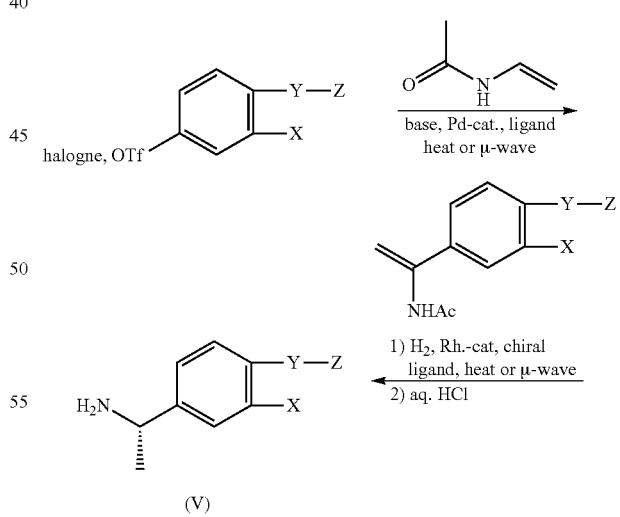

Alternatively, amines of formula V can be prepared from a corresponding suitable halogene or triflate precursor by means of an Heck-type reaction via the corresponding enamides. Enamides offer the possibility of enantioselective hydrogenation employing for example chiral rhodium catalysts in combination with hydrogen and therefore an enantioselective entry into the class of molecules of formula V. This strategy is illustrated in scheme 3b for compounds of formula Ia:

scheme 3b

There are many known ways described in the literature to synthesize acetophenones of formula Va, for example they can be prepared from a suitable halogen precursor VII (for example Br,I) which after transformation to the corresponding Grignard reagent is trapped with acetic anhydride as illustrated in scheme 4.

scheme 4

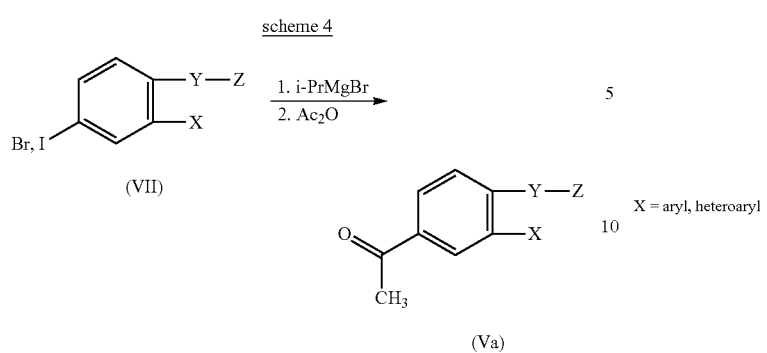

(Va)

Alternatively, acetophenones of formula Va can be prepared from a starting material VIII bearing a functionality like —Br, I or OTf and alkoxyvinyl trialkyltin reagents by means of a Stille reaction and subsequent acidic workup as illustrated in scheme 5.

scheme 5

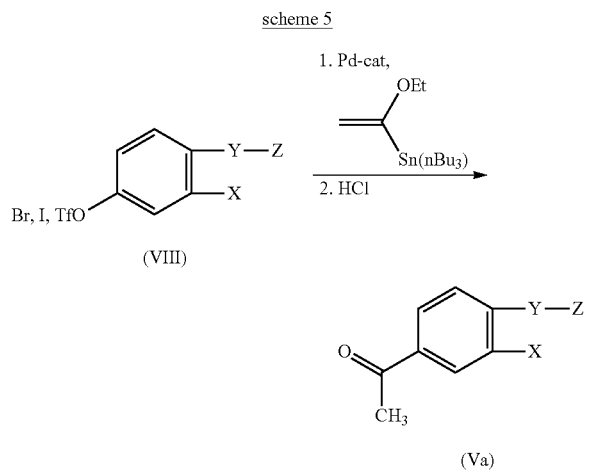

(Va)

Acetophenones of formula Va in the case of X representing an aryl or heteroaryl group can be prepared by cross-coupling reactions well described in the literature. For example a Suzuki-coupling can be employed utilizing a boronic acid or boronic acid ester and a corresponding coupling partner bearing a functionality like —Cl,—Br,I,—OTf as illustrated in scheme 6 or a Negishi-coupling can be employed utilizing an organo-zinc derivative as coupling partner as demonstrated in scheme 7.

scheme 6

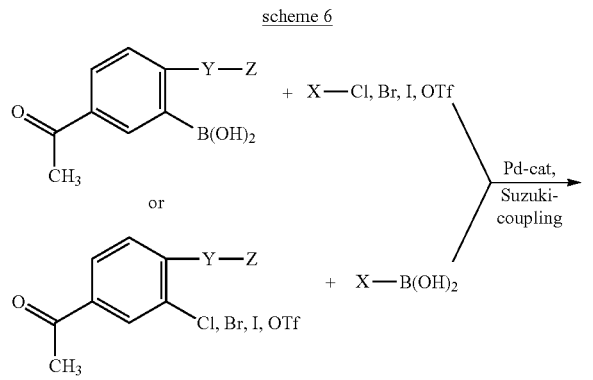

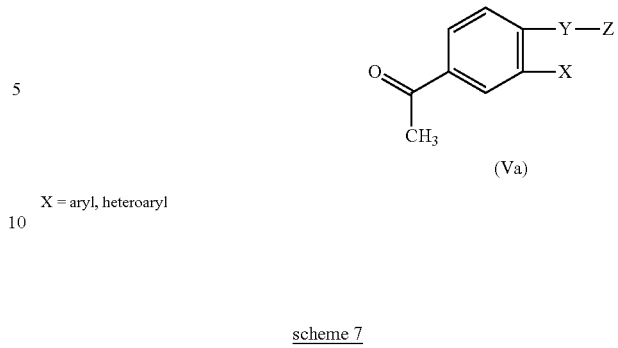

(Va)

X = aryl, heteroaryl scheme 7

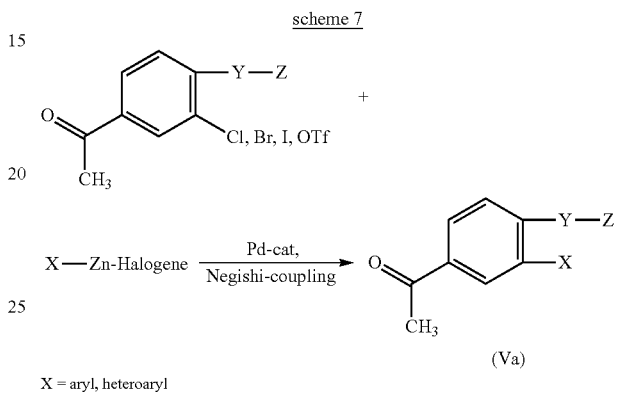

(Va)

X = aryl, heteroaryl

The acetophenones can be transformed to the corresponding amines of formula V as described above.

Alternatively, the before mentioned cross-couplings can be carried out with the corresponding amine already or a protected version thereof (scheme 8).

scheme 8

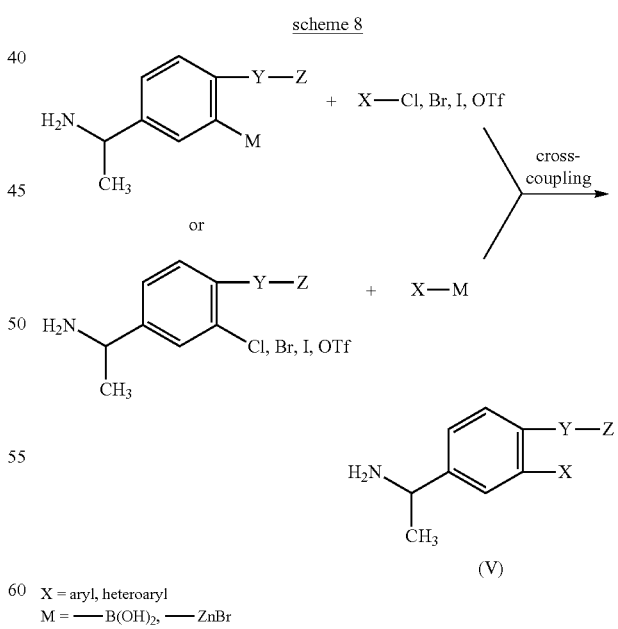

(V)

X = aryl, heteroaryl
M = —B(OH)$_2$, —ZnBr

Acetophenones of formula Va in the case of Y representing an oxygen linker can be prepared by many ways described in the literature. Scheme 9 is just to illustrate one useful strategy. In this respect, aliphatic alcohols or phenols can be introduced by nucleophilic displacement of a suitable leaving group on the acetophenone (e.g. F,Cl) in combination with strong bases (e.g. KF, NaH).

scheme 9

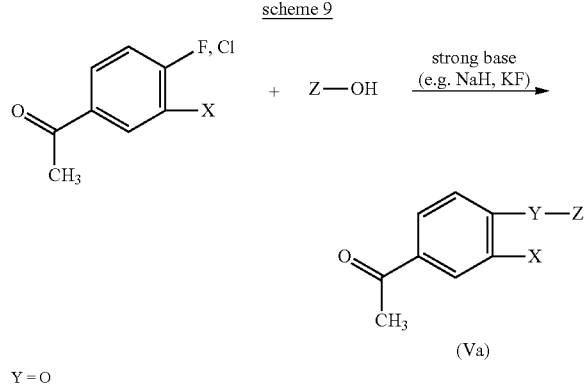

Y = O

The acetophenones can be transformed to the corresponding amines of formula V as described above.

Alternatively, an acetophenone bearing an hydroxyl functionality can be used. Groups Z can then be introduced by standard alkylations using Z—Cl,Br in combination with a suitable base (e.g. $K_2CO_3$) or by standard Mitsunobu alkylation (DIAD, $PPh_3$) using aliphatic alcohols as coupling partner (Z—OH) as shown in scheme 10.

scheme 10

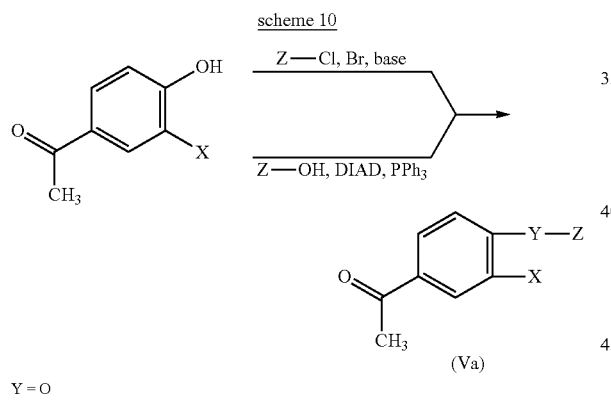

Y = O

The acetophenones can be transformed to the corresponding amines of formula V as described above.

Acetophenones of formula Va in the case of Y representing an nitrogen linker can be prepared by many ways described in the literature. In this respect, amines can be introduced by nucleophilic displacement of a suitable leaving group on the acetophenone (e.g. F, Cl) in combination with or without a suitable base as shown in scheme 11:

scheme 11

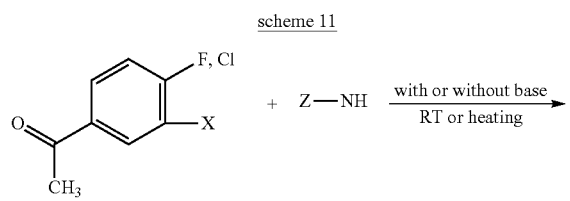

Y = N

The acetophenones can be transformed to the corresponding amines of formula V as described above.

Acetophenones of formula Va in the case of Y representing an sulfur linker can be prepared by many ways described in the literature. In this respect, sodium hydrogen sulphide NaSH can be employed to displace a suitable leaving group on the acetophenone (e.g. F,Cl). The resulting sulfides can be alkylated by strong electrophiles like alkyl iodides or can be used for palladium catalysed cross coupling reactions with aromatic halides. The sulfides generated by these or other methods can in a second step be oxidised through reaction with suitable oxidising reagents (e.g. oxone, $KMnO_4$) to the corresponding sulfones (scheme 12):

scheme 12

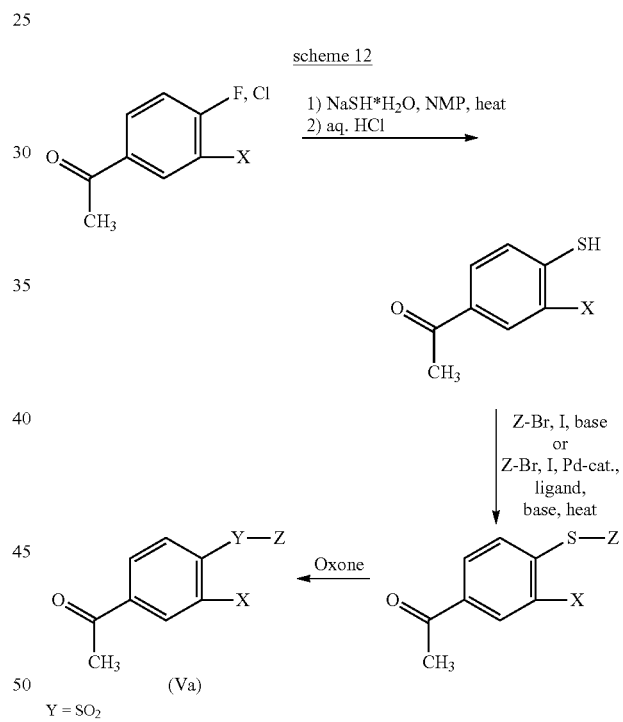

Y = $SO_2$

The acetophenones can be transformed to the corresponding amines of formula V as described above.

The invention also refers to compounds N-(4-Cyano-phenyl)-malonamic acid ethyl ester, N-(4-Cyano-phenyl)-malonamic acid, N-[4-(N-Hydroxycarbamimidoyl)-phenyl]-malonamic acid ethyl ester and N-(4-Carbamimidoyl-phenyl)-malonamic acid, which are useful intermediates in the preparation of the compounds of formulae I and Ia.

Chirality of starting materials: Amines or alcohols to be coupled to the malonate, containing asymmetric centers, can be used in chiral or racemic or any other stereoisomeric form including all kinds of mixtures.

The invention also relates to pharmaceuticals which comprise an efficacious amount of at least one compound of the formulae I and Ia and/or of a physiologically tolerable salt of the compounds of the formulae I and Ia and/or an optionally stereoisomeric form of the compounds of the formulae I and Ia, together with a pharmaceutically suitable and physiologically tolerable excipient, additive and/or other active compounds and auxiliaries.

The compounds of the present invention inhibit the activity of the blood coagulation enzyme factor VIIa either directly, within the extrinsic tenase complex (factor VIIa associated with membrane-protein cofactor, tissue factor) or as a soluble subunit, or indirectly, by inhibiting the assembly of factor VIIa into the extrinsic tenase complex. As a consequence of this inhibition both substrates of factor VIIa, factor X and factor IX will not become activated, prothrombin will not be activated to thrombin by activated factor Xa, thrombin generation will be inhibited and therefore coagulation will be prevented.

Because of their factor VIIa inhibitory activity the compounds of the formulae I and Ia are useful pharmacologically active compounds which are suitable, for example, for influencing blood coagulation (or blood clotting) and fibrinolysis and for the treatment, including therapy and prophylaxis, of diseases such as, for example, cardiovascular disorders, thromboembolic diseases or restenoses. The compounds of the formulae I and Ia and their physiologically tolerable salts can be administered to animals, preferably to mammals, and in particular to humans as pharmaceuticals for therapy or prophylaxis. They can be administered on their own, or in mixtures with one another or in the form of pharmaceutical preparations which permit enteral or parenteral administration and which contain, as active constituent, an effective amount of at least one compound of the formulae I and Ia and/or its physiologically tolerable salts and a pharmaceutically acceptable carrier.

The present invention therefore also relates to the compounds of the formulae I and Ia and/or their physiologically tolerable salts for the production of pharmaceuticals for inhibition of factor VIIa or for influencing blood coagulation or fibrinolysis or for the treatment, including therapy and prophylaxis, of said diseases. Examples are the treatment of cardiovascular disorders, thromboembolic diseases or restenoses.

The present invention furthermore relates to pharmaceutical preparations which contain an effective amount of at least one compound of the formulae I and Ia and/or its physiologically tolerable salts and a pharmaceutically acceptable carrier, e.g. one or more pharmaceutically acceptable carrier substances and/or additives.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formulae I and Ia and/or its (their) physiologically tolerable salts. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils. Suitable carriers for the production of solutions, for example injection solutions, or of emulsions or syrups are, for example, water, saline, alcohols, glycerol, polyols, sucrose, invert sugar, glucose, vegetable oils. Suitable carrier substances for microcapsules, implants or rods are, for example, copolymers of glycolic acid and lactic acid. The pharmaceutical preparations normally contain about 0.5 to about 90% by weight of the compounds of the formulae I and Ia and/or their physiologically tolerable salts. The amount of the active ingredient of the formulae I and Ia and/or its physiologically tolerable salts in said preparations is from about 0.5 to about 1000 mg, preferably from 1 to 500 mg.

In addition to the active ingredients of the formulae I and Ia and/or their physiologically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formulae I and Ia and/or their physiologically tolerable salts. In case a pharmaceutical preparation contains two or more compounds of the formulae I and Ia the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formulae I and Ia allows a great deal of control over the biological and physico-chemical properties of the compounds and thus allows the selection of such desired compounds. Furthermore, in addition to at least one compound of the formulae I and Ia and/or its physiologically tolerable salts, the pharmaceutical preparations can also contain one or more other therapeutically or prophylactically active ingredients.

As inhibitors of factor VIIa the compounds of the formulae I and Ia and their physiologically tolerable salts are generally suitable for the therapy and prophylaxis of conditions in which the activity of factor VIIa plays a role or has an undesired extent, or which can favorably be influenced by inhibiting factor VIIa or decreasing its activity, or for the prevention, alleviation or cure of which an inhibition of factor VIIa or a decrease in its activity is desired by the physician. As inhibition of factor VIIa influences blood coagulation and fibrinolysis the compounds of the formulae I and Ia and their physiologically tolerable salts are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention is the reduction or inhibition of unwanted blood clotting, in particular in an individual, by administering an effective amount of a compound I or a physiologically tolerable salt thereof, as well as pharmaceutical preparations therefor.

The compound of the formulae I and Ia and/or a physiologically tolerable salt thereof can be used for the treatment of e.g. abnormal thrombus formation, acute myocardial infarction, cardiovascular disorders, unstable angina, thromboembolism, acute vessel closure associated with thrombolytic therapy or percutaneous transluminal coronary angioplasty (PTCA), transient ischemic attacks, stroke, intermittent claudication, bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, viral infections or cancer, or reducing an inflammatory response, fibrinolysis, or treatment of coronary heart disease, myocardial infarction, angina pectoris, vascular restenosis, for example restenosis following angioplasty like PTCA, adult respiratory distress syndrome, multi-organ failure and disseminated intravascular clotting disorder, deep vein or proximal vein thrombosis, which can occur following surgery.

In view of their pharmacological activity the compounds of the invention can replace other anticoagulant agents such as heparin. The use of a compound of the invention can result, for example, in a cost saving as compared to other anticoagulants.

When using the compounds of the formulae I and Ia the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formulae I and Ia can also advantageously be used as an anticoagulant outside an individual. For example, an effective amount of a compound of the invention can be contacted with a freshly drawn blood sample to prevent coagulation of the blood sample. Further, a compound of the formulae I and Ia and its salts can be used for diagnostic purposes, for example in in vitro diagnoses, and as an auxiliary or tool in biochemical investigations. Compounds of the formulae I and Ia can thus be used in an assay to identify the presence of factor VIIa or to isolate factor VIIa in a substantially purified form. A compound of the invention can be labeled with a radioisotope, and the labeled compound bound to factor VIIa is then detected using a routine method useful for detecting the particular label. Thus, a compound of the formulae I and Ia or a salt thereof can be used advantageously as a probe to detect the location or amount of factor VIIa activity in vivo, in vitro or ex vivo.

Further, the compounds of the formulae I and Ia can be used as synthesis intermediates for the preparation of other compounds, in particular of other pharmaceutical active ingredients, which are obtainable from the compounds of the formulae I and Ia, for example by introduction of substituents or modification of functional groups.

It is understood that modifications that do not substantially affect the activity of the various embodiments of this invention are included within the invention disclosed herein. Accordingly, the following examples are intended to illustrate but not limit the present invention.

EXAMPLES

Abbreviations:

AcOEt ethyl acetate

ACN acetonitrile

Ambient temperature 10° C. to 50° C.

DCM dichloromethane

DIPEA N,N-diisopropylethylamine

DMF dimethylformamide

DMSO dimethyl sulfoxide

FA formic acid h hour(s)

HATU O-(7-azabenzotriazol-1-yl)-N,N,N',N'-tetramethyluronium hexafluorophosphate HOAt 1-hydroxy-7-azabenzotriazole HPLC high performance liquid chromatography LC/MS liquid chromatography mass spectrometry MeOH methanol PyBrop bromo-tris-pyrrolidino-phosphonium hexafluorophosphate RT room temperature $R_t$ retention time TBDMS-Cl tert-butyldimethylchlorosilane TEA triethylamine TFA trifluoroacetic acid Synthesis of Intermediates:

Intermediate 1:

N-(4-Cyano-phenyl)-malonamic acid ethyl ester

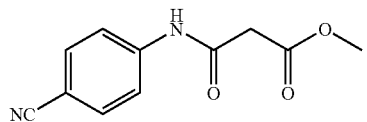

To a solution of 4-aminobenzonitrile (18.0 g, 0.149 mol) and triethylamine (27.34 ml, 0.194 mol) in DCM (600 ml) ethylmalonylchloride (25.0 g, 21.36 ml, 0.149 mol) in DCM (30 ml) was added. The reaction mixture was stirred at RT for 1.5 h. To the red solution water was added. The organic phase was washed with sodium hydrogen carbonate and HCl (1 M) and afterwards dried over magnesium sulphate, filtered and evaporated. The crude product was recrystallized from ethyl acetate/n-heptane to give 24.05 g (69%) of the title compound.

Intermediate 2:

N-(4-Cyano-phenyl)-malonamic acid

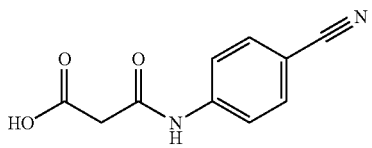

Intermediate 1 (11.1 g, 47.9 mmol) was dissolved in methanol (300 mL) and lithium hydroxide (1.72 g, 71.8 mmol) dissolved in water (100 mL) was added. The reaction was stirred at RT overnight. The solvent was evaporated, water was added and the aqueous layer was washed with ethyl acetate, acidified with hydrochloric acid (4 N) and again extracted with ethyl acetate. The organic layer was separated, dried over sodium sulfate, filtered and evaporated to give 8.75 g (yield: 89%) of the titled compound. LC/MS (method D) (M+H)$^+$: 205

Intermediate 3:

N-[4-(N-Hydroxycarbamimidoyl)-phenyl]-malonamic acid ethyl ester

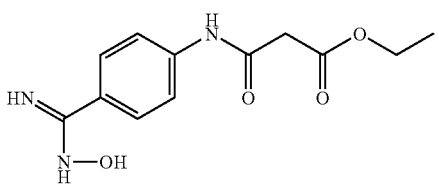

To a solution of N-(4-Cyano-phenyl)-malonamic acid ethyl ester (19.8 g, 85.26 mmol) in ethanol (800 ml) hydroxylamine hydrochloride (17.78 g, 255.80 mmol) and triethylamine (107 ml, 767.3 mmol) were added. The reaction mixture was stirred for 20 h at RT. The solvent was evaporated and the crude product was dissolved in ethyl acetate. Water was added and the aqueous phase was extracted with ethyl acetate. The combined organic phases were dried over magnesium sulphate and evaporated to yield the product (16.82 g, 74%) as a white solid.

Intermediate 4:

N-(4-Carbamimidoyl-phenyl)-malonamic acid*trifluoro-acetic acid salt

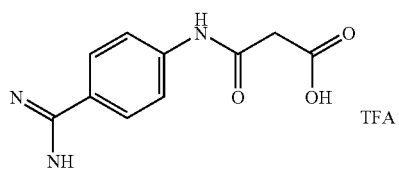

To a solution of N-[4-(N-hydroxycarbamimidoyl)-phenyl]-malonamic acid ethyl ester (16.9 g, 63.41 mmol) and ammonium formate (20.0 g, 317.1 mmol) in glacial acetic acid (400 ml) Pd/C, 10% (675 mg) was added. The suspension was stirred for 5 h under reflux. The reaction mixture was filtered through celite and evaporated. The crude product was dissolved in ethanol (400 ml) and treated with an aqueous solution of sodium hydroxide (2 M, 300 ml). The reaction mixture was stirred for 4 h at RT and then hydrochloric acid (2 N) was added (pH=8). The suspension was filtered and the solid was dissolved in ACN/water and acidified with trifluoroacetic acid (pH=1). Lyophilization left the product (9.88 g, 46%) as a white solid.

SYNTHESIS OF EXAMPLE COMPOUNDS

The following examples have been prepared, isolated and characterized using the methods disclosed herein. The following examples demonstrate a partial scope of the invention and are not meant to be limiting of the scope of the invention. The other examples not described in detail can be prepared in analogy.

Example 1

5-(2-Bromo-4-{(S)-1-[2-(4-carbamimidoyl-phenyl-carbamoyl)-acetylamino]-ethyl}-phenoxyynicotinic acid*acetic acid salt

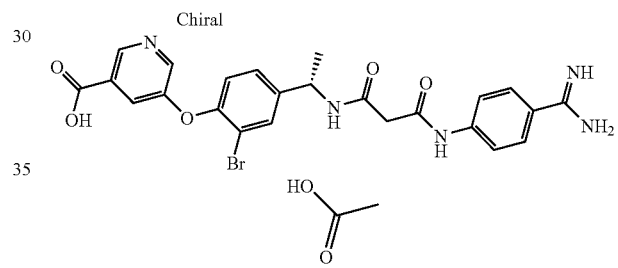

Step 1:

Methyl-5-(4-acetyl-2-bromo-phenoxy)-nicotinate

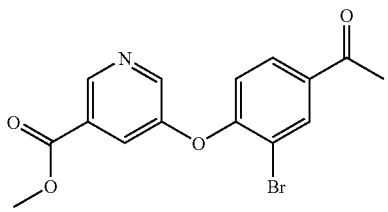

Methyl-5-hydroxynicotinate (1.0 g, 6.53 mmol), 3'-bromo-4'-fluoroacetophenone (1.42 g, 6.53 mmol), 18-crown-6 (155.3 mg, 0.59 mmol) and potassium fluoride (40 wt. % on alumina, 996 mg, 6.86 mmol) were dissolved in ACN (10 mL). The reaction was refluxed for three days. After cooling the mixture was quenched with 2N aqueous potassium carbonate solution, extracted with ether, dried with sodium sulphate, filtered, evaporated and purified by silica gel chromatography (ethyl acetate:n-heptane 1:4). 635 mg (yield: 28%) of the pure compound was obtained.

LC/MS (method D) (M+H)$^+$: 351

Step 2:

Methyl-5-[4-(1-amino-ethyl)-2-bromo-phenoxy]-nicotinate

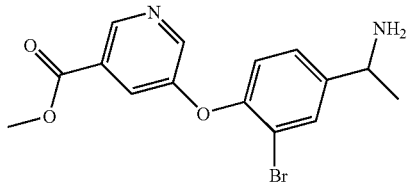

To a solution of the compound from step 1 (630 mg, 1.79 mmol) in MeOH (30 mL) ammonium acetate (1.39 g, 17.9 mmol) was added. After stirring at ambient temperature overnight sodium cyanoborohydride (135.7 mg, 2.16 mmol) was added and the reaction was refluxed for 6 h. The solvent was evaporated and the solid, dissolved in ethyl acetate, was extracted with water. The organic layer was separated, washed with brine, dried over sodium sulphate, filtered and evaporated to give 606 mg (yield: 96%) of the crude product. LC/MS (method D) (M+H)$^+$: 352

Step 3:

Methyl-5-(2-bromo-4-{1-[2-(4-cyano-phenylcarbamoyl)-acetylamino]-ethyl}-phenoxy)-nicotinate

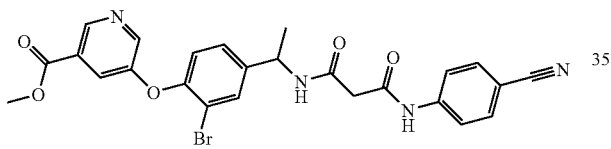

To a solution of 600 mg (1.71 mmol) of the compound derived from step 2, N-(4-cyano-phenyl)-malonamic acid (intermediate 2) (349 mg, 1.71 mmol), HOAt (233 mg, 1.71 mmol) and HATU (649 mg, 1.71 mmol) in DMF (8 mL) was added DIPEA (0.88 mL, 5.12 mmol) and this solution was allowed to stir for 48 h at ambient temperature. The mixture was diluted with water, extracted with ethyl acetate, dried over sodium sulphate, filtered, evaporated and purified by preparative HPLC. The relevant fractions were lyophilized to give 360 mg (yield: 39%) of the product as a white solid.
LC/MS (method D) (M+H)$^+$: 538

Step 4:

Methyl-5-[2-bromo-4-(1-{2-[4-(N-hydroxycarbamimidoyl)-phenylcarbamoyl]-acetylaminoyethylyphenoxy]-nicotinate

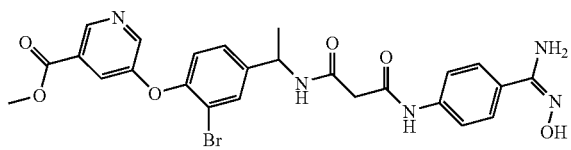

The product derived from step 3 (360 mg, 0.67 mmol) and hydroxylamine hydrochloride (280 mg, 4.02 mmol) were dissolved in isopropanol and TEA (0.65 mL, 4.69 mmol) was added. The reaction was heated at 70° C. and stirred for 4 h. The cooled mixture was treated with water and extracted with ethyl acetate. The organic layer was separated, dried over sodium sulphate, filtered and evaporated. Finally 310 mg (yield: 81%) of the pure compound was obtained.
LC/MS (method D) (M+H)$^+$: 571

Step 5:

5-[2-Bromo-4-(1-{2-[4-(N-hydroxycarbamimidoyl)-phenylcarbamoyl]-acetylamino}-ethyl)-phenoxy]-nicotinic acid*hydrochloric acid salt

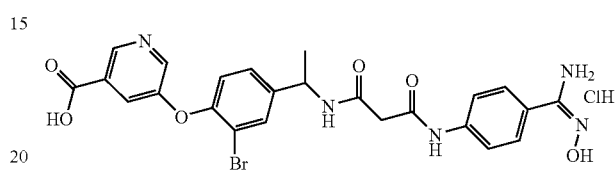

The compound from step 4 (230 mg, 0.40 mmol) was dissolved in MeOH (10 mL) and lithium hydroxide (14.5 mg, 0.60 mmol), dissolved in H$_2$O (2.5 mL), was added. The reaction mixture was stirred at 50° C. for 2 h and then overnight at ambient temperature. The reaction mixture was quenched with water, acidified to pH 6 with 1 molar hydrochloric acid and extracted with ethyl acetate. Most of the product remains in the aqueous layer which is lyophilized to give 265 mg of the crude compound.
LC/MS (method D) (M)$^+$: 556

Step 6:

5-(2-Bromo-4-{1-[2-(4-carbamimidoyl-phenylcarbamoyl)-acetylamino]-ethyl}-phenoxy)-nicotinic acid*trifluoro-acetic acid salt

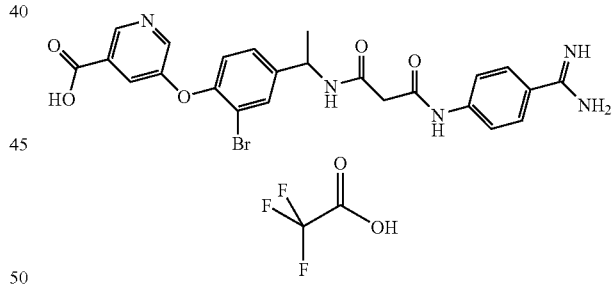

The product derived from step 5 (50 mg, 0.075 mmol) was dissolved in acetic acid (5 mL) and palladium on activated carbon (10%, 8 mg, 0.007 mmol) and acetic anhydride (7.75 μL, 0.082 mmol) were added. The reaction was hydrogenated (1 bar H$_2$) at ambient temperature for 2.5 h. The mixture was filtered, the organic solvent was removed under reduced pressure and the residue was purified by prep-HPLC to give 18 mg (yield: 37%) of the product. LC/MS (method D) (M+H)$^+$: 541

Step 7:

5-(2-Bromo-4-{(S)-1-[2-(4-carbamimidoyl-phenylcarbamoyl)-acetylamino]-ethyl}-phenoxy)-nicotinic acid*acetic acid salt (Example 1)

The racemic product yielded from step 6 (16 mg, 24.45 μmol) was separated in its enantiomers by chiral preparative HPLC [column: (S,S) Whelk-O 250×50 mm, company Regis Technologies, Inc., 8210 Austin Avenue, Morton Grove, Ill. 60053, USA; eluent: heptane, ethanol and methanol (1:1:1)+ 0.1% ammonium acetate (isocratic), flow rate: 50 mL/min]. The relevant fractions were lyophilized. Yield: 4 mg (27%). LC/MS (method D) main peak (M+H)$^+$: 541 (R$_t$=0.94 min)

Example 2

N-{1-[3-Bromo-4-(3-hydroxymethyl-phenoxy)-phenyl]-ethyl}-N'-(4-carbamimidoyl-phenyl) malonamide*trifluoro-acetic acid salt

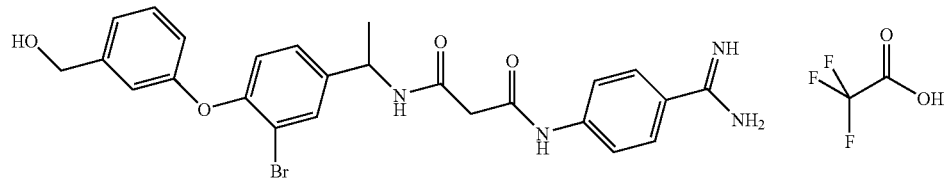

Step 1:

3-(tert-Butyl-dimethyl-silanyloxymethyl)-phenol

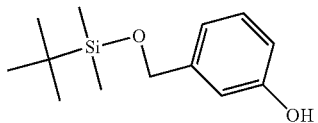

To a solution of 3-hydroxybenzyl alcohol (5.00 g, 40.3 mmol) in DCM (25 mL) imidazole (13.7 g, 201.4 mmol) and TBDMS-Cl (6.68 g, 44.3 mmol) were added and the solution was stirred at RT for 1 h. The reaction was quenched with water, extracted with ethyl acetate, dried over sodium sulphate, filtered, evaporated and purified by silica gel chromatography (ethyl acetate:n-heptane 1:4). Finally 5.16 g (yield: 54%) of the pure compound was obtained.

LC/MS (method D) (M+H-tertbutyl,-dimethyl)$^+$: 156

Step 2:

1-{3-Bromo-4-[3-(tert-butyl-dimethyl-silanyloxymethyl)-phenoxy]-phenylyethanone

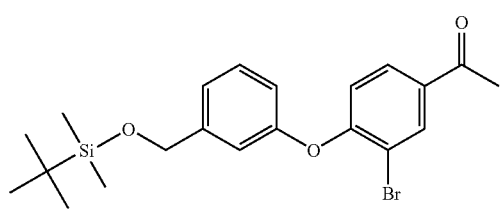

The product derived from step 1 (1.00 g, 4.19 mmol), 3'-bromo-4'-fluoroaceto-phenone (910 mg, 4.19 mmol), 18-crown-6 (99.8 mg, 0.38 mmol) and potassium fluoride (40 wt. % on alumina, 640 mg, 4.40 mmol) were dissolved in ACN (5 mL). The reaction was stirred for 30 min at 120° C. in the microwave. The mixture was quenched with water, extracted with ethyl acetate, dried over sodium sulphate, filtered, evaporated and purified by silica gel chromatography (ethyl acetate:n-heptane 1:10). Finally 1.35 g (yield: 74%) of the title compound was obtained.

LC/MS (method D) (M+H)$^+$: 436

Step 3:

1-{3-Bromo-4-[3-(tert-butyl-dimethyl-silanyloxymethyl)-phenoxy]-phenyl}-ethylamine

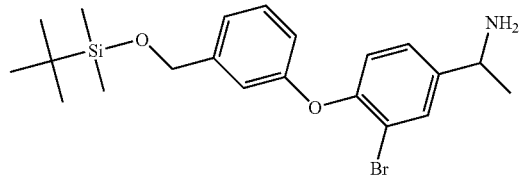

In analogy to the preparation of example 1, step 2, the compound from step 2 (1.35 g, 3.10 mmol) was reacted to give 1.28 g (yield: 95%) of the solid product.

LC/MS (method D) (M+H—NH$_2$)$^+$: 422

Step 4:

N-{1-[3-Bromo-4-(3-hydroxymethyl-phenoxy)-phenyl]-ethyl}-N'-(4-cyano-phenyl)-malonamide

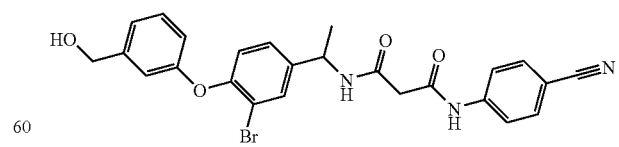

In analogy to the preparation of example 1, step 3, the compound derived from step 3 (1.28 g, 2.93 mmol) was reacted to give 129 mg (yield: 9%) of the title compound. The TBDMS protecting group was removed during the preparative HPLC separation.

Step 5:

N-{1-[3-Bromo-4-(3-hydroxymethyl-phenoxy)-phenyl]-ethyl}-N'-[4-(N-hydroxycarbamimidoyl)-phenyl]-malonamide

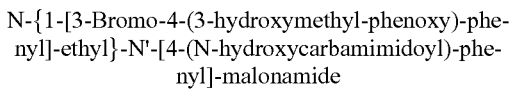

In analogy to the preparation of example 1, step 4, the crude product derived from step 4 (129 mg, 0.25 mmol) was converted yielding 125 mg (yield: 91%) of the title compound. LC/MS (method D) (M+H)$^+$: 542

Step 6:

N-{1-[3-Bromo-4-(3-hydroxymethyl-phenoxy)-phenyl]-ethyl}-N'-(4-carbamimidoyl-phenyl)-malonamide*trifluoro-acetic acid salt (Example 2)

In analogy to the preparation of example 1, step 6, the compound derived from step 5 (85 mg, 0.13 mmol) was converted to yield 18 mg (yield: 22%) of the title product as a white solid. LC/MS (method A) main peak (M–H)$^+$: 524 ($R_t$=1.18 min)

Example 10

N-(4-Carbamimidoyl-phenyl)-N'—{(S)-1-[4-(2-methoxy-ethoxy)-3-trifluoromethyl-phenyl]-ethyl}-malonamide

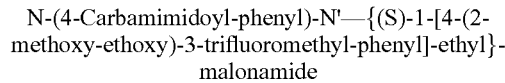

Step 1:

1-[4-(2-Methoxy-ethoxy)-3-trifluoromethyl-phenyl]-ethanone

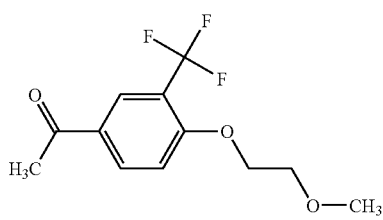

832 µl (10.5 mmol) of 2-methoxyethanol was dissolved in 15 ml absolute DMSO and to this solution NaH (504 mg (10.5 mmol)) was added. After stirring for 1 hour at RT 1.44 g (7 mmol) of 4-fluoro-3-trifluoromethyl-acetophenone was added and the mixture was stirred for an additional hour. The reaction was quenched with ice/water, extracted with DCM, dried over sodium sulphate, filtered, evaporated under reduced pressure and purified by chromatography on silica gel. Yield: 1.13 g (62%)

LC/MS (method A) (M+1)$^+$: 262.08

Step 2:

1-[4-(2-Methoxy-ethoxy)-3-trifluoromethyl-phenyl]-ethylamine triflouroacetate

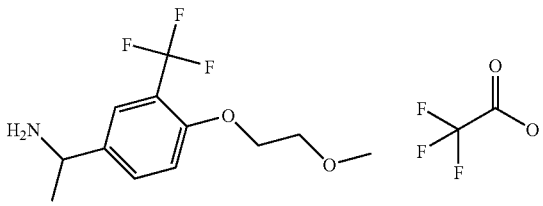

To a solution of 1.1 g (4.1 mmol) of 1-[4-(2-methoxy-ethoxy)-3-trifluoromethyl-phenyl]-ethanone derived from step 1 dissolved in 30 mL methanol was added 3.3 g (42 mmol) of NH$_4$CO$_2$CH$_3$ and the mixture was stirred at ambient temperature for about 3 h. Subsequently 400 mg (6.3 mmol) NaBH$_3$(CN) was added and the reaction mixture refluxed for 6 h. Then the solution was evaporated, the residue dissolved in 40 mL DMF, the solids filtered off and the residue evaporated to dryness again. The raw material was purified by reversed phase chromatography. Yield: 840 mg (isolated as trifluoroacetate, 2.2 mmol, 53%).

LC/MS (method A): 247.07 (MW: 263.1)

Step 3:

N-(4-Carbamimidoyl-phenyl)-N'-{1-[4-(2-methoxy-ethoxy)-3-trifluoromethyl-phenyl]-ethyl}-malonamide

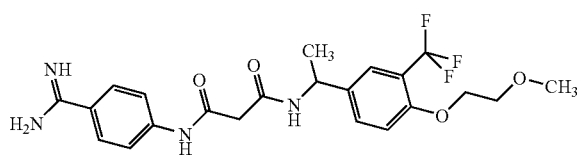

211 mg (0.660 mmol) of N-(4-carbamimidoyl-phenyl)-malonamic acid (intermediate 4) was dissolved in absolute DMF and to this solution 273 mg (0.73 mmol) of the amine derived from step 2, 98.8 mg (0.73 mmol) 1-hydroxy-7-azobenzotriazole, 307 mg (2.4 mmol) N,N-diisopropy-ethylamine and 338 mg (0.73 mmol) of bromo-tris-pyrolidino-phosphonium-hexafluorophosphate were added. After stirring at ambient temperature for 24 h the reaction mixture was filtered, evaporated under reduced pressure and purified by preparative HPLC. Yield: 95 mg (25%), colorless solid.

LC/MS (method A) (M+H)$^+$: 467.30

Step 4:
Separation of Enantiomers

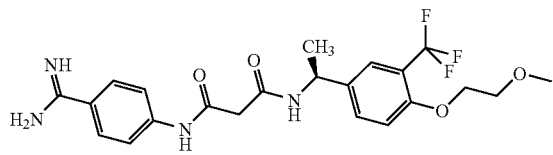

The racemic product derived from step 3 (90 mg, 0.17 mmol) was separated into its stereoisomers by chiral preparative HPLC [column: (S,S) Whelk-O 250×50 mm, eluent: heptane, ethanol and methanol (1:1:1)+0.1% ammonium acetate (isocratic), flow rate: 50 mL/min]. The relevant fractions were lyophilized yielded 23 mg (26%) of the relevant enantiomer. LC/MS (method A) (M+H)$^+$: 467.30 (Rt(1.047 min.)

Example 14

N-(4-Carbamimidoyl-phenyl)-N'—((S)-1-{4-[(2-methoxy-ethyl)-methyl-amino]-3-trifluoromethyl-phenyl}-ethyl)-malonamide*acetic acid salt

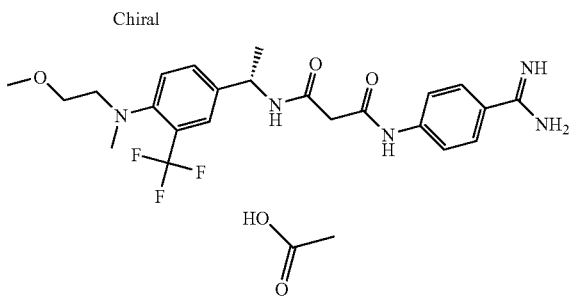

Step 1:

1-{4-[(2-Methoxy-ethyl)-methyl-amino]-3-trifluoromethyl-phenyl}-ethanone

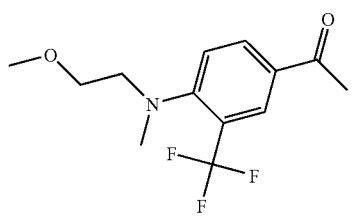

A solution of 4-fluoro-3-(trifluoromethyl)acetophenone (500 mg, 2.43 mmol), N-(2-methoxyethyl)methylamine (649 mg, 7.28 mmol) and potassium carbonate (335 mg, 2.43 mmol) in DMSO (6 mL) was stirred for 30 min at 150° C. in the microwave. The cooled reaction mixture was diluted with water, extracted with ethyl acetate, dried over sodium sulphate, filtered and the solvent was removed under reduced pressure. Finally 547 mg (yield: 82%) of the title compound was obtained.
LC/MS (method D) (M+H)$^+$: 276

Step 2:

[4-(1Amino-ethyl)-2-trifluoromethyl-phenyl]-(2-methoxy-ethyl)-methyl-amine*trifluoro-acetic acid

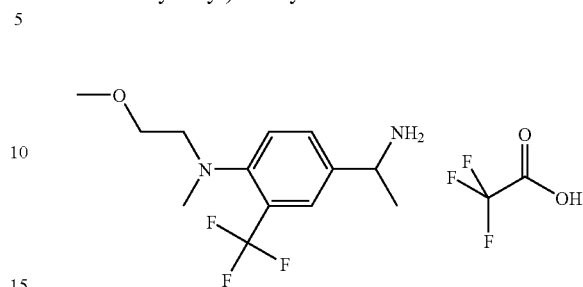

Ammonium acetate (1.53 g, 19.8 mmol) was added to a solution of the compound from step 1 (545 mg, 1.98 mmol) in MeOH (8 mL). After stirring at RT overnight sodium cyanoborohydride (149 mg, 2.38 mmol) was added and the reaction was refluxed for 6 h. The solvent was evaporated and the solid, redissolved in ethyl acetate, was extracted with water. The organic layer was separated, washed with brine, dried over sodium sulphate, filtered, evaporated and purified by preparative HPLC. The relevant fractions were lyophilized to give 147 mg (yield: 19%) of the pure product.
LC/MS (method D) (M+H)$^+$: 277

Step 3:

N-(4-Carbamimidoyl-phenyl)-N'-(1-{4-[(2-methoxy-ethyl)-methyl-amino]-3-trifluoromethyl-phenyl}-ethyl)-malonamide*trifluoro-acetic acid salt

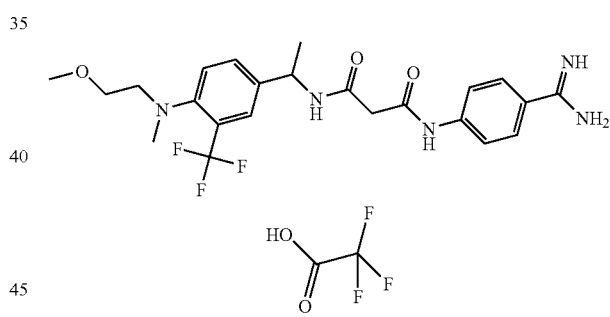

To a solution of the compound received in step 2 (100 mg, 0.26 mmol), N-(4-carbamimidoyl-phenyl)-malonamic acid*trifluoro-acetic acid salt (intermediate 4) (86 mg, 0.26 mmol) and HOAt (34.9 mg, 0.26 mmol) in DMF (4 mL) was added DIPEA (131 µL, 0.77 mmol) under stirring for 10 min. After the addition of PyBrop (119 mg, 0.26 mmol) the reaction was stirred at ambient temperature for 24 h. The mixture was filtered and purified by preparative HPLC. The relevant fractions were lyophilized to yield 46 mg (yield: 30%) of the pure compound.
LC/MS (method D) (M+H)$^+$: 480

Step 4:

N-(4-Carbamimidoyl-phenyl)-N'-((S)-1-{4-[(2-methoxy-ethyl)-methyl-amino]-3-trifluoromethyl-phenyl}-ethyl)-malonamide*acetic acid salt (Example 3)

The racemic product derived from step 3 (38 mg, 64.0 µmol) was separated in its enantiomers by chiral preparative HPLC [column: (S,S) Whelk-O1 250×50 mm, eluent: heptane, ethanol and methanol (5:1:1)+0.1% ammonium acetate (isocratic), flow rate: 100 mL/min]. The relevant fractions were lyophilized to yield 9 mg (yield: 26%) of the pure compound.

LC/MS (method A) main peak (M+H)$^+$: 479 ($R_t$=1.24 min)

Example 17

N-(4-Carbamimidoyl-phenyl)-N'-{(S)-1-[4-(pyridin-4-ylmethoxy)-3-trifluoromethyl-phenyl]-ethyl}-malonamide

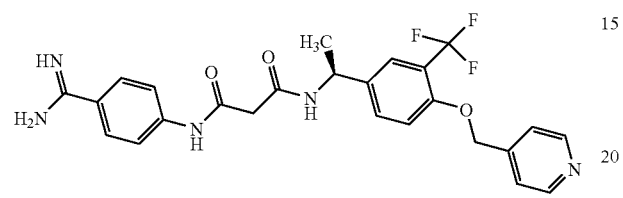

Step 1:

1-[4-(Pyridin-4-ylmethoxy)-3-trifluoromethyl-phenyl]-ethanone

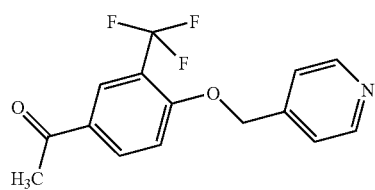

1.02 g (5 mmol) of 4-hydroxy-3-trifluoromethyl-acetophenone was dissolved in 10 ml absolute THF and cooled to 0° C. Subsequently 660 mg (5.5 mmol) of pyridine-4-methanol, 1.443 g (5.5. mmol) of triphenylphosphine and 1.213 g of diisiopropylazodi-carboxylate were added and the mixture stirred at 0° C. for 1 h and 12 h at ambient temperature. The mixture was diluted with water, extracted with ethyl acetate, dried over sodium sulphate, filtered, evaporated and purified by prep-HPLC. The relevant fractions were lyophilized to give 585 mg (isolated as trifluoroacetate, yield: 29%) of the product as colourless crystals. LC/MS (method A) (M+H)$^+$: 296.06 (Rt 1.15 min.) The product was used for step 2 directly.

Step 2:

1-[4-(Pyridin-4-ylmethoxy)-3-trifluoromethyl-phenyl]-ethylamine

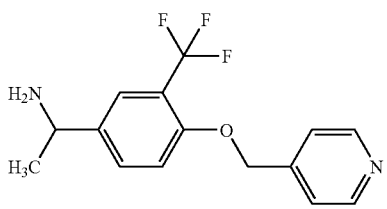

585 mg (1.43 mmol) of the compound prepared in step 1 was dissolved in 15 ml absolute MeOH and to this solution 1.11 g (14.3 mmol) of NH$_4$CO$_2$CH$_3$ was added. After 6 h at ambient temperature 1.35 g (2.2 mmol) NaCNBH$_3$ was added and the mixture refluxed for 6 h. The mixture was evaporated under reduced pressure and dissolved in 20 mL of DMF, filtered from solids and again evaporated. The resulting oil was purified by preparative HPLC. The relevant fractions were lyophilized to give 182 mg (43%) of the product as colourless crystals.

LC/MS (method A) (M+H)$^+$: 297.09 (Rt 0.71 min.)

The product was used for step 3 without further purification.

Step 3:

N-(4-Carbamimidoyl-phenyl)-N'-{1-[4-(pyridin-4-ylmethoxy)-3-trifluoromethyl-phenyl]-ethyl}-malonamide

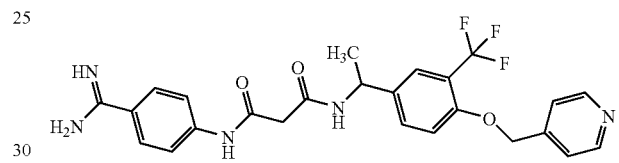

134.1 mg (0.4 mmol) of N-(4-carbamimidoyl-phenyl)-malonamic acid*trifluoro-acetic acid salt (intermediate 4) was dissolved in absolute DMF and to this solution 118.5 mg (0.4 mmol) of the amine from step 2, 509 mg (0.8 mmol) 1-propane-phoshonic-acid-anhydride and 51.7 mg (0.4 mmol) N,N-diisopropy-ethyl-amine were added. After stirring for 24 h at ambient temperature the reaction mixture was filtered, evaporated to dryness and purified by preparative HPLC. Yield 45 mg (18%), colourless crystals.

LC/MS (method A) (M+H)$^+$: 500.3 ($R_t$ 1.05 min.)

Step 4:

N-(4-Carbamimidoyl-phenyl)-N'-{(S)-1-[4-(pyridin-4-ylmethoxy)-3-trifluoromethyl-phenyl]-ethyl}-malonamide

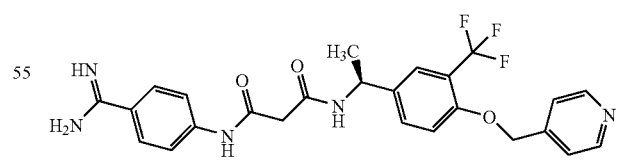

The racemic product derived from step 3 (18 mg) was separated in its enantiomers by chiral preparative HPLC [column: (S,S) Whelk-O 250×50 mm, eluent: heptane, ethanol and methanol (3:1:1)+0.1% ammonium acetate (isocratic), flow rate: 50 mL/min]. The relevant fractions were lyophilized to give 4 mg (22%) of the pure compound.

LC/MS (method A) (M+H)$^+$: 500.3 ($R_t$ 0.823 min.)

Example 20

4-(4-{1-[2-(4-Carbamimidoyl-phenylcarbamoyl)-acetylamino]-ethyl}-2-trifluoro-methyl-phenoxy)-butyric acid

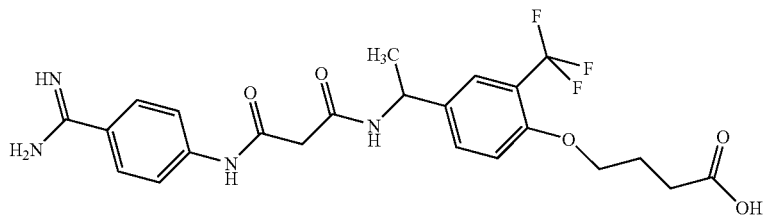

Step 1

4-(4-Acetyl-2-trifluoromethyl-phenoxy)-butyric acid ethyl ester

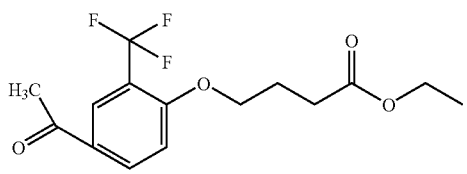

To a solution of 4-Hydroxy-3-(trifluoromethyl)-acetophenone (2.042g, 10 mmol) in 50 ml DMF were added 1.52 g (11 mmol) of K$_2$CO$_3$ and 1.951 g (10 mmol) of 4-bromo-butyric acid ethyl ester. The reaction mixture was stirred for 1 h at 80° C. The solvent was evaporated; the residue dissolved in 100 ml DCM and extracted trice with 30 ml water. The resulting organic phase was dried over Na$_2$SO$_4$, evaporated and purified by silica gel chromatography (mobile phase heptane/ethylacetate=3/1) yielding 3.02 g (95%) of the title compound as a light yellow oil.

LC/MS (method A) (M+1)$^+$: 319.3

Step 2

4-[4-(1-Amino-ethyl)-2-trifluoromethyl-phenoxy]-butyric acid ethyl ester

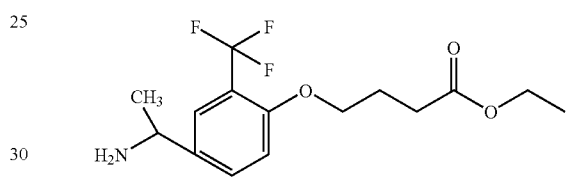

To 3.02 g (95 mmol) of the acetophenone from step 1 in 50 ml MeOH was added 7.31 g ammonium acetate (95 mmol). After 12 h stirring at ambient temperature 715 mg (11.4 mmol) sodium cyanoborohydride was added and the mixture heated for 8 h under reflux. The solvent was evaporated under reduced pressure, the residue redissolved in ethylacetate and the organic phase extracted three times with water. The organic layer was separated, washed with brine, dried over Na$_2$SO$_4$, filtered and evaporated. After chromatography of the residue on silica gel 1.0 g (3.13 mmol; yield 33%) of the crude product was obtained.

LC/MS (method A) (M+1)$^+$: 303.08 (MW 319.14; Rf 1.25 min.)

Step 3

4-(4-{1-[2-(4-Carbamimidoyl-phenylcarbamoyl)-acetylamino]-ethyl}-2-trifluoromethyl-phenoxy)-butyric acid ethyl ester

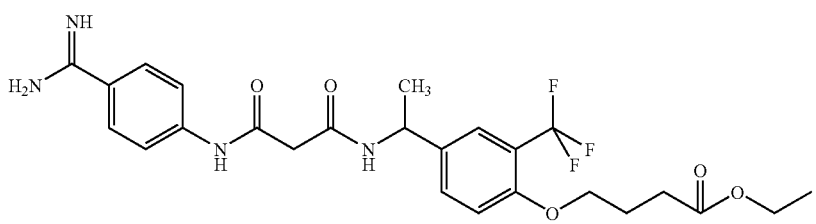

268 mg (0.8 mmol) of N-(4-carbamimidoyl-phenyl)-malonamic acid (intermediate 4) was dissolved in absolute DMF and to this solution was added 255.5 mg (0.8 mmol) of the amine from step 2, 1.018 g (1.6 mmol), 1-propane-phosphonic acid anhydride and 103.4 mg (0.8 mmol) N,N-diisopropyl-ethyl-amine. The solution was stirred for 18 h at ambient temperature. Then the reaction mixture was evaporated, the residue dissolved in ethyl acetate and extracted with water. The separated organic layer was dried over sodium sulphate, evaporated under reduced pressure and the resulting residue purified by preparative HPLC. 170 mg (2.7 mmol, yield 33%) of the pure compound was obtained.

LC/MS (method A) (M+1)+: 523.18 (MW 319.14; Rf 1.407 min.).

Step 4

4-(4-{1-[2-(4-Carbamimidoyl-phenylcarbamoyl)-acetylamino]-ethyl}-2-trifluoro-methyl-phenoxy)-butyric acid

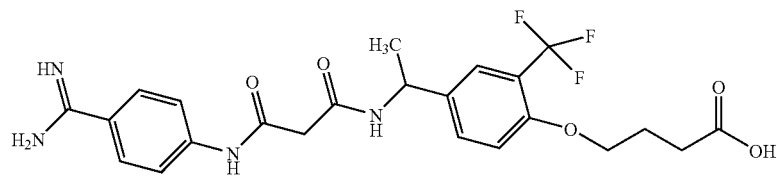

To 170 mg (2.7 mmol) of 4-(4-{1-[2-(4-carbamimidoyl-phenylcarbamoyl)-acetyl-amino]-ethyl}-2-trifluoromethyl-phenoxy)-butyric acid ethyl ester from step 3 in 15 ml methanol was added one equivalent of 1 n aqueous sodium hydroxide and the reaction mixture was stirred for 2 h at ambient temperature. Then the mixture was acidified to pH 3 by the addition of 1 N aqueous HCl and the resulting precipitate was separated by filtration. After lyophilization 29 mg (0.059 mmol, 22%) of the pure compound was obtained. LC/MS (method A) (M+1)+: 495.2 (Rf 0.981 min.)

Example 28

N-(4-Carbamimidoyl-phenyl)-N'-{1-[4-(morpholine-4-sulfonyl)-3-trifluoromethyl-phenyl]-ethyl}-malonamide*trifluoro-acetic acid salt

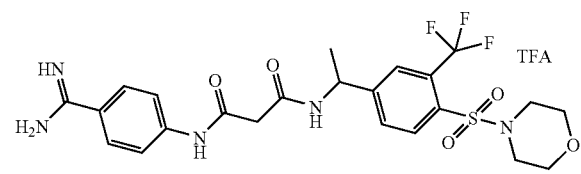

Step 1:

4-(4-Bromo-2-trifluoromethyl-benzenesulfonyl)-morpholine

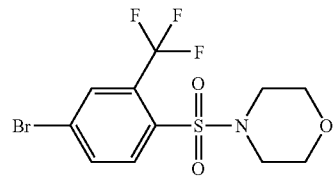

A solution of 4-bromo-2-trifluoromethyl-benzenesulfonyl chloride (5.00 g, 15.46 mmol) in THF (5 ml) was added to a solution of morpholine (1.62 ml, 18.55 mmol) and triethylamine (2.15 ml, 15.46 mmol) in tetrahydrofurane. The reaction mixture was stirred for 12 h at RT. Ethyl acetate (80 ml) was added, the organic phase was separated and washed with water (20 ml), hydrochloric acid (1 M, 20 ml) and brine (20 ml) and dried over sodium sulphate. After evaporation the product was obtained (5.708 g, 99%) and used in the next step without further purification.

Step 2:

1-[4-(Morpholine-4-sulfonyl)-3-trifluoromethyl-phenyl]-ethanone

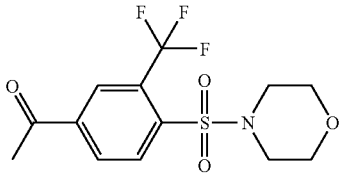

A solution of isopropylmagnesium chloride (2M in THF, 10 ml, 20.04 mmol) was added drop wise to a solution of the product obtained in step 1 (5.00 g, 13.36 mmol) in THF (30 ml) at −10° C. The mixture was stirred at this temperature for 1 h and then added drop wise to acetic acid anhydride (12.6 ml, 133.60 mmol) at −15° C. The reaction mixture was stirred at 0° C. for 2 h and allowed to warm up slowly to RT. Water (100 ml) was added and the reaction mixture was stirred at 60° C. for 15 min. The mixture was diluted with ethyl acetate at RT, neutralized with aqueous NaHCO3, washed with brine, dried over sodium sulphate and evaporated. Purification of the crude product by silica gel chromatography using ethyl acetate/n-heptane gave the desired product (2.00 g, 44%).

Step 3:

1-[4-(Morpholine-4-sulfonyl)-3-trifluoromethyl-phenyl]-ethylamine

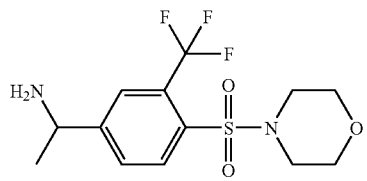

Ammonium acetate (4.57 g, 59.29 mmol) and sodium cyanoborohydride (373 mg, 5.93 mmol) were added to a solution of the compound received in step 2 (2.00 g, 5.93 mmol) in MeOH (30 mL). The reaction mixture was refluxed for 5 h. Then the mixture was quenched by addition of trifluoroacetic acid (pH=2) and evaporated to dryness. Purification of the crude product by preparative HPLC and lyophilization of the relevant fractions gave the desired product (1.48 g, 55%).

LC/MS (method E) (M+H)$^+$: 338

Step 4:

N-(4-Carbamimidoyl-phenyl)-N'—{(S)-1-[4-(morpholine-4-sulfonyl)-3-trifluoromethyl-henyl]-ethyl}-malonamide*trifluoro-acetic acid salt (Example 5)

DIPEA (0.23 mL, 1.33 mmol) was added to a solution of the product derived from step 3 (200 mg, 0.44 mmol), N-(4-Carbamimidoyl-phenyl)-malonamic acid trifluoro-acetic acid salt (intermediate 4) (148 mg, 0,44 mmol) and TOTU (145 mg, 0.44 mmol) in DMF (6 mL). The received solution was stirred at ambient temperature for 12 h. The mixture was acidified with trifluoroacetic acid and purified by preparative HPLC. The relevant fractions were lyophilized to give 156 mg (yield: 54%) of the product as a white solid.

LC/MS (method F) (M+H)$^+$: 541

Example 29

N-(4-Carbamimidoyl-phenyl)-N'—[(S)-1-(3-pentafluoroethyl-phenyl)-ethyl]-malonamide; compound with trifluoro-acetic acid

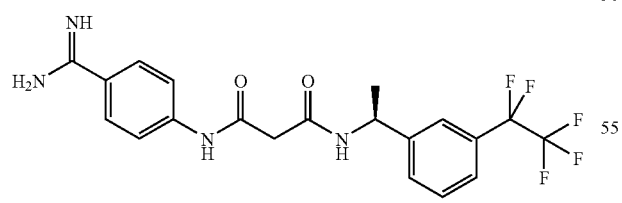

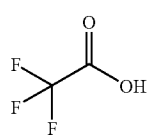

Step 1:
Trifluoro-methanesulfonic acid 3-pentafluoroethyl-phenyl ester

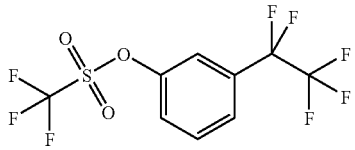

To a solution of 3-pentafluoroethyl-phenol (2.0 g, 9.43 mmol) and triethylamine (1.24 g, 1.63 ml, 12.26 mmol) in dichloromethane (10 ml) was added trifluoromethane-sulfonic anhydride (1.76 ml, 2.99 g, 10.37 mmol) at 0° C. The reaction mixture was stirred 6 h at room temperature. Dichloromethane (15 ml) was added and the organic phase was washed with solutions of ammonium chloride (saturated, 2×10 ml), sodium carbonate (1M, 2×15 ml) and brine (15 ml). The organic phase was dried over sodium sulphate and concentrated in vacuo leading to an oil (2.83 g, 87%), which was used in the following step without further purification.

Step 2:

N-[1-(3-Pentafluoroethyl-phenyl)-vinyl]-acetamide

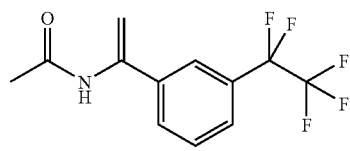

To a solution of the crude product of step 1 (0.75 g, 2.2 mmol) in DMF (10 ml) was added N-vinylacetamide (0.37 g, 4.36 mmol), triethylamine (243 mg, 0.33 ml, 2.40 mmol), palladium acetate (20 mg, 4 mol %) and bis(diphenylphosphino)propane (40 mg, 0.1 mmol). The reaction mixture was heated for 30 min at 130° C. using microwaves. The red solution was diluted and washed with hydrochloric acid (1M, 2×15 ml) and sodium hydrogen carbonate (saturated, 20 ml). The organic phase was dried over sodium sulphate and evaporated. Purification of the crude product by silica gel chromatography using ethyl acetate/n-heptane (2:1) gave the desired product.

Step 3:

1-(3-Pentafluoroethyl-phenyl)-ethylamine

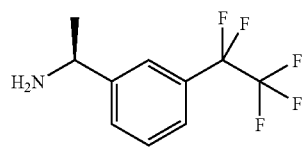

To a solution of N-[1-(3-Pentafluoroethyl-phenyl)-vinyl]-acetamide (110 mg, 0.39 mmol) in methanol (10 ml) was added (+)-1,2-bis((2S,5S)-2,5-diethylphospholano)benzene (cyclooctadiene)rhodium (I) trifluoromethanesulfonate (0.3 mg). The reaction mixture was hydrogenated with H$_2$ at 5 bar and evaporated. The residue was dissolved in ethanol and hydrochloric acid (6 M, 0.7 ml) and the solution was refluxed for 2 days. Purification by preparative HPLC and lyophilization of the relevant fractions gave the desired product.

Step 4:

N-(4-Carbamimidoyl-phenyl)-N'—[(S)-1-(3-pentafluoro-ethyl-phenyl)-ethyl]-malonamide; compound with trifluoro-acetic acid (Example 29)

To a solution of the product derived from step 3 (5 mg, 14 µM) in DMF (0.2 ml) TOTU (5 mg, 14 µM), and N-(4-Carbamimidoyl-phenyl)-malonamic acid trifluoro-acetic acid salt (intermediate 4) (5 mg, 14 µmol) were added. The reaction mixture was stirred at ambient temperature for 12 h. The mixture was acidified with trifluoroacetic acid and purified by preparative HPLC. The relevant fractions were lyophilized to give 3 mg (yield: 42%) of the product as a white solid. LC/MS (method F) (M+H)+: 541

Example 64

N-[1-(4-Acetylsulfamoyl-3-chloro-phenyl)-ethyl]-N'-(4-carbamimidoyl-phenyl)-malonamide; compound with trifluoro-acetic acid

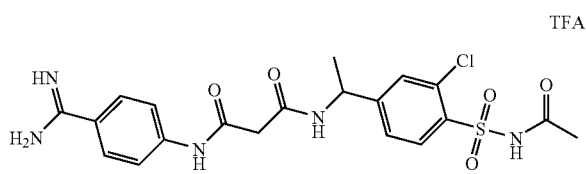

Step 1:

4-Bromo-2-chloro-benzenesulfonamide

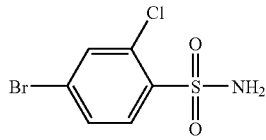

To a solution of 4-bromo-2-chlorobenzenesulfonyl chloride (2.50 g, 8.45 mmol) in THF (25 ml) was added a solution of ammonia (25%, 6.3 ml, 84.5 mmol). The reaction mixture was stirred for 4 h at RT. Ethyl acetate (70 ml) and water (50 mL) were added. The organic phase was separated and washed with hydrochloric acid (1 M, 50 ml) and brine (2×30 ml) and dried over sodium sulfate. After evaporation the product was obtained as a white solid (2.05 g, 90%) which was used in the next step without further purification.

Step 2:

4-Acetyl-2-chloro-benzenesulfonamide

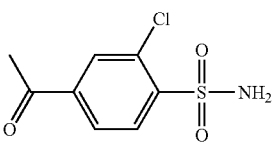

To a solution of the product obtained in step 1 (1.0 g, 3.70 mmol) in ACN (8 ml) was added CuI (35 mg, 185 µmol), PdCl$_2$(PPh$_3$)$_2$ (389 mg, 554 µmol) and 1-(ethoxyvinyl)tributyl-stannane (2.5 ml, 2.60 g, 7.39 mmol). The mixture was heated for 30 min at 100° C. using microwaves. After cooling, the reaction mixture was acidified with 1 N HCl (4 ml) and stirred for 20 min. The reaction mixture was adjusted to pH=7 using NaHCO$_3$ and extracted with AcOEt. The organic phase was washed with brine, dried over Na$_2$SO$_4$ and evaporated. Purification of the crude product by silica gel chromatography using ethyl acetate/n-heptane (1:1) gave the desired product (650 mg, 75%).

Step 3:

4,N-Diacetyl-2-chloro-benzenesulfonamide

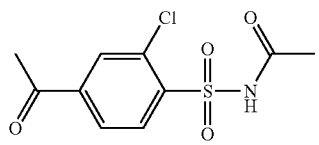

To a solution of the product obtained in step 2 (0.40 mg, 1.71 mmol) in ACN (3 ml) was added acetic anhydride. Concentrated sulphuric acid (2.8 µl, 5 mg, 51 µM) was added at 60° C. and the reaction mixture was stirred for 40 min at that temperature. The cooled reaction mixture was diluted with water, extracted with dichloromethane, dried over sodium sulfate, filtered and the solvent was removed under reduced pressure. The desired product was obtained (yield: 460 mg, 97%) and used in the following step without further purification.

Step 4:

N-Acetyl-4-(1-amino-ethyl)-2-chloro-benzene-sulfonamide

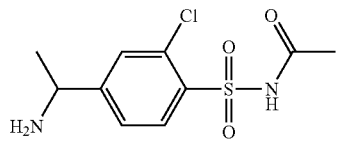

Ammonium acetate (1.10 g, 14.87 mmol) and sodium cyanoborohydride (93 mg, 1.49 mmol) were added to a solution of the compound received in step 3 (410 mg, 1.49 mmol) in MeOH (4 mL). The reaction mixture was refluxed for 2 h. Then the cooled mixture was treated with trifluoroacetic acid to reach pH=2 and evaporated to dryness. Purification of the crude product by preparative HPLC and lyophilization of the relevant fractions gave the desired product (210 mg, 36%).

Step 5:

N-[1-(4-Acetylsulfamoyl-3-chloro-phenyl)-ethyl]-N'-(4-carbamimidoyl-phenyl)-malonamide; compound with trifluoro-acetic acid To a solution of the product derived from step 4 (210 mg, 537 µmol), N-(4-carbamimidoyl-phenyl)-malonamic acid*trifluoro-acetic acid salt (intermediate 3) 180 mg, 537 µmol) and TOTU (176 mg, 537 µmol) in DMF (5 mL) was added DIPEA (276 µL, 208 mg, 1.6 mmol) and this solution was stirred 2 h at ambient temperature. The mixture was acidified with trifluoroacetic acid and purified by prep-HPLC. The relevant fractions were lyophilized and the desired product was obtained as a white solid (yield: 135 mg, 42%). LC/MS (method F) (M+H)+: 479.1

Example 66

N-(4-Carbamimidoyl-phenyl)-N'-{1-[3-chloro-4-(tetrahydro-pyran-4-sulfonyl)-phenyl]-ethyl}-malonamide*trifluoro-acetic acid salt

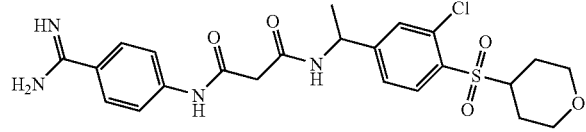

Step 1:

1-(3-Chloro-4-mercapto-phenyl)ethanone

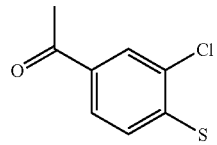

Sodium hydrogen sulfide (NaSH×H2O) (10.97 g, 148.1 mmol)) was dehydrated in N-methylpyrrolidone (100 ml) at 160° C. under argon. 3,4-dichloro-acetophenone (11.20 g, 59.25 mmol) was added to the mixture at 140° C. and stirring was continued for 3 h at 160° C. The solvent was removed under reduced pressure and water (100 ml) and hydrochloric acid (6 N) were added to the crude product. The precipitate was filtered, washed and purified by silica gel chromatography using ethyl acetate/n-heptane to yield 7.55 g (yield: 68%) of the. desired product LC/MS (M+H)+: 196

Step 2:

1-[3-Chloro-4-(tetrahydro-pyran-4-ylsulfanyl)-phenyl]-ethanone

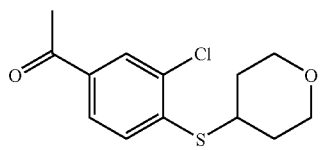

The product from step 1 (3.0 g, 16.07 mmol) was added to a suspension of sodium hydride (964.3 mg, 32.14 mmol) in DMF at 0° C. After 5 min 4-iodo-tetrahydro-pyran (3.41 g, 16.07 mmol) was added and the reaction mixture was stirred at RT for 1 h. The reaction mixture was quenched with water at 0° C. and neutralized with trifluoroacetic acid. Evaporation and purification of the crude product by silica gel chromatography using ethyl acetate/n-heptane gave the desired product (1.385 g, 32%)

Step 3:

1-[3-Chloro-4-(tetrahydro-pyran-4-sulfonyl)-phenyl]-ethanone

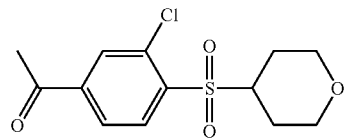

A solution of the product obtained from step 2 (1.38 g, 5.10 mmol) in methanol (25 ml) and tetrahydrofurane (25 ml) was added drop wise to a solution of oxone (5.64 g, 9.17 mmol) in water (25 ml) at 0° C. The suspension was stirred 2 days at RT. Water (25 ml) was added and the reaction mixture was extracted with DCM. The combined organic phases were washed with brine and dried over magnesium sulphate. Evaporation and purification of the crude product by silica gel chromatography using ethyl acetate/n-heptane gave the desired product (1.04 g, 67%).

Step 4:

1-[3-Chloro-4-(tetrahydro-pyran-4-sulfonyl)phenyl]-ethylamine

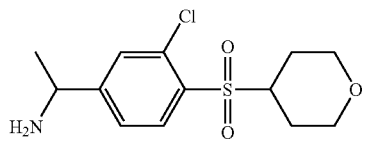

Ammonium acetate (2.65 g, 34.35 mmol) and sodium cyanoborohydride (216 mg, 3.44 mmol) were added to a suspension of the compound derived from step 3 (1.04 g, 3.44 mmol) in methanol (10 mL). The reaction mixture was refluxed for 5 h. Then the mixture was quenched by addition of trifluoro acetic acid (pH=2) and evaporated to dryness. Purification of the crude product by preparative HPLC and lyophilization of the relevant fractions gave the desired product (740 mg, 52%).

Step 5:

DIPEA (0.31 mL, 1.79 mmol) was added to a solution of the product derived from step 4 (250 mg, 0.60 mmol), N-(4-Carbamimidoyl-phenyl)-malonamic acid*trifluoro-acetic acid salt (intermediate 4) (201 mg, 0.60 mmol) and TOTU (196 mg, 0.60 mmol) in DMF (6 mL) and the received solution was stirred at ambient temperature for 12 h. The mixture was acidified with trifluoroacetic acid and purified by preparative HPLC. The relevant fractions were lyophilized to give 195 mg (yield: 53%) of the product as a white solid. LC/MS (method F) (M+H)+: 442.

Example 73

N-(4-Carbamimidoyl-phenyl)-N'-[1-(3-trifluo-romethanesulfinyl-phenyl)-ethyl]-malonamide*trifluoro-acetic acid salt (Example 73)

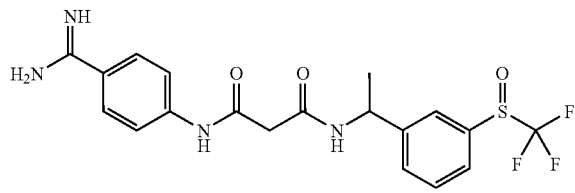

Step 1:

1-(3-Trifluoromethanesulfinyl-phenyl)ethanone

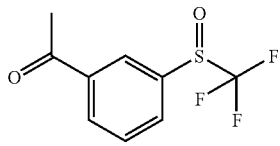

To a solution of 1-(3-trifluoromethylsulfanyl-phenyl)ethanone (1.4 g, 6.36 mmol) in methanol (30 ml) and THF (30 ml) a solution of oxone, monopersulfate compound (10.94 g, 17.8 mmol) in water (50 ml) was added dropwise over a period of 10 min. The reaction mixture was stirred at 60° C. for 3 days. The organic solvent was removed in vacuo and the aqueous phase was extracted with dichloromethane. Evaporation of the combined organic layers and purification of the crude product by silica gel chromatography using ethyl acetate/n-heptane gave the desired product (0.66 g, 44%). 1-(3-Trifluoromethanesulfonyl-phenyl)ethanone (190 mg, 12%) was obtained as a side product which was used for the synthesis of example 77.

Step 2:

1-(3-Trifluoromethanesulfinyl-phenyl)ethylamine

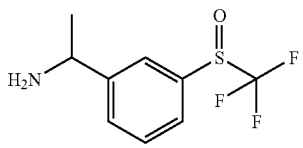

Ammonium acetate (0.62 g, 8.04 mmol) and sodium cyanoborohydride (51 mg, 0.80 mmol) were added to a suspension of the compound derived from step 1 (0.2 g, 0.80 mmol) in methanol (5 mL). The reaction mixture was refluxed for 5 h. Then the mixture was quenched by addition of hydrochloric acid (6N) to reach pH=4. Evaporation and purification of the crude product by preparative HPLC and lyophilization of the relevant fractions gave the desired product (130 mg, 68%).

Step 3:

N-(4-Carbamimidoyl-phenyl)-N'-[1-(3-trifluo-romethanesulfinyl-phenyl)-ethyl]-malonamide*trifluoro-acetic acid salt (Example 73)

DIPEA (213 mg, 280 µl, 1.64 mmol) was added to a solution of the product derived from step 2 (130 mg, 0.55 mmol), N-(4-carbamimidoyl-phenyl)-malonamic acid*trifluoroacetic acid salt (intermediate 3) (184 mg, 0,55 mmol) and TOTU (180 mg, 0.55 mmol) in DMF (4 mL) and the received solution was stirred at ambient temperature for 12 h. The mixture was acidified with trifluoroacetic acid and purified by preparative HPLC. The relevant fractions were lyophilized to give 67 mg (yield: 22%) of the product as a white solid. LC/MS (method E) (M+H)$^+$: 440.

Example 74

N-(4-Carbamimidoyl-phenyl)-N'-{1-[4-(pyridine-4-sulfonyl)-3-trifluoromethyl-phenyl]-ethyl}-malonamide*trifluoro-acetic acid salt

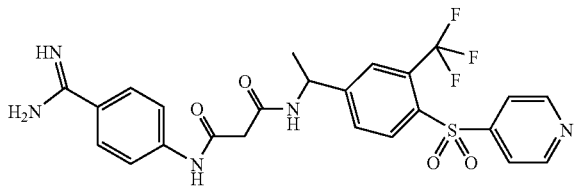

Step 1:

1-(4-Mercapto-3-trifluoromethyl-phenyl)-ethanone

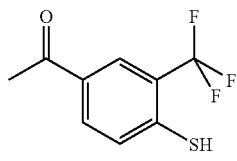

Sodium hydrogen sulfide hydrate (NaSH×H2O) (15.81 g, 213.4 mmol)) was dehydrated in N-methylpyrrolidone (150 ml) at 160° C. under argon. 4-Chloro-3-trifluoromethyl)acetophenone (19.00 g, 85.36 mmol) was added to the mixture at 140° C. and stirring was continued for 3 h at 160° C. The solvent was removed under reduced pressure and water (100 ml) and hydrochloric acid (6 N) were added to the crude product. The precipitate was filtered, washed and purified by silica gel chromatography using ethyl acetate/n-heptane to yield 13.00 g (yield: 69%) of the desired product.

Step 2:

1-[4-(Pyridin-4-ylsulfanyl)-3-trifluoromethyl-phenyl]-ethanone

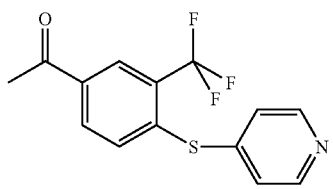

To a solution of the product derived from step 1 (4.5 g, 22.44 mmol) in dioxane (60 ml) was added 4-bromopyridine (3.50 g, 22.48 mmol), DIPEA (7.7 ml, 5.81 g, 44.97 mmol), tris(dibenzylideneacetone)dipalladium(0) (468 mg, 0.51 mmol) and 4,5-bis(diphenylphosphino)-9,9-dimethylxanthene (591 mg, 1.02 mmol). The reaction mixture was heated at 150° C. for 30 min using microwaves. The reaction mixture was evaporated and the crude product was purified by silica gel chromatography using ethyl acetate/n-heptane 1:1 to give the desired product (4.80 g, 79%).

Step 3:

1-[4-(Pyridine-4-sulfonyl)-3-trifluoromethyl-phenyl]-ethanone

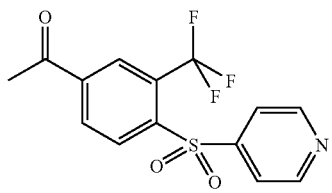

To a solution of the product obtained from step 2 (4.80 g, 16.15 mmol) in methanol (80 ml) and tetrahydrofurane (80 ml) was added drop wise to a solution of oxone, monopersulfate compound (17.87 g, 29.07 mmol) in water (80 ml) at 0° C. The suspension was stirred 4 days at RT. Water (100 ml) was added and the reaction mixture was extracted with DCM. The combined organic phases were washed with brine and dried over magnesium sulphate. Evaporation and purification of the crude product by silica gel chromatography using DCM/methanol=20:1 gave the desired product (2.80 g, 53%).

Step 4:

1-[4-(Pyridine-4-sulfonyl)-3-trifluoromethyl-phenyl]-ethylamine

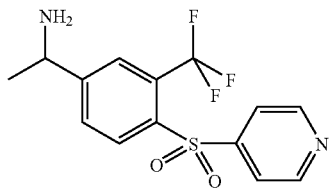

Ammonium acetate (6.50 g, 85.03 mmol) and sodium cyanoborohydride (534 mg, 8.50 mmol) were added to a suspension of the compound derived from step 3 (2.80 g, 8.50 mmol) in methanol (60 mL). The reaction mixture was stirred at RT for 16 h. Then the mixture was quenched by addition of trifluoro acetic acid to reach pH=3. Evaporation and purification of the crude product by preparative HPLC and lyophilization of the relevant fractions gave the desired product (1.18 g, 31%).

Step 5:

N-(4-Carbamimidoyl-phenyl)-N'-{1-[4-(pyridine-4-sulfonyl)-3-trifluoromethyl-phenyl]-ethyl}-malonamide*trifluoro-acetic acid salt (Example 74)

DIPEA (0.58 ml, 3.38 mmol) was added to a solution of the product derived from step 4 (500 mg, 1.13 mmol), N-(4-carbamimidoyl-phenyl)-malonamic acid*trifluoro-acetic acid salt (intermediate 4) (377 mg, 1.125 mmol) and TOTU (369 mg, 1.125 mmol) in DMF (8 mL) and the received solution was stirred at ambient temperature for 2 h. The mixture was acidified with trifluoroacetic acid and purified by preparative HPLC. The relevant fractions were lyophilized to give 320 mg (yield: 44%) of the product as a white solid. LC/MS (method E) (M+H)$^+$: 533.

Example 77

N-(4-Carbamimidoyl-phenyl)-N'—[(S)-1-(3-trifluoromethanesulfonyl-phenyl)-ethyl]-malonamide*trifluoro-acetic acid salt

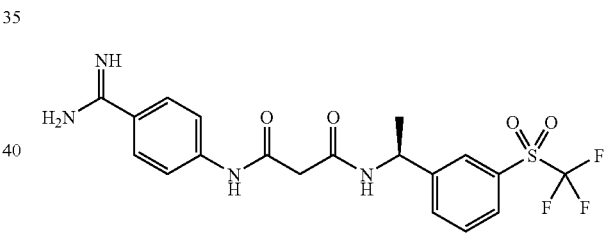

Step 1:

1-(3-Trifluoromethanesulfonyl-phenyl)ethylamine

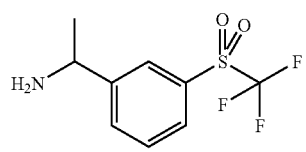

Ammonium acetate (0.58 g, 7.53 mmol) and sodium cyanoborohydride (47 mg, 0.75 mmol) were added to a suspension of the by-product derived from step 1, example 73 (0.19 g, 0.75 mmol) in methanol (5 mL). The reaction mixture was refluxed for 5 h. Then the mixture was quenched by addition of hydrochloric acid (6N) to reach pH=4. Evaporation and purification of the crude product by preparative HPLC and lyophilization of the relevant fractions gave the desired product (111 mg, 58%).

Step 2:

N-(4-Carbamimidoyl-phenyl)-N'—[(S)-1-(3-trifluo-
romethanesulfonyl-phenyl)-ethyl]-
malonamide*trifluoro-acetic acid salt (Example 77)

DIPEA (168 mg, 220 μl, 1.30 mmol) was added to a solution of the product derived from step 1 (111 mg, 0.43 mmol), N-(4-carbamimidoyl-phenyl)-malonamic acid*trifluoro-acetic acid salt (intermediate 4) (146 mg, 0.43 mmol) and TOTU (142 mg, 0.43 mmol) in DMF (3 mL) and the received solution was stirred at ambient temperature for 12 h. The mixture was acidified with trifluoroacetic acid and purified by preparative HPLC. The relevant fractions were lyophilized to give 67 mg (yield: 28%) of the product as a white solid. LC/MS (method E*) (M+H)+: 440.

The racemic product derived from step 2 (35 mg) was separated in its enantiomers by chiral preparative HPLC [column: (S,S) Whelk-O 250×50 mm, eluent: heptane, ethanol and methanol (3:1:1)+0.1% ammonium acetate (isocratic), flow rate: 50 mL/min]. The relevant fractions were lyophilized to give 12 mg (34%) of the pure compound.
LC/MS (method E*) (M+H)+: 440.11 (R$_t$ 1.20 min.)

Example 83

N-(1-{3-Bromo-4-[(piperidine-4-carbonyl)-amino]-
phenyl}-ethyl)-N'-(4-carbamimidoyl-phenyl)-
malonamide*trifluoro-acetic acid salt

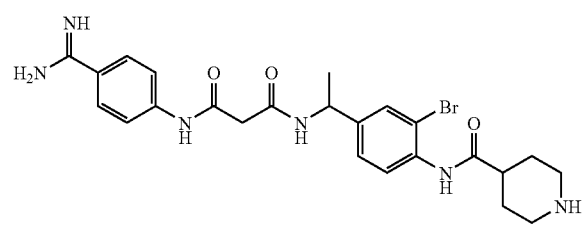

Step 1:

4-(4-Acetyl-2-bromo-phenylcarbamoyl-piperidine-1-
carboxylic acid tert-butyl ester

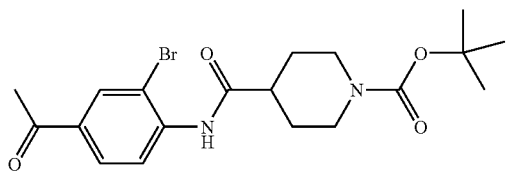

To a solution of the product derived from step 1, example 92 (5.65 g, 24.6 mmol) in DMF (35 ml), were added TOTU (8.62 g, 26.3 mmol), and piperidine-1,4-dicarboxylic acid mono-tert-butyl ester (6.03 g, 28 mmol) and DIPEA (7.0 ml). The reaction mixture was stirred at ambient temperature for 20 h and afterwards evaporated. The residue was dissolved in ethyl acetate (200 ml) and washed with brine (50 ml), and sodium hydrogen carbonate (sat., 50 ml) and dried over sodium sulphate. Evaporation and purification of the crude product by silica gel chromatography using ethyl acetate/heptane gave the desired product (3.72 g, 36%).

Step 2:

4-[4-(1-Amino-ethyl)-2-bromo-phenylcarbamoyl]-
piperidine-1-carboxylic acid tert-butyl ester

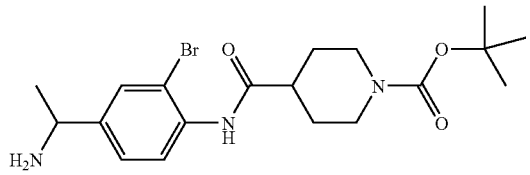

Ammonium acetate (3.17 mg, 41.0 mmol) and sodium cyanoborohydride (260 mg, 4.10 mmol) were added to the product derived from step 2 (1.74 g, 4.1 mmol) in methanol (40 mL). The reaction mixture was stirred for 4 h at 60° C. Then the mixture was quenched by addition of hydrochloric acid (6N) to reach pH=4. Evaporation and purification of the crude product by preparative HPLC and lyophilization of the relevant fractions gave the desired product (710 mg, 41%).

Step 3:

N-(1-{3-Bromo-4-[(piperidine-4-carbonyl)-amino]-
phenyl}-ethyl)-N'-(4-carbamimidoyl-phenyl)-
malonamide*trifluoro-acetic acid salt (Example 83)

To a solution of the product derived from step 2 (122 mg, 226 μmol), N-(4-carbamimidoyl-phenyl)-malonamic acid*trifluoro-acetic acid salt (intermediate 4) (50 mg, 226 μmol) and TOTU (74 mg, 226 μmol) in DMF (1.5 mL) was added DIPEA (40 μL, 30 mg, 226 μmol) and this solution was allowed to stir at ambient temperature for 12 h. The mixture was acidified with trifluoroacetic acid and purified by prep-HPLC. The relevant fractions were lyophilized and the desired product was obtained as a white solid. LC/MS (method E) (M+H)+: 580.00

Example 84

N-(4-Carbamimidoyl-phenyl)-N'-(1-{4-[(piperidine-
4-carbonyl)-amino]-phenyl}-ethyl)-
malonamide*trifluoro-acetic acid salt

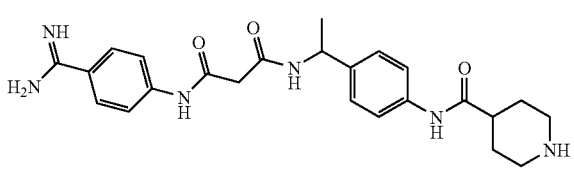

Step 1:

4-(4-Acetyl-phenylcarbamoyl)-piperidine-1-carboxylic acid tert-butyl ester

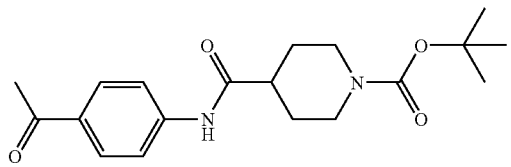

To a solution of 4-aminoacetophenone (6.76 g, 50 mmol) in DMF (250 ml) were added TOTU (16.40 g, 50 mmol), boc-isonipecotic acid (11.46 g, 50 mmol) and DIPEA (8.6 ml, 50 mmol). The reaction mixture was stirred at ambient temperature for 12 h. The solvent was removed in vacuo. The residue was redissolved in ethyl acetate (250 ml) and washed with sat. sodium hydrogen carbonate solution (2×50 ml), hydrochloric acid (1 N, 50 ml) and brine (50 ml). The organic phase was dried over sodium sulfate, evaporated and recrystallized from ethyl acetate. The product was obtained as white crystalline solid (yield: 12.2 g, 70%).

Step 2:

4-[4-Amino-ethyly)-phenylcarbamoyl]-piperidine-1-carboxylic acid tert-butyl ester

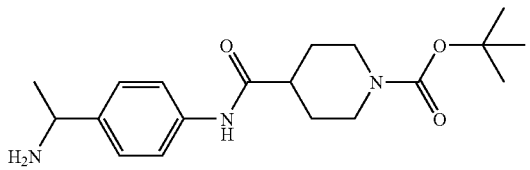

To a solution of the compound yielded from step 1 (5.0 g, 14.43 mmol) in MeOH (100 mL) ammonium acetate (11.12 g, 144 mmol) and sodium cyanoborohydride (955 mg, 14.43 mmol) were added. The reaction mixture was refluxed for 3 h. Then the mixture was quenched by addition of concentrated hydrochloric acid at 0° C. to reach pH=4. Evaporation and purification of the crude product by prep-HPLC leads after lyophilization of the relevant fractions to the desired product (yield: 4.26 g, 64%).

Step 3:

4-(4-{1-[2-(4-Carbamimidoyl-phenylcarbamoyl)-acetylamino]-ethyl}-phenyl-carbamoyl)-piperidine-1-carboxylic acid tert-butyl ester*trifluoro-acetic acid salt To a solution of the product derived from step 2 (90 mg, 0.2 mmol) in DMF (3 ml) TOTU (64 mg, 0.2 mmol), and N-(4-carbamimidoyl-phenyl)-malonamic acid trifluoro-acetic acid salt (intermediate 4) (52 mg, 0.23 mmol) were added. The reaction mixture was stirred at ambient temperature for 12 h. The mixture was evaporated and the residue was purified by preparative HPLC. The relevant fractions were lyophilized to give 42 mg (yield: 32%) of the product as a white solid.

Step 4:

N-(4-Carbamimidoyl-phenyl)-N'-(1-{4-[(piperidine-4-carbonyl)-amino]-phenyl}-ethyl)-malonamide*trifluoro-acetic acid salt (Example 84)

To a suspension of the product derived from step 3 (42 mg, in dichloromethane (1 ml) was added TFA (1.5 ml). The reaction mixture was stirred for 2 h at RT, evaporated and purified by preparative HPLC. Lyophilization of the relevant fractions lead to the product as a white solid (32 mg, yield: 29%).

Example 88

N-(4-Carbamimidoyl-phenyl)-N'-{1-[4-(piperidin-3-yloxy)-3-trifluoromethyl-phenyl]-ethyl}-malonamide*trifluoro-acetic acid salt

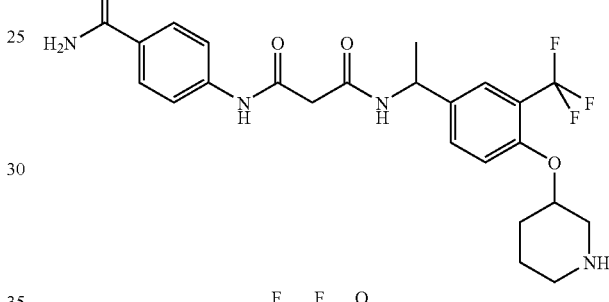

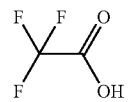

Step 1:

3-(4-Acetyl-2-trifluoromethyl-phenoxy)-piperidine-1-carboxylic acid tert-butyl ester

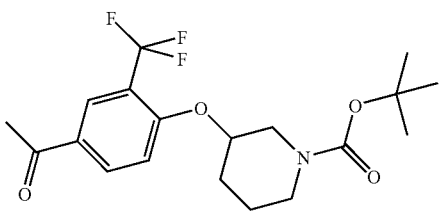

To a suspension of sodium hydride (408 mg, 10.2 mmol) in DMSO (15 ml) was added 1-boc-3-hydroxypiperidine (2.00 g, 10.2 mmol) at 0° C. Stirring was continued for 30 min at 10° C. and 4-fluoro-3-(trifluormethyl)acetophenone (1.40 g, 6.79 mmol) was added dropwise. The reaction mixture was stirred at RT for 1 h and then transferred into water (200 ml) at 0° C. Dichloromethane (300 ml) was added. The organic phase was washed with water (200 ml) and dried over sodium sulfate. Evaporation and purification of the crude product by silica gel chromatography using ethyl acetate/heptane=1:1 gave the desired product (1.80 g, 68%).

Step 2:

3-[4-(1-Amino-ethyl)-2-trifluoromethyl-phenoxy]-piperidine-1-carboxylic acid tert-butyl ester

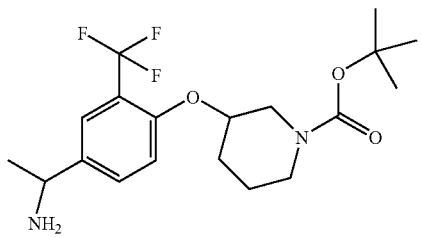

Ammonium acetate (3.00 g, 38.72 mmol) and sodium cyanoborohydride (243 mg, 3.87 mmol) were added to the product derived from step 1 (1.50 g, 3.87 mmol) in methanol (25 mL). The reaction mixture was stirred for 6 h at 60° C. Then the mixture was quenched by addition of hydrochloric acid (6N) to reach pH=4. Evaporation and purification of the crude product by preparative HPLC and lyophilization of the relevant fractions gave the desired product (875 mg, 45%).

Step 3:

3-(4-{1-[2-(4-Carbamimidoyl-phenylcarbamoyl)-acetylamino]-ethyl}-2-trifluoromethyl-phenoxy)-piperidine-1-carboxylic acid tert-butyl ester

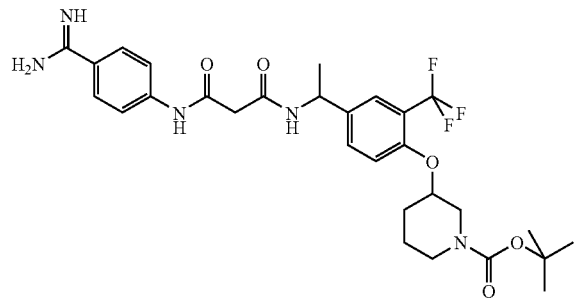

To a solution of the product derived from step 3 (300 mg, 0.6 mmol) in DMF (3 ml) TOTU (196 mg, 0.6 mmol), and N-(4-carbamimidoyl-phenyl)-malonamic acid trifluoro-acetic acid salt (intermediate 4) (200 mg, 0.6 mmol) were added. The reaction mixture was stirred at ambient temperature for 1 h. The mixture was acidified with trifluoroacetic acid and purified by preparative HPLC. The relevant fractions were lyophilized to give 290 mg (yield: 69%) of the product as a white solid.

Step 4:

N-(4-Carbamimidoyl-phenyl)-N'-{1-[4-(piperidin-3-yloxy)-3-trifluoromethyl-phenyl]-ethyl}-malonamide*trifluoro-acetic acid salt (Example 88)

To a solution of the product derived from step 3 in dichloromethane (15 ml) was added TFA (1.5 ml). The reaction mixture was stirred for 1 h at RT, evaporated and purified by preparative HPLC. Lyophilization of the relevant fractions lead to the product as a white solid (147 mg, yield: 90%).

Example 90

N-(4-Carbamimidoyl-phenyl)-N'-[1-(4'-methane-sulfonylamino-biphenyl-3-yl)-ethyl]-malonamide*trifluoro-acetic acid salt

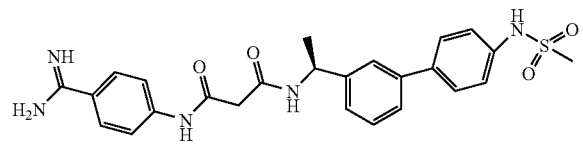

Step 1:

N-[3'-(1-Amino-ethyl)-biphenyl-4-yl]-methane-sulfonamide

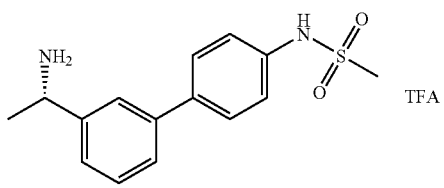

To a solution of (S)-1-(3-bromo-phenyl)-ethylamine (100 mg, 0.50 mmol) in ACN (1.6 ml) were added [(4-methylsulfonyl)aminophenyl]boronic acid (108 mg, 0.50 mmol), sodium carbonate (53 mg, 0.50 mmol), water (0.5 ml) and tetrakis(triphenyl-phosphine)palladium(0). The reaction mixture was heated 30 min at 100° C. using microwaves. The mixture was filtered and purified by preparative HPLC. The relevant fractions were lyophilized to give 110 mg (yield: 54%) of the desired product.

Step 2:

N-(4-Carbamimidoyl-phenyl)-N'-[1-(4'-methane-sulfonylamino-biphenyl-3-yl)-ethyl]-malonamide*trifluoro-acetic acid salt (Example 90)

DIPEA (38 µl, 223 µmol) was added to a solution of the product derived from step 1 (30 mg, 74 µmol), N-(4-carbamimidoyl-phenyl)-malonamic acid*trifluoro-acetic acid salt (intermediate 4) (25 mg, 74 µM µmol) and TOTU (24 mg, 74 µmol) in DMF (2 mL) and the received solution was stirred at ambient temperature for 3 h. The mixture was acidified with trifluoroacetic acid and purified by preparative HPLC. The relevant fractions were lyophilized to give 17 mg (yield: 38%) of the product as a white solid. LC/MS (method F) (M+H)$^+$: 493.18 ($R_t$ 1.32 min.)

Example 92

N-{1-[3-Bromo-4-(morpholine-4-carbonyl)-phenyl]-ethyl}-N'-(4-carbamimidoyl-phenyl)-malonamide*trifluoro-acetic acid salt

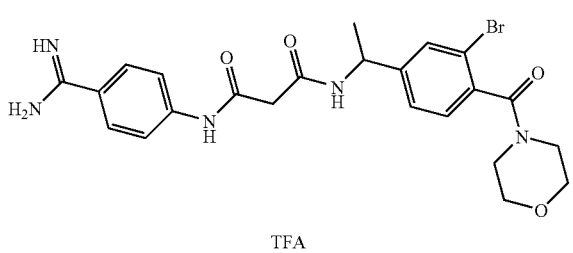

TFA

Step 1:

1-(4-Amino-3-bromo-phenyl)-ethanone

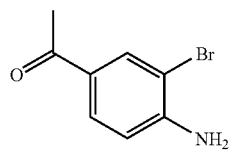

A solution of N-(4-Acetyl-2-bromo-phenyl)-acetamide (10.0 g, 39.05 mmol) in concentrated hydrochloric acid (200 mL) was stirred for 5 h under reflux. The reaction mixture was concentrated under reduced pressure. The residue was treated with a saturated aqueous solution of NaHCO$_3$ (75 mL), extracted with CH$_2$Cl$_2$ (2×70 mL) and dried over Na$_2$SO$_4$. Evaporation leads to the product (8.35 g, 100%) which was used in step 2 without further purification.

Step 2:

4-Acetyl-2-bromo-benzonitrile

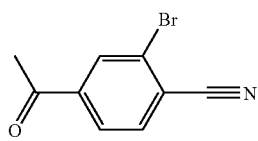

To a solution of the product obtained in step 1 (9.50 g, 44.38 mmol) in acetic acid (160 mL) was added sulfuric acid (95%, 7.4 mL) at 0° C. After stirring for 10 min a solution of NaNO$_2$ (3.06 g, 44.38 mmol) in water (30 mL) was added slowly. Stirring was continued for 30 min. The reaction mixture was added drop wise to a solution of CuCN (3.975 g, 44.38 mmol) and KCN (8.667 g, 133.1 mmol) in water (60 mL). Stirring was continued for 30 min at 0° C. and 2 h at RT. Then the reaction mixture was poured into water (400 mL). Filtration of the resulting suspension gave the desired product as red solid (5.7 g, 57%), which was used in the following step without further purification.

Step 3:

4-Acetyl-2-bromo-benzoic acid

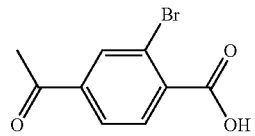

A solution of the product obtained in step 2 (0.5 g, 2.23 mmol) in AcOH (2.5 mL), H$_2$O (2.5 mL) and concentrated H$_2$SO$_4$ (2.5 mL) was refluxed for 5 h. After cooling, the reaction mixture was adjusted with 10 N NaOH to pH=10 and washed with AcOEt. The aqueous layer was acidified with concentrated HCl to pH=1 and then extracted with AcOEt. The organic phase was washed with H$_2$O, dried over Na$_2$SO$_4$ and evaporated under reduced pressure. The crude product was used in the following step without further purification.

Step 4:

1-[3-Bromo-4-(morpholine-4-carbonyl)phenyl]-ethanone

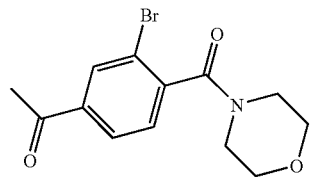

To a solution of the product obtained in step 3 (230 mg, 0.95 mmol) and TOTU (310 mg, 0.95 mmol) in DMF (2 mL) was added morpholine (83 µL, 0.95 mmol) and DIPEA (162 µL, 0.95 mmol). The reaction mixture was stirred for 2 h at RT. Ethyl acetate (20 ml) and water (20 ml) was added, the organic phase was separated and washed with hydrochloric acid (1 M, 20 ml), water (20 ml), brine (2×20 ml) and dried over Na$_2$SO$_4$. After evaporation and flash-chromatography the product was obtained as oil (160 mg, 54%).

Step 5:

[4-(1-Amino-ethyl)-2-bromo-phenyl]-morpholin-4-yl-methanone

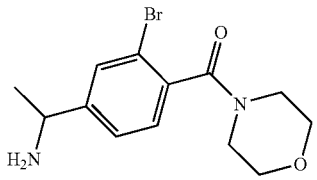

To a solution of the compound yielded from step 4 (160 mg, 0.51 mmol) in MeOH (3 mL) ammonium acetate (395 mg, 5.13 mmol) and sodium cyanoborohydride (32 mg, 0.513 mmol) were added. The reaction mixture was refluxed for 3 h. Then the mixture was quenched by addition of trifluoroacetic acid (pH=2) and evaporated to dryness. Purification of the crude product by prep-HPLC and lyophilization of the relevant fractions leads to the desired product.

Step 6:

N-{1-[3-Bromo-4-(morpholine-4-carbonyl)-phenyl]-ethyl}-N'-(4-carbamimidoyl-phenyl)-malonamide*trifluoro-acetic acid salt To a solution of the product derived from step 5 (30 mg, 70.22 mmol), N-(4-Carbamimidoyl-phenyl)-malonamic acid*trifluoro-acetic acid salt (intermediate 4) (23.5 mg, 70.22 mmol) and TOTU (23 mg, 70.22 mmol) in DMF (1 mL) was added DIPEA (36 μL, 27 mg, 0.21 mmol) and this solution was allowed to stir at ambient temperature for 2 h. The mixture was acidified with trifluoroacetic acid and purified by prep-HPLC. The relevant fractions were lyophilized to give 15 mg (yield: 34%) of the product as a white solid. LC/MS (method E) (M+H)$^+$: 515.12

Example 103

N-(4-Carbamimidoyl-phenyl)-N'-{1-[3-(5-chloro-thiophen-2-yl)-4-(tetrahydro-pyran-4-yloxy)-phenyl]-ethyl}-malonamide; Compound with trifluoro-acetic acid

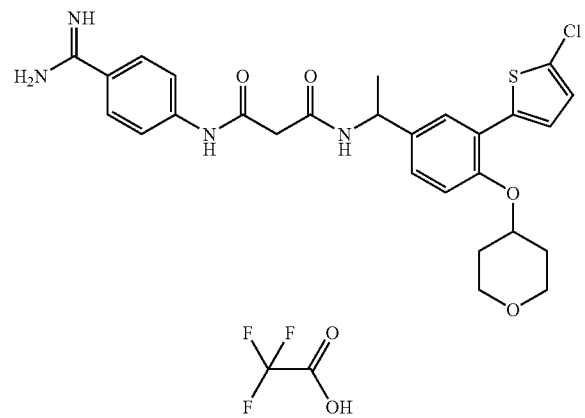

Step 1:

1-[3-(5-Chloro-thiophen-2-yl)-4-fluoro-phenyl]-ethanone

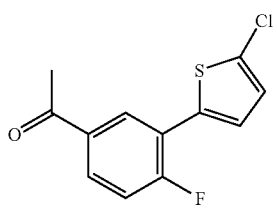

To a solution of 2-fluoro-5-acetylphenylboronic acid (5.00 g, 27.48 mmol) in ACN (80 mL) and H$_2$O (20 mL) were added 2-bromo-5-chlorothiophene (5.43 g, 27.48 mmol), sodium carbonate (2.91 g, 27.48 mmol) and tetrakis(triphenylphosphine)palladium(0) (635 mg, 0.02 mmol). The reaction mixture was refluxed for 3 h. After cooling, ethyl acetate (150 ml) and water (150 ml) were added. The aqueous phase was extracted with ethyl acetate and the combined organic phases were dried over sodium sulfate. Evaporation and purification of the crude product by silica gel chromatography using ethyl acetate/heptane gave the desired product (2.95 g, 42%).

Step 2:

1-[3-(5-Chloro-thiophen-2-yl)-4-(tetrahydro-pyran-4-yloxy)-phenyl]-ethanone

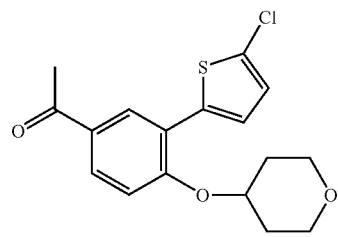

Tetrahydro-pyran-4-ol (1.01 g, 5.01 mmol) was added dropwise at 0° C. to a suspension of sodium hydride (200 mg, 5.01 mmol) in DMSO (10 ml). After stirring for 30 min at 10° C., a solution of the product obtained from step 1 (850 mg, 3.34 mmol) in DMSO (2 ml) was added dropwise and stirring was continued for 1 h at RT. The reaction was quenched with ice/water (50 ml). Ethyl acetate (50 ml) was added and the aqueous phase was extrated with ethyl acetate (2×30 ml). The combined organic phases were washed with brine (2×50 ml), dried over sodium sulphate, filtered, and evaporated. The product was obtained in quantitative yield and used in the next step without further purification.

Step 3:

1-[3-(5-Chloro-thiophen-2-yl)-4-(tetrahydro-pyran-4-yloxy)-phenyl]-ethylamine

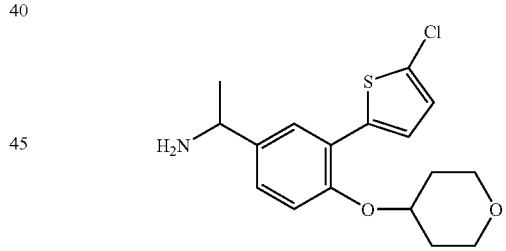

To a solution of the compound yielded from step 2 (1.20 g, 3.56 mmol) in MeOH (20 mL) ammonium acetate (2.75 g, 35.63 mmol) and sodium cyanoborohydride (224 mg, 3.56 mmol) were added. The reaction mixture was refluxed for 6 h. Then the cooled mixture was adjusted with trifluoroacetic acid to pH=2 and evaporated to dryness. Purification of the crude product by prep-HPLC and lyophilization of the relevant fractions lead to the desired product (420 mg, 26%).

Step 4:

N-(4-Carbamimidoyl-phenyl)-N'-{1-[3-(5-chloro-thiophen-2-yl)-4-(tetrahydro-pyran-4-yloxy)-phenyl]-ethyl}-malonamide; Compound with trifluoro-acetic acid To a solution of the product derived from step 3 (420 mg, 0.93 mmol), N-(4-carbamimidoyl-phenyl)-malonamic acid*trifluoro-acetic acid salt (intermediate 4) (312 mg, 0.93 mmol) and TOTU (305 mg, 0.93 mmol) in DMF (8 mL) was added DIPEA (0.5 ml, 2.79 mmol) and this solution was allowed to stir at ambient temperature for 2 h. The mixture was acidified with trifluoroacetic acid and purified by prep-HPLC. The relevant fractions were lyophilized to give 232 mg (yield: 38%) of the product as a white solid. LC/MS (method E) (M+H)$^+$: 540.16

Example 106

N-(4-Carbamimidoyl-phenyl)-N'-{1-[3-(5-chloro-thiophen-2-yl)-4-(morpholine-4-sulfonyl)-phenyl]-ethyl}-malonamide*trifluoro-acetic acid salt

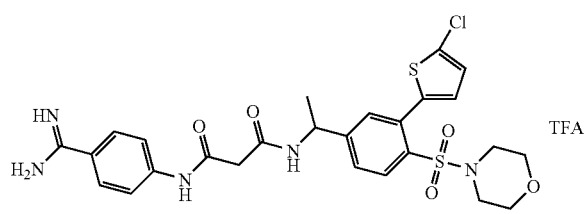

Step 1:

4-(2,4-Dibromo-benzenesulfonyl)-morpholine

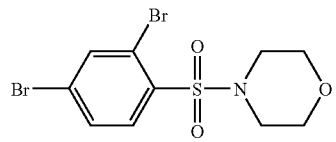

To a solution of morpholine (1.6 ml, 17.9 mmol) and triethylamine (2.1 ml, 15.5 mmol) in tetrahydrofurane (40 mL) was added a solution of dibromo-benzenesulfonyl chloride (5.00 g, 15.0 mmol) in THF (10 ml). The reaction mixture was stirred for 2 h at RT. Then, ethyl acetate (80 ml) was added. The organic phase was separated and washed with water (20 ml), hydrochloric acid (1 M, 20 ml) and brine (20 ml) and dried over Na$_2$SO$_4$. After evaporation the product was obtained (5.95 g, 100%) and used in the next step without further purification.

Step 2:

1-[3-Bromo-4-(morpholine-4-sulfonyl)phenyl]-ethanone

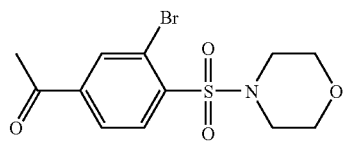

To a solution of the product obtained in step 1 (4.8 g, 12.5 mmol) in ACN (15 ml) was added CuI (119 mg, 0.62 mmol), PdCl$_2$(PPh$_3$)$_2$ and 1-(ethoxyvinyl)tributyl-stannane (5.4 g, 14.95 mmol). The mixture was refluxed for 3 h. After cooling, the reaction mixture was acidified with 1 N HCl (7 ml) and stirred for 20 min. The reaction mixture was neutralized with saturated aqueous NaHCO$_3$ and extracted with AcOEt. The organic phase was dried over Na$_2$SO$_4$ and evaporated. Purification of the crude product by silica gel chromatography using ethyl acetate/n-heptane gave the desired product (2.95 g, 68%).

Step 3:

1-[3-(5-Chloro-thiophen-2-yl)-4-(morpholine-4-sulfonyl)-phenyl]-ethanone

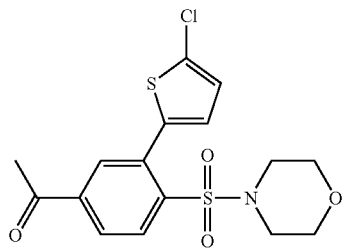

The product of step 2 was suspended in ACN (16 mL) and H$_2$O (4 mL). Na$_2$CO$_3$ (578 mg, 5.46 mmol), thiophene-2-chloro-5-boronic acid (887 mg, 5.46 mmol) and Pd(PPh$_3$)$_4$ (630 mg, 0.55 mmol) was added. The reaction mixture was refluxed for 2 h. After cooling, AcOEt and H$_2$O were added. The organic phase was washed with saturated aqueous NH$_4$Cl and brine and dried over Na$_2$SO$_4$. After evaporation the product was obtained (2.2 g), which was used in the following step without further purification.

Step 4:

1-[3-(5-Chloro-thiophen-2-yl)-4-(morpholine-4-sulfonyl)-phenyl]-ethylamine

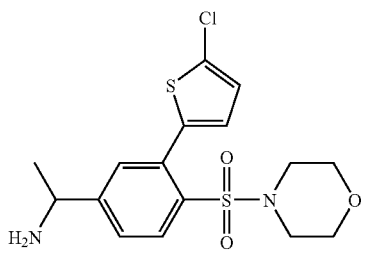

To a solution of the compound yielded from step 3 (2.2 g, 5.7 mmol) in MeOH (30 mL) ammonium acetate (4.39 g, 57.0 mmol) and sodium cyanoborohydride (358 mg, 5.7 mmol) were added. The reaction mixture was refluxed for 4 h. After that the mixture was acidified with trifluoroacetic acid to pH=2 and then evaporated to dryness. Purification of the crude product by prep-HPLC and lyophilization of the relevant fractions gave the desired product (0.96g, 34%).

Step 5:

N-(4-Carbamimidoyl-phenyl)-N'—{(S)-1-[4-(morpholine-4-sulfonyl)-3-trifluoromethyl-henyl]-ethyl}-malonamide*trifluoro-acetic acid salt To a solution of the product derived from step 4 (0.96 g, 1.92 mmol), N-(4-Carbamimidoyl-phenyl)-malonamic acid*trifluoro-acetic acid salt (intermediate 4) (0.64 g, 1.92 mmol) and TOTU (0.63 g, 1.92 mmol) in DMF (18 mL) was added DIPEA (1.0 mL, 5.75 mmol) and the solution was stirred at ambient temperature for 12 h. The mixture was acidified with trifluoroacetic acid and purified by prep-HPLC. The relevant fractions were lyophilized to give 0.62 g (yield: 45%) of the product as a white solid.

Example 125

N-(4-Carbamimidoyl-phenyl)-N'-{1-[4-(morpholine-4-sulfonyl)-3-thiazol-2-yl-phenyl]-ethyl}-malonamide*trifluoro-acetic acid salt

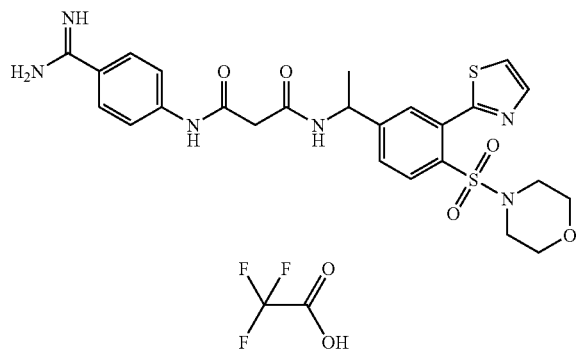

Step 1:

1-[3-Bromo-4-(morpholine-4-sulfonyl)phenyl]-ethylamine

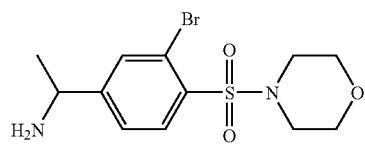

Ammonium acetate (555 mg, 7.20 mmol) and sodium cyanoborohydride (45 mg, 0.72 mmol) were added to a solution of the product derived from step 2, example 106 (250 mg, 0.72 mmol) in methanol (4 mL). The reaction mixture was stirred for 3 h at 60° C. Then the mixture was quenched by addition of hydrochloric acid (6N) to reach pH=2. Evaporation and purification of the crude product by preparative HPLC and lyophilization of the relevant fractions gave the desired product (120 mg, 48%).

Step 2:

1-[4-(Morpholine-4-sulfonyl)-3-thiazol-2-yl-phenyl]-ethylamine

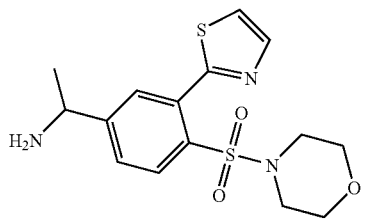

To a solution of the amine obtained in step 1 (100 mg, 286 µmol) in THF (0.3 ml) were added sodium carbonate (30 mg, 286 µM), bis(triphenylphosphine)palladium(II) chloride (20 mg, 29 µmol) and 2-thiatolylzinc bromide (1.145 ml, 573 µmol). The suspension was heated for 90 min at 120° C. using microwaves. The reaction mixture was cooled to RT and dichloromethane (20 ml) was added. The organic phase was washed with hydrogen chloride (2N, 20 ml) and the aqueous phase was adjusted to pH=11. The aqueous phase was extracted with dichloromethane (2×20 ml). The combined organic phases were dried over sodium sulphate and evaporated. The desired amine was obtained (Yield: 60 mg, 59%) and used in the following reaction without further purification.

Step 3:

N-(4-Carbamimidoyl-phenyl)-N'-{1-[4-(morpholine-4-sulfonyl)-3-thiazol-2-yl-phenyl]-ethyl}-malonamide*trifluoro-acetic acid salt (Example 125)

To a solution of the product derived from step 3 (60 mg, 0.17 mmol), N-(4-Carbamimidoyl-phenyl)-malonamic acid*trifluoro-acetic acid salt (intermediate 4) (57 mg, 0.17 mmol) and TOTU (56 g, 0.17 mmol) in DMF (1.5 mL) was added DIPEA (58 µL, 0.34 mmol) and the solution was stirred at ambient temperature for 10 h. The mixture was acidified with trifluoroacetic acid and purified by prep-HPLC. The relevant fractions were lyophilized to give the product as a white solid.

The following Examples were prepared in analogy as described above.

| Example No | Structural Formula | Rt (from LC/MS) | Mass (from LC/MS) | LC/MS Method |
|---|---|---|---|---|
| 1 | | 0.94 | 540.15 | D |

-continued

| Example No | Structural Formula | Rt (from LC/MS) | Mass (from LC/MS) | LC/MS Method |
|---|---|---|---|---|
| 2 | | 1.18 | 524.11 | A |
| 3 | | 0.994 | 533 | A |
| 4 | | 0.951 | 519 | A |
| 5 | | 0.88 | 417.15 | E |

-continued
| Example No | Structural Formula | Rt (from LC/MS) | Mass (from LC/MS) | LC/MS Method |
|---|---|---|---|---|
| 6 | 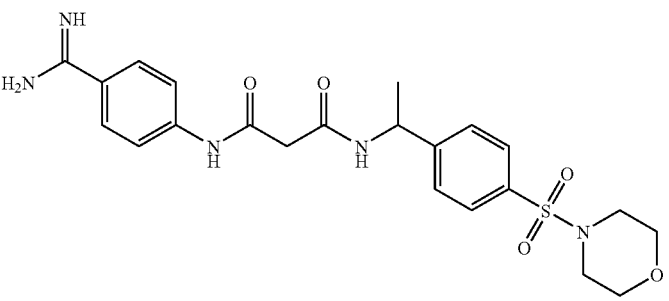 | 1.05 | 473.17 | E |
| 7 | 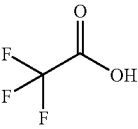 | 0.951 | 520 | A |
| 8 | 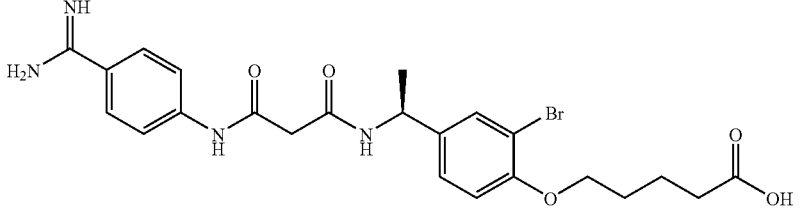 | 0.943 | 489 | A |

-continued
| Example No | Structural Formula | Rt (from LC/MS) | Mass (from LC/MS) | LC/MS Method |
|---|---|---|---|---|
| 9 | 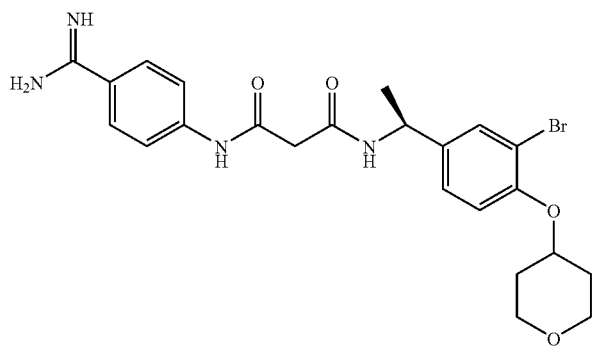 | 0.97 | 503 | A |
| 10 | 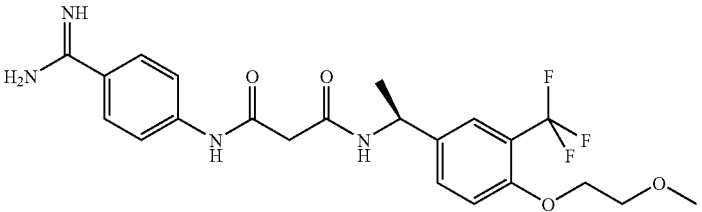 | 1.047 | 467.3 | A |
| 11 | 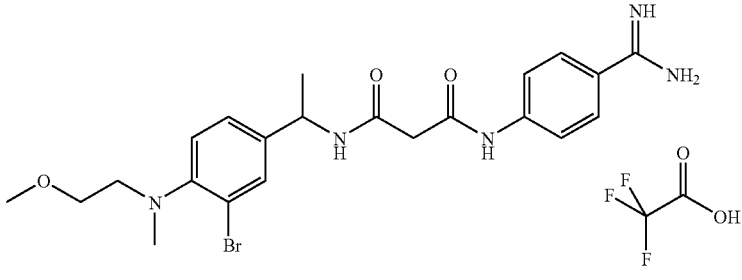 | 0.93 | 489.14 | A |
| 12 | 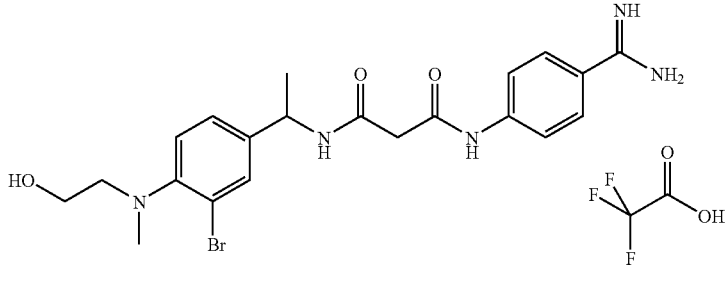 | 0.76 | 475.12 | A |

-continued

| Example No | Structural Formula | Rt (from LC/MS) | Mass (from LC/MS) | LC/MS Method |
|---|---|---|---|---|
| 13 | | 1.22 | 465.2 | A |
| 14 | | 1.03 | 465.2 | A |
| 15 | | 1.04 | 451.18 | A |
| 16 | | 0.736 | 534 | A |

| Example No | Structural Formula | Rt (from LC/MS) | Mass (from LC/MS) | LC/MS Method |
|---|---|---|---|---|
| 17 | 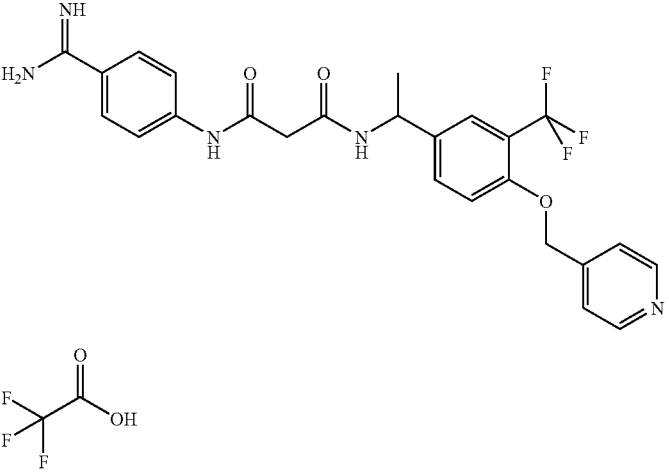 | 0.823 | 500.3 | A |
| 18 | 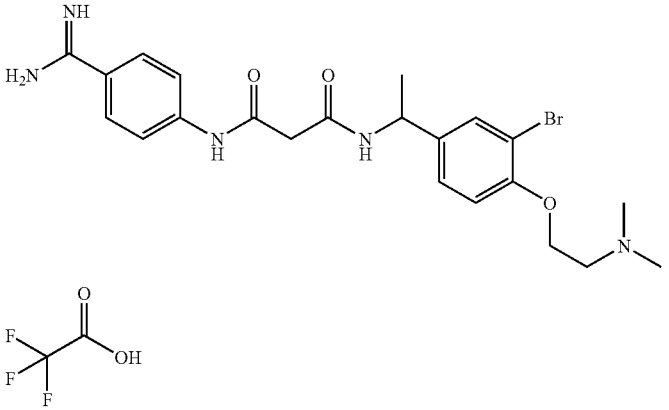 | 0.713 | 490 | A |
| 19 | 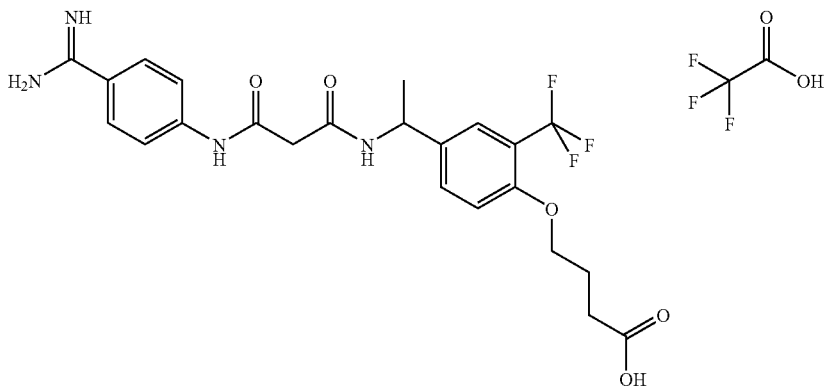 | 0.981 | 495.2 | A |

-continued

| Example No | Structural Formula | Rt (from LC/MS) | Mass (from LC/MS) | LC/MS Method |
|---|---|---|---|---|
| 20 | | 1.050 | 493.2 | A |
| 21 | | 0.77 | 480.2 | A |
| 22 | | 1.054 | 493.2 | A |

-continued

| Example No | Structural Formula | Rt (from LC/MS) | Mass (from LC/MS) | LC/MS Method |
|---|---|---|---|---|
| 23 | | 0.791 | 492.2 | A |
| 24 | | 1.137 | 495.2 | A |
| 25 | | 1.094 | 481.2 | A |

-continued

| Example No | Structural Formula | Rt (from LC/MS) | Mass (from LC/MS) | LC/MS Method |
|---|---|---|---|---|
| 26 | | 0.862 | 453.2 | A |
| 27 | | 0.80 | 490.15 | D |
| 28 | | 1.23 | 541.16 | E |
| 29 | | 1.36 | 442.14 | F |
| 30 | | 1.24 | 479.21 | A |

-continued

| Example No | Structural Formula | Rt (from LC/MS) | Mass (from LC/MS) | LC/MS Method |
|---|---|---|---|---|
| 31 | | 1.262 | 519.0 | A |
| 32 | | 0.823 | 500.3 | A |
| 33 | | 0.876 | 509.9 | A |

-continued
| Example No | Structural Formula | Rt (from LC/MS) | Mass (from LC/MS) | LC/MS Method |
|---|---|---|---|---|
| 34 | 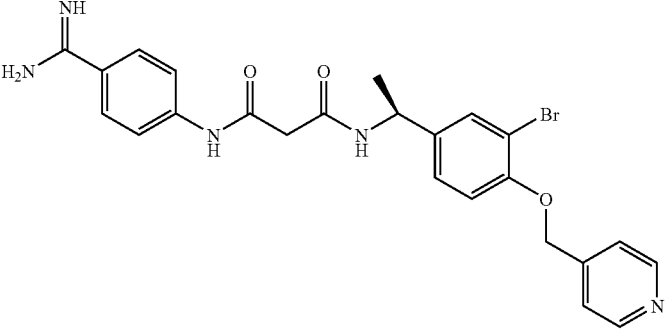 | 0.876 | 509.9 | A |
| 35 | 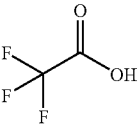 | 0.884 | 548.2 | A |
| 36 | 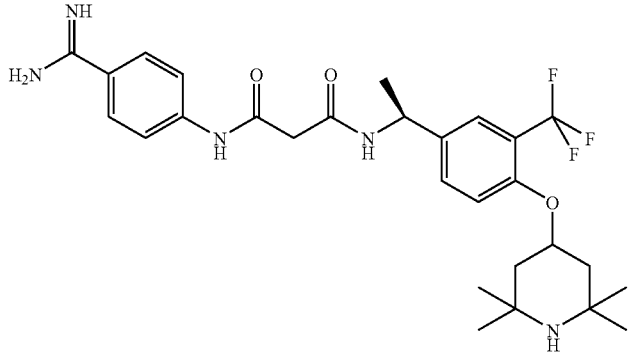 | 1.058 | 517 | A |

-continued

| Example No | Structural Formula | Rt (from LC/MS) | Mass (from LC/MS) | LC/MS Method |
|---|---|---|---|---|
| 37 | | 0.839 | 516.1 | A |
| 38 | | 0.794 | 502.0 | A |
| 39 | CHIRAL | 1.23 | 541.16 | E* |

| Example No | Structural Formula | Rt (from LC/MS) | Mass (from LC/MS) | LC/MS Method |
|---|---|---|---|---|
| 40 | CHIRAL | 1.09 | 507.13 | E* |
| 41 | | 1.077 | 493.2 | A |
| 42 | | 1.050 | 493.1 | A |

| Example No | Structural Formula | Rt (from LC/MS) | Mass (from LC/MS) | LC/MS Method |
|---|---|---|---|---|
| 43 | | 1.124 | 507.2 | A |
| 44 | | 1.066 | 534.2 | A |
| 45 | | 1.127 | 489.2 | A |

-continued

| Example No | Structural Formula | Rt (from LC/MS) | Mass (from LC/MS) | LC/MS Method |
|---|---|---|---|---|
| 46 | | 0.952 | 534.1 | A |
| 47 | | 0.758 | 542.1 | A |
| 48 | | 0.815 | 528.2 | A |

-continued
| Example No | Structural Formula | Rt (from LC/MS) | Mass (from LC/MS) | LC/MS Method |
|---|---|---|---|---|
| 49 | 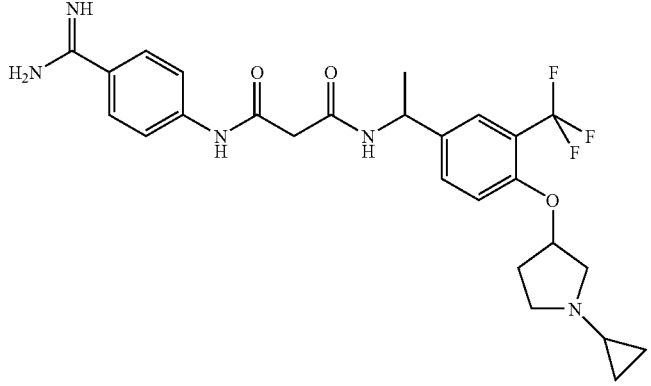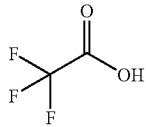 | 0.876 | 518.2 | A |
| 50 | 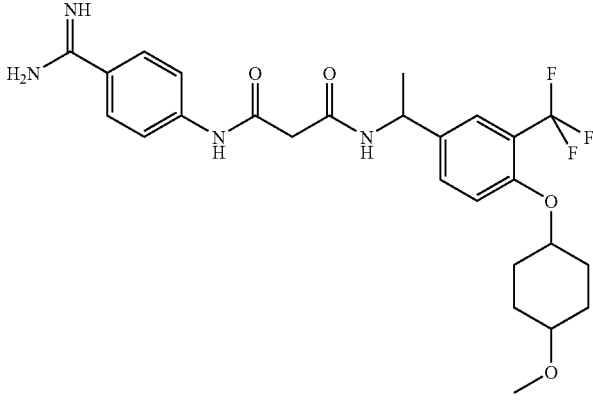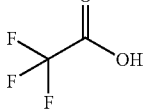 | 1.116 | 521.2 | A |

| Example No | Structural Formula | Rt (from LC/MS) | Mass (from LC/MS) | LC/MS Method |
|---|---|---|---|---|
| 51 | | 1.023 | 481.2 | A |
| 52 | | 1.094 | 499.1 | A |
| 53 | | 1.121 | 501.1 | A |

-continued
| Example No | Structural Formula | Rt (from LC/MS) | Mass (from LC/MS) | LC/MS Method |
|---|---|---|---|---|
| 54 | 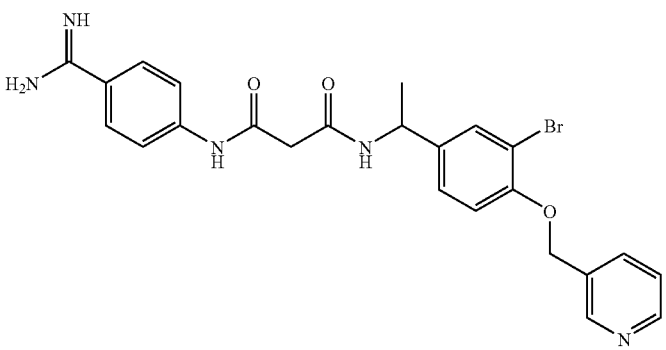 | 0.774 | 510 | A |
| 55 | 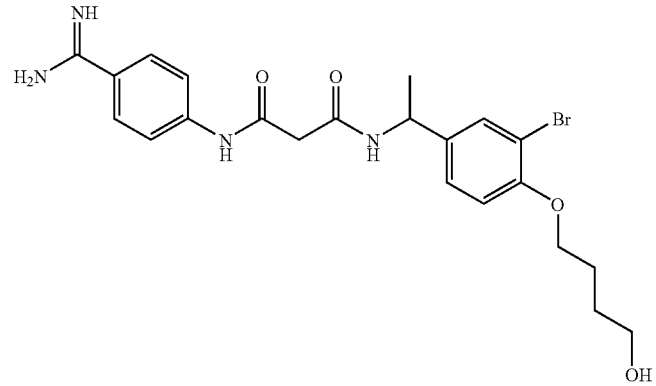 | 0.916 | 491 | A |
| 56 | 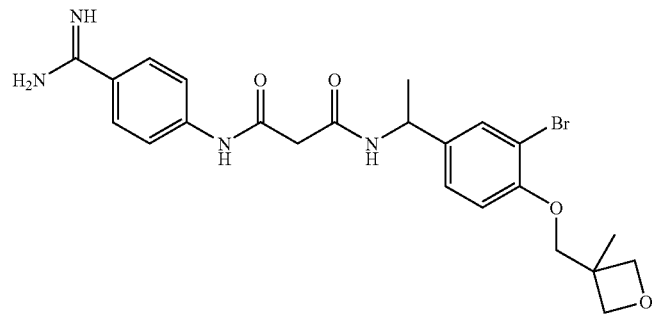 | 0.992 | 503 | A |

-continued
| Example No | Structural Formula | Rt (from LC/MS) | Mass (from LC/MS) | LC/MS Method |
|---|---|---|---|---|
| 57 | 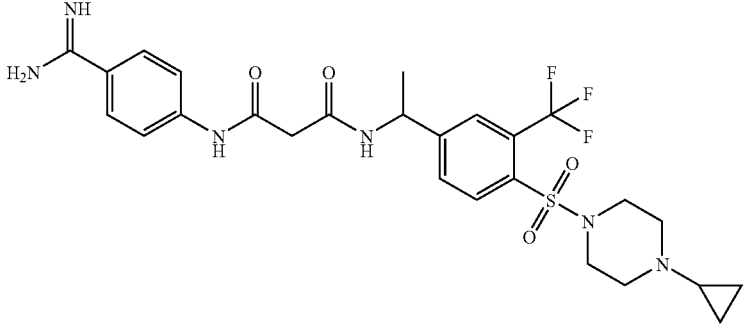 | 0.99 | 580.21 | F |
| 58 | CHIRAL 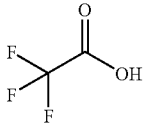 | 1.40 | 440.15 | F* |
| 59 | 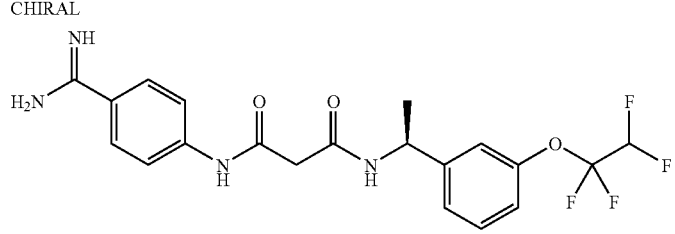 | 0.889 | 680.2 | A |

-continued
| Example No | Structural Formula | Rt (from LC/MS) | Mass (from LC/MS) | LC/MS Method |
|---|---|---|---|---|
| 60 | 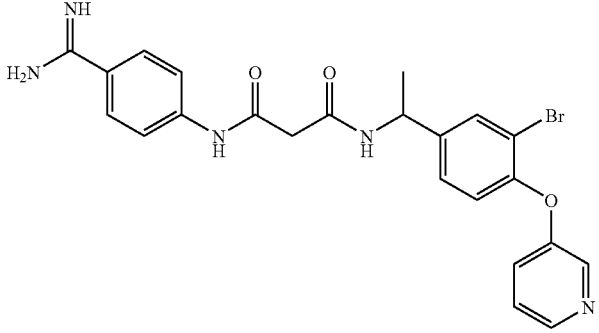 | 0.820 | 496.1 | A |
| 61 | 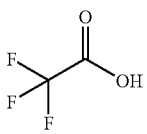 | 0.935 | 544.1 | A |
| 62 | CHIRAL 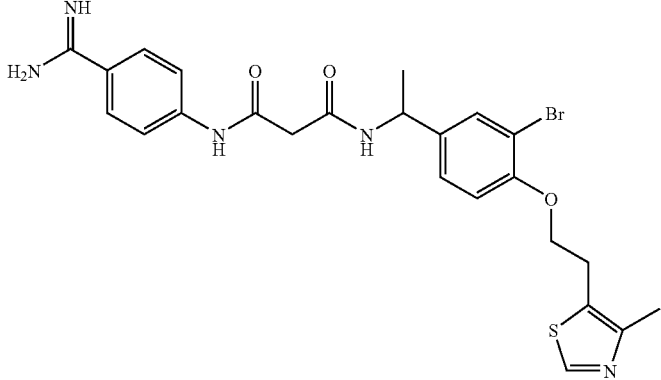 | 0.99 | 580.21 | F* |

-continued
| Example No | Structural Formula | Rt (from LC/MS) | Mass (from LC/MS) | LC/MS Method |
|---|---|---|---|---|
| 63 | 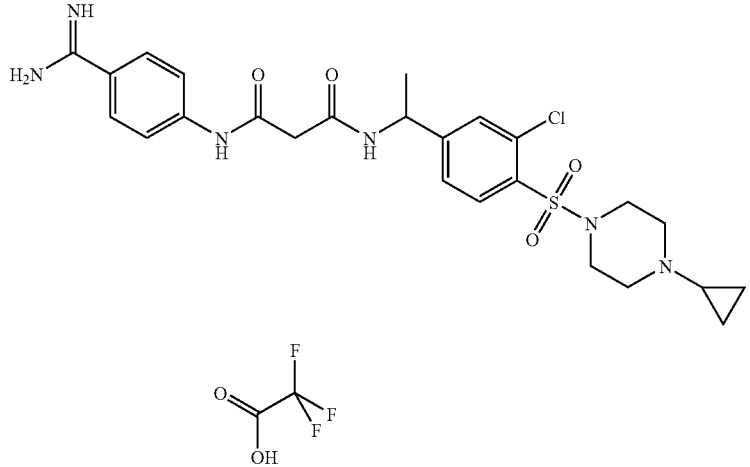 | 0.88 | 546.18 | F |
| 64 | 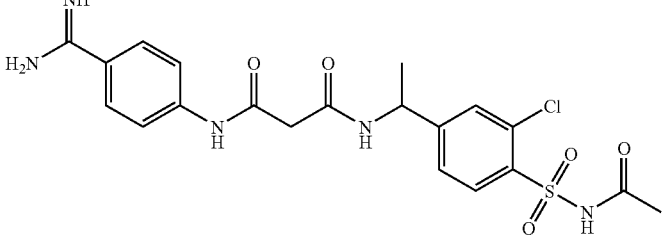 | 0.93 | 479.1 | F |
| 65 | 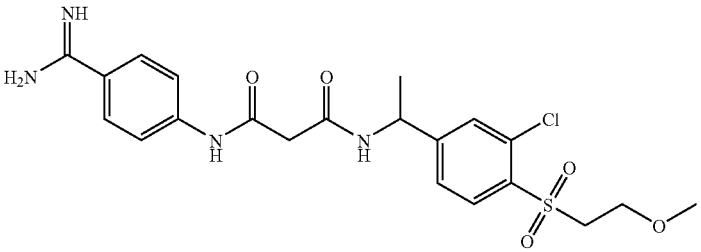 | 1.06 | 480.12 | F |

| Example No | Structural Formula | Rt (from LC/MS) | Mass (from LC/MS) | LC/MS Method |
|---|---|---|---|---|
| 66 | | 1.09 | 506.14 | F |
| 67 | | 0.97 | 513.12 | E |
| 68 | | 1.43 | 539.18 | E |

| Example No | Structural Formula | | Rt (from LC/MS) | Mass (from LC/MS) | LC/MS Method |
|---|---|---|---|---|---|
| 69 | 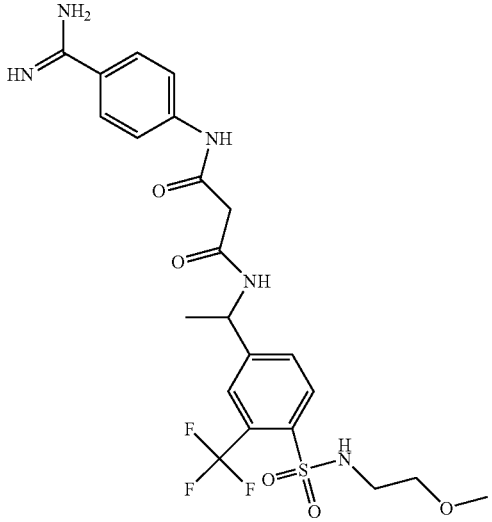 | | 1.11 | 529.16 | E |
| 70 | 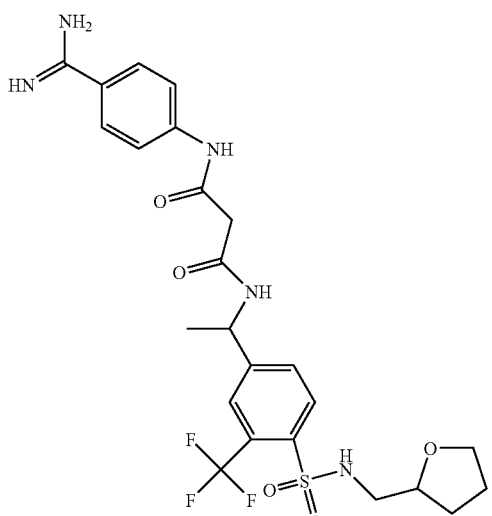 | | 1.27 | 555.18 | E |
| 71 | 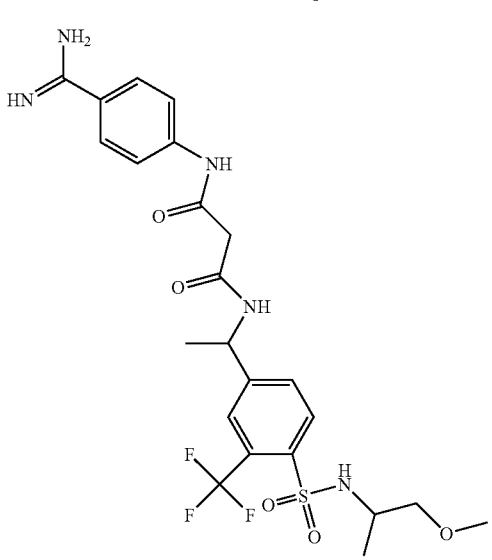 | | 1.2 | 543.18 | E |

-continued
| Example No | Structural Formula | Rt (from LC/MS) | Mass (from LC/MS) | LC/MS Method |
|---|---|---|---|---|
| 72 | 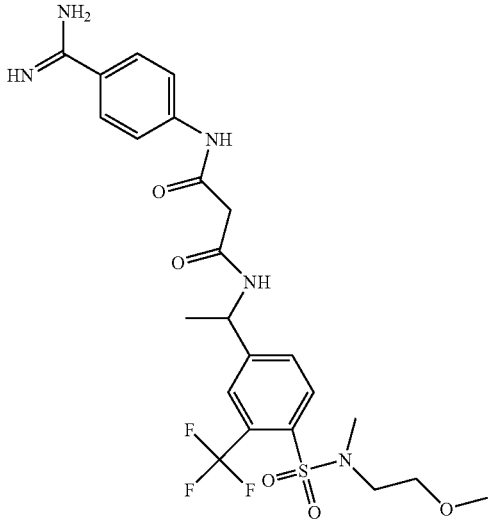 | 1.23 | 543.18 | E |
| 73 | 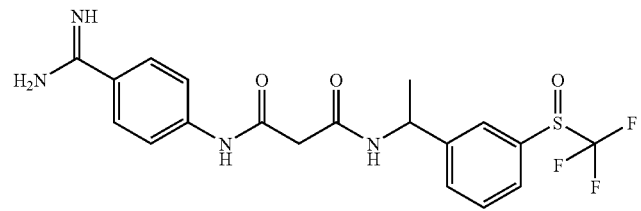 | 1.2 | 440.11 | E |
| 74 | 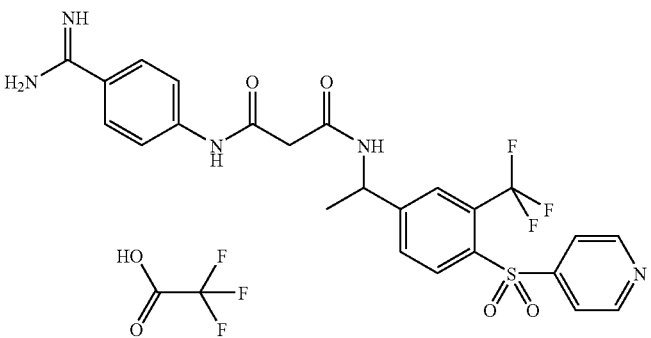 | 1.02 | 533.13 | E |

-continued

| Example No | Structural Formula | Rt (from LC/MS) | Mass (from LC/MS) | LC/MS Method |
|---|---|---|---|---|
| 75 | CHIRAL | 1.11 | 529.16 | E* |
| 76 | CHIRAL | 1.23 | 543.18 | E* |
| 77 | CHIRAL | 1.20 | 440.11 | E* |

-continued
| Example No | Structural Formula | Rt (from LC/MS) | Mass (from LC/MS) | LC/MS Method |
|---|---|---|---|---|
| 78 | CHIRAL 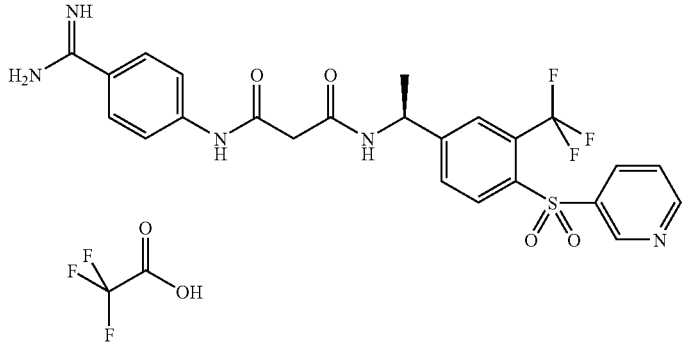 | 0.93 | 533.13 | E* |
| 79 | CHIRAL 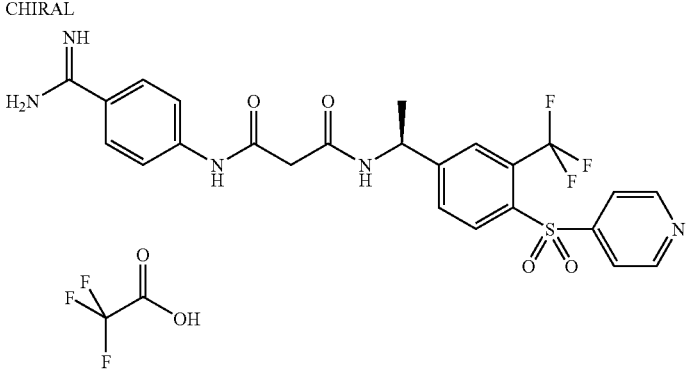 | 1.02 | 533.13 | E* |
| 80 | 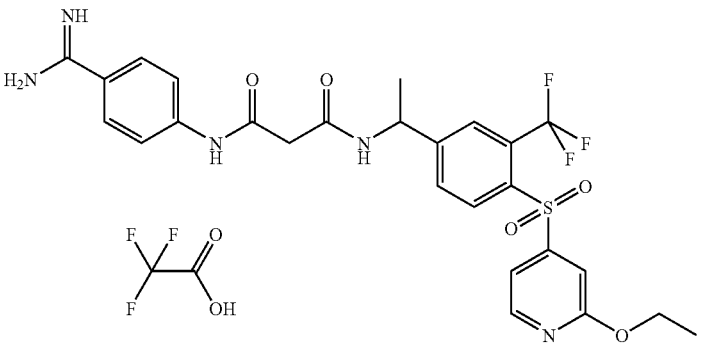 | 1.37 | 577.16 | E |
| 81 | 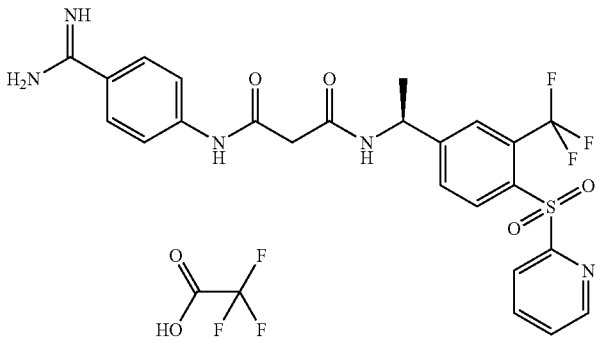 | 5.0 | 533.13 | L |

| Example No | Structural Formula | Rt (from LC/MS) | Mass (from LC/MS) | LC/MS Method |
|---|---|---|---|---|
| 82 | 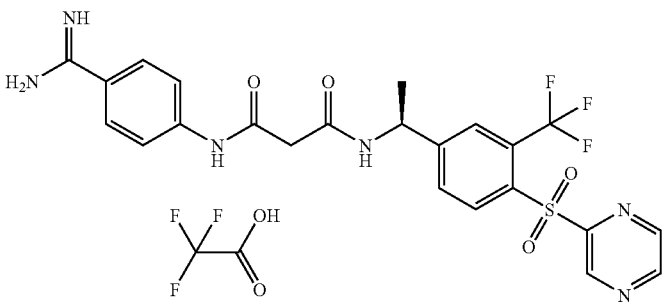 | 1.05 | 534.13 | E* |
| 83 | 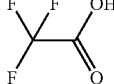 | 0.96 | 528.00 | E |
| 84 | 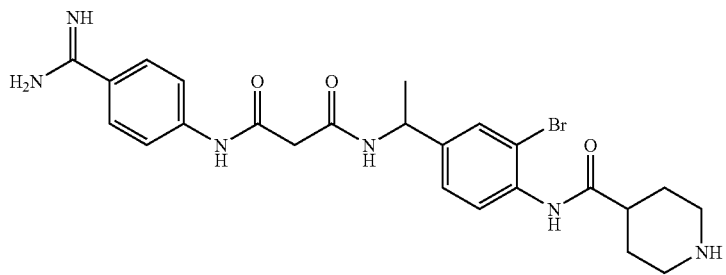 | 0.18 | 450.24 | E |

| Example No | Structural Formula | Rt (from LC/MS) | Mass (from LC/MS) | LC/MS Method |
|---|---|---|---|---|
| 85 | | 1.09 | 507.13 | E |
| 86 | | 0.93 | 533.13 | E |
| 87 | | 1.05 | 534.13 | E |
| 88 | | 0.94 | 491.21 | F |

-continued
| Example No | Structural Formula | Rt (from LC/MS) | Mass (from LC/MS) | LC/MS Method |
|---|---|---|---|---|
| 89 | 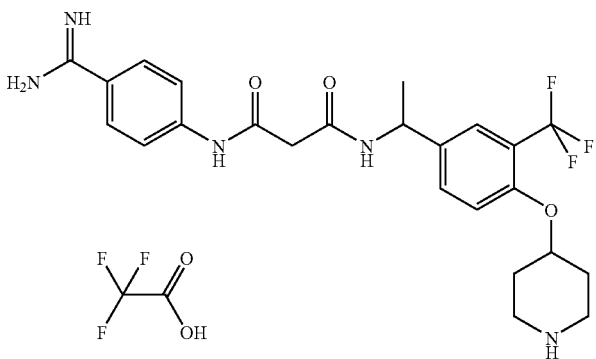 | 0.96 | 491.21 | F |
| 90 | 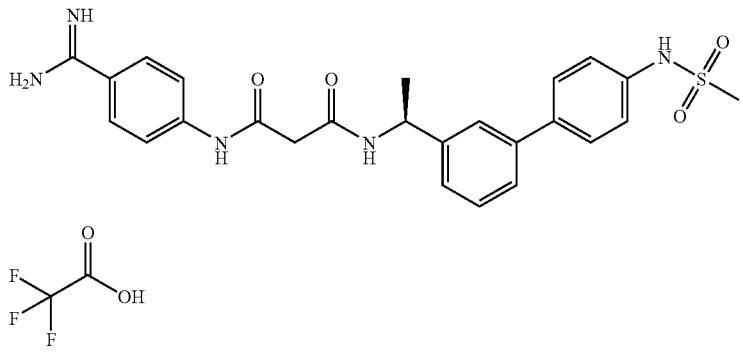 | 1.32 | 493.18 | F |
| 91 | 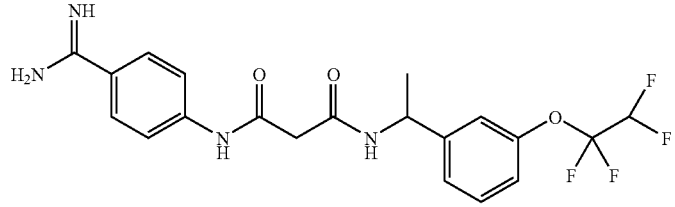 | 1.40 | 440.15 | F |
| 92 | 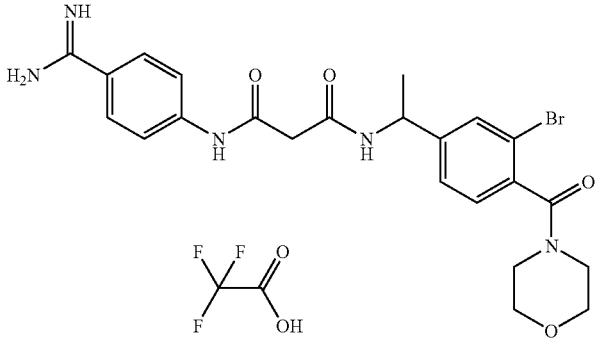 | 1.01 | 515.12 | E |

-continued
| Example No | Structural Formula | Rt (from LC/MS) | Mass (from LC/MS) | LC/MS Method |
|---|---|---|---|---|
| 93 | 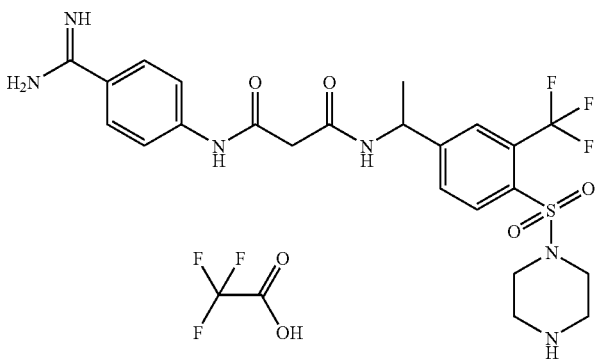 | 0.99 | 540.18 | E |
| 94 | 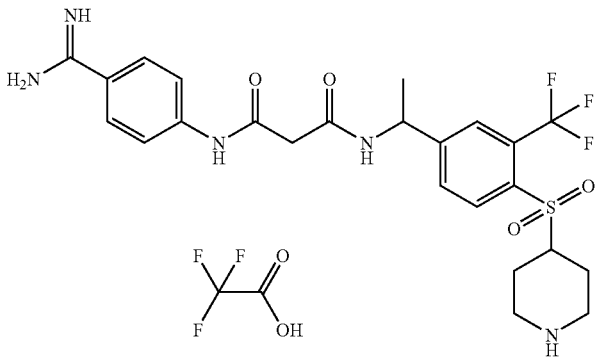 | 0.85 | 539.18 | E |
| 95 | 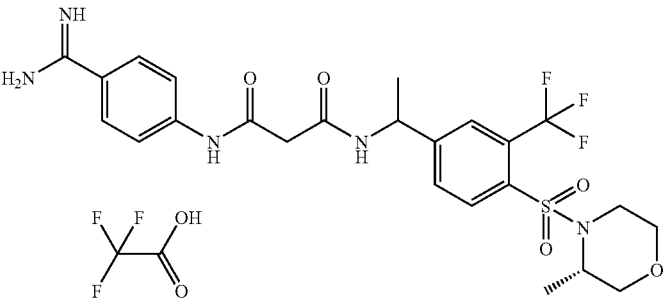 | 1.19 | 555.18 | E |
| 96 | 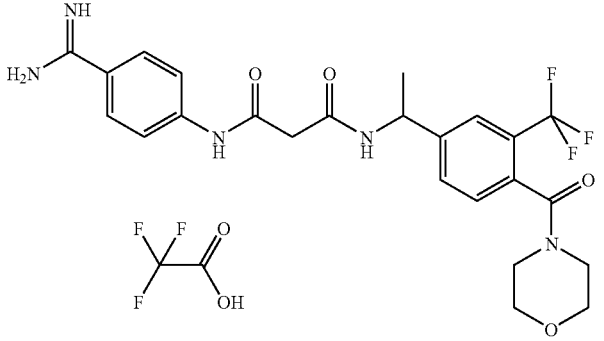 | 1.21 | 505.19 | E |

-continued
| Example No | Structural Formula | Rt (from LC/MS) | Mass (from LC/MS) | LC/MS Method |
|---|---|---|---|---|
| 97 | 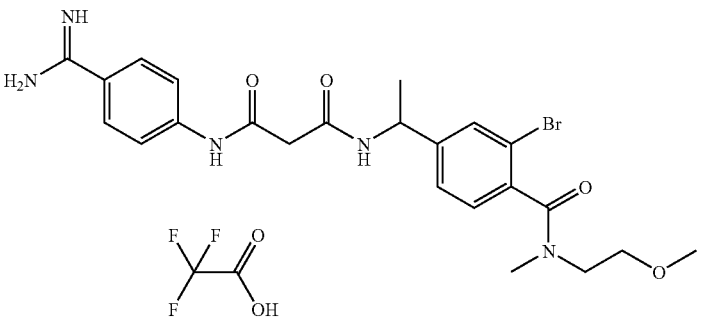 | 1.06 | 517.13 | E |
| 98 | 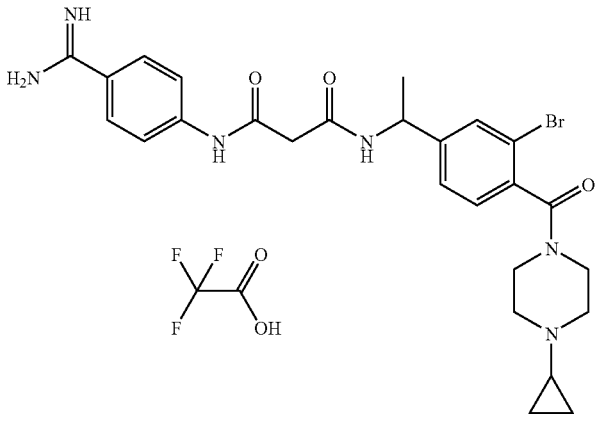 | 0.77 | 554.16 | E |
| 99 | 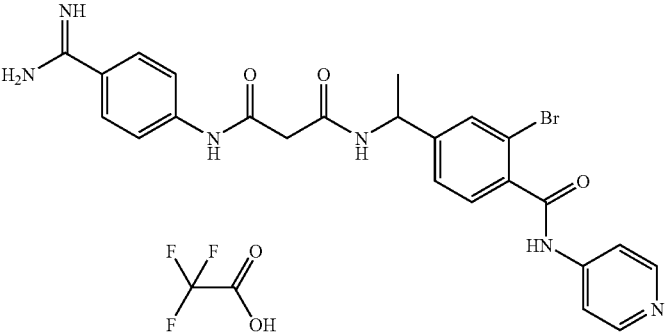 | 0.82 | 522.1 | E |
| 100 | 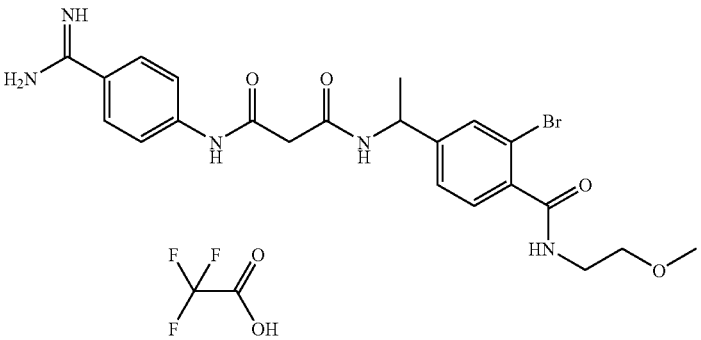 | 0.87 | 503.12 | E |

-continued
| Example No | Structural Formula | Rt (from LC/MS) | Mass (from LC/MS) | LC/MS Method |
|---|---|---|---|---|
| 101 | 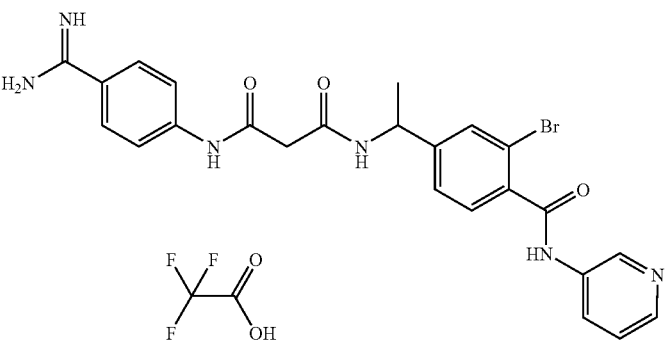 | 0.81 | 522.1 | E |
| 102 | 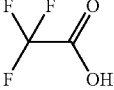 | 0.97 | 529.13 | E |
| 103 | 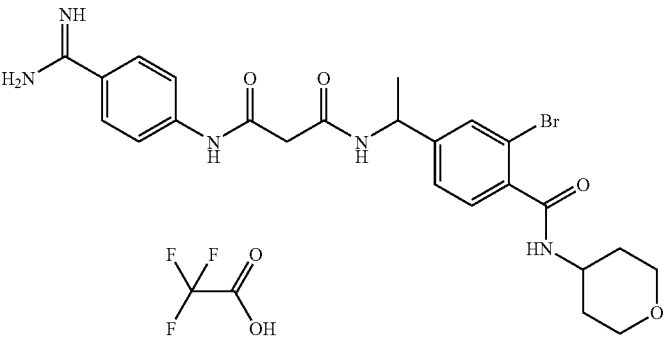 | 1.40 | 540.16 | E |

| Example No | Structural Formula | Rt (from LC/MS) | Mass (from LC/MS) | LC/MS Method |
|---|---|---|---|---|
| 104 | 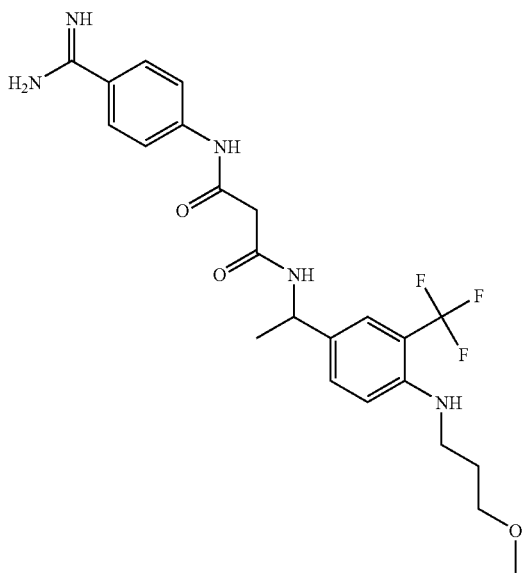 | 1.30 | 480.22 | A |
| 105 | 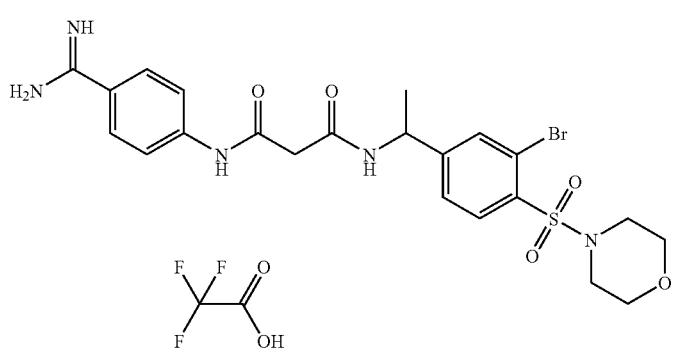 | 1.15 | 551.08 | E |
| 106 | 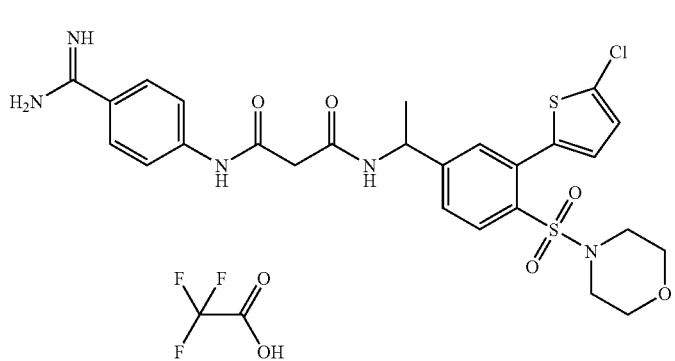 | 1.34 | 589.12 | E |

-continued
| Example No | Structural Formula | Rt (from LC/MS) | Mass (from LC/MS) | LC/MS Method |
|---|---|---|---|---|
| 107 | 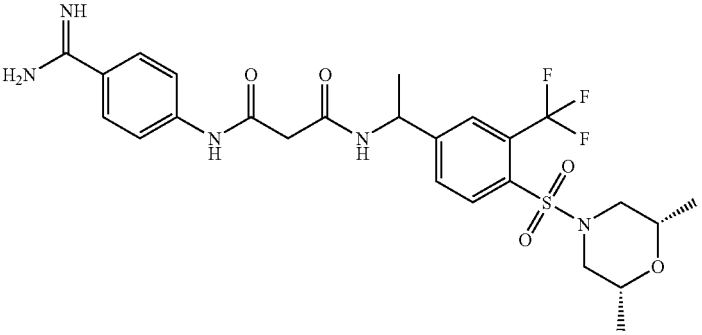 | 1.28 | 569.19 | E |
| 108 | 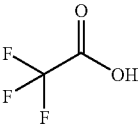 | 1.08 | 555.18 | E |
| 109 | 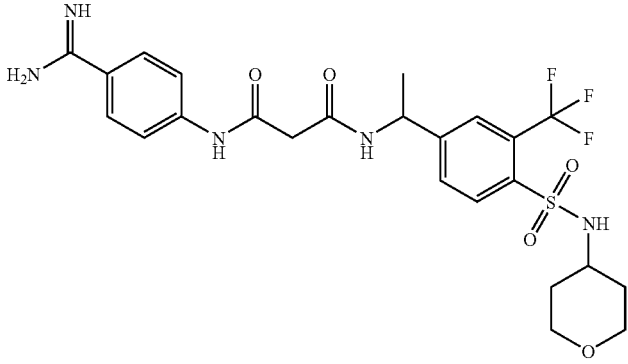 | 1.15 | 555.18 | E |

| Example No | Structural Formula | Rt (from LC/MS) | Mass (from LC/MS) | LC/MS Method |
|---|---|---|---|---|
| 110 | 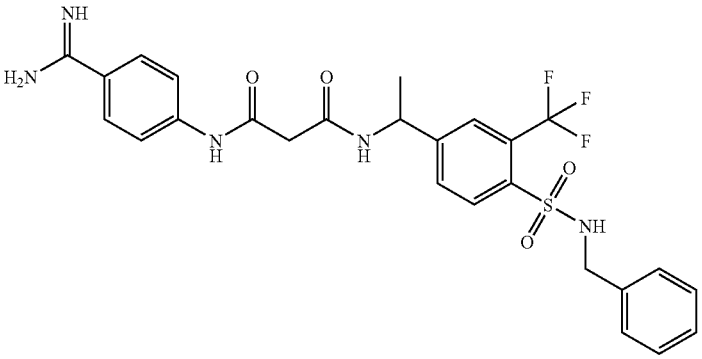 | 1.33 | 561.17 | E |
| 111 | 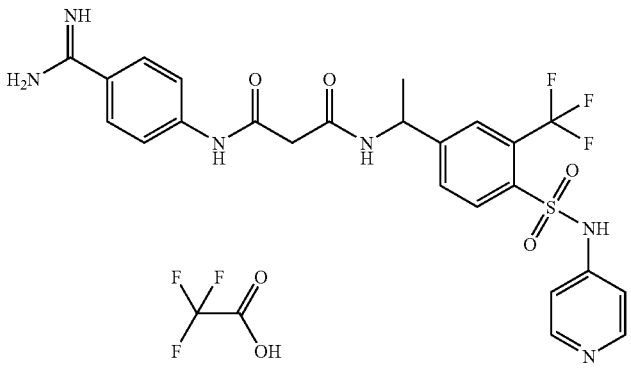 | 0.81 | 548.15 | E |
| 112 | 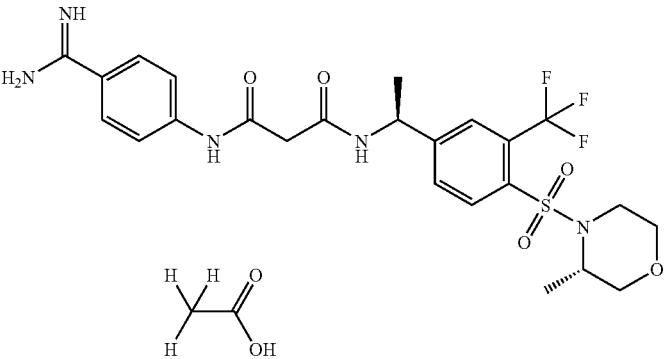 | 1.28 | 555.18 | E |

-continued
| Example No | Structural Formula | Rt (from LC/MS) | Mass (from LC/MS) | LC/MS Method |
|---|---|---|---|---|
| 113 | 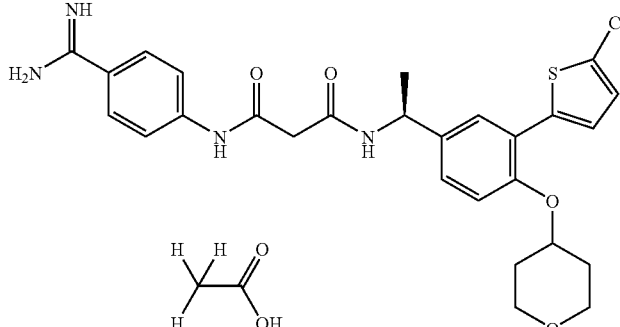 | 1.55 | 540.16 | E |
| 114 | 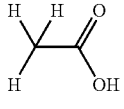 | 1.32 | 525.17 | E |
| 115 | 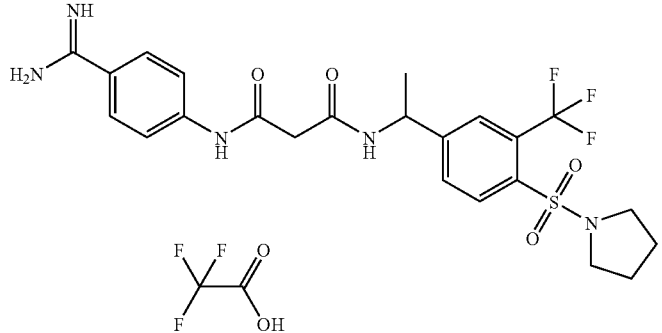 | 1.19 | 555.18 | E |
| 116 | 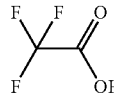 | 1.62 | 567.21 | E |

| Example No | Structural Formula | Rt (from LC/MS) | Mass (from LC/MS) | LC/MS Method |
|---|---|---|---|---|
| 117 | 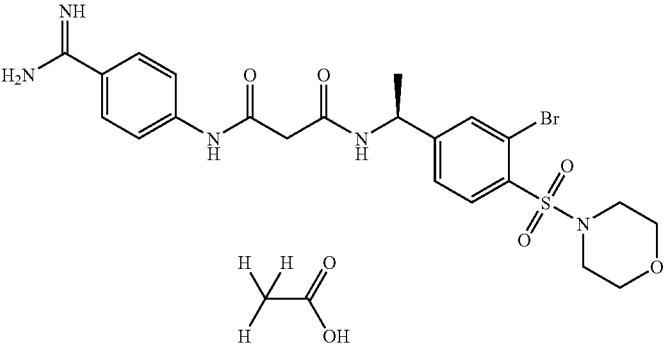 | 1.09 | 551.08 | E |
| 118 | 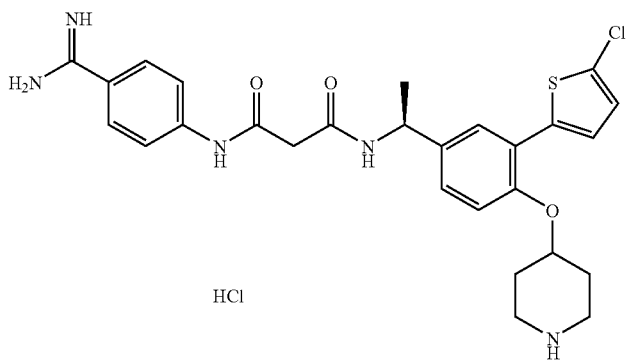 | 1.18 | 539.18 | E |
| 119 | 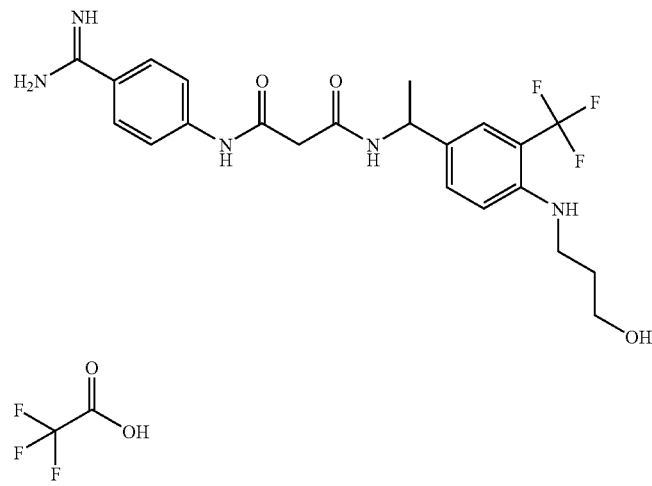 | 1.10 | 466.22 | A |
| 120 | 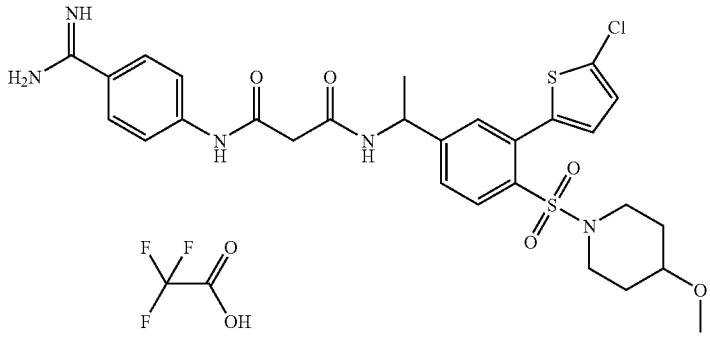 | 1.400 | 617.15 | E |

| Example No | Structural Formula | Rt (from LC/MS) | Mass (from LC/MS) | LC/MS Method |
|---|---|---|---|---|
| 121 | 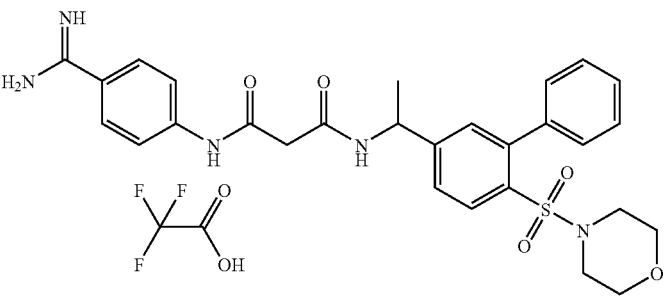 | 1.270 | 549.2 | E |
| 122 | 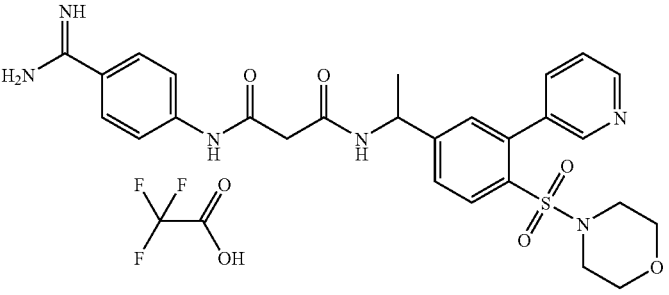 | 0.850 | 550.2 | E |
| 123 | 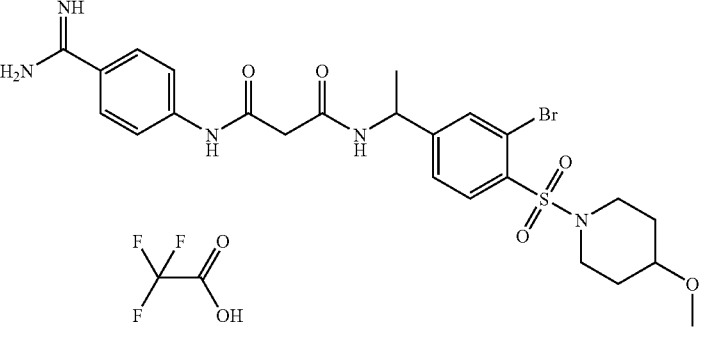 | 1.19 | 579.12 | E |
| 124 | 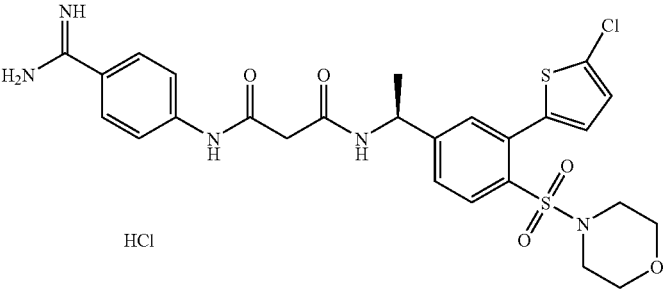 | 1.3 | 589.12 | E |

| Example No | Structural Formula | Rt (from LC/MS) | Mass (from LC/MS) | LC/MS Method |
|---|---|---|---|---|
| 125 | 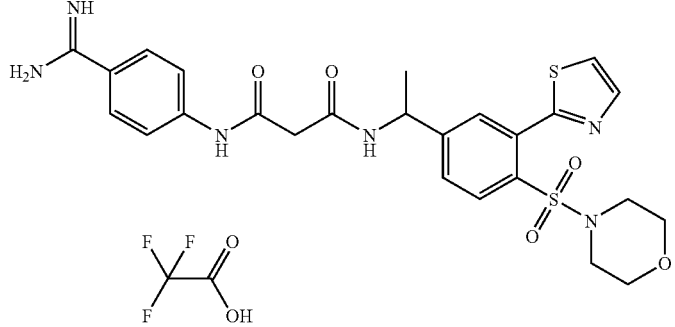 | 1.05 | 556.16 | E |
| 126 | 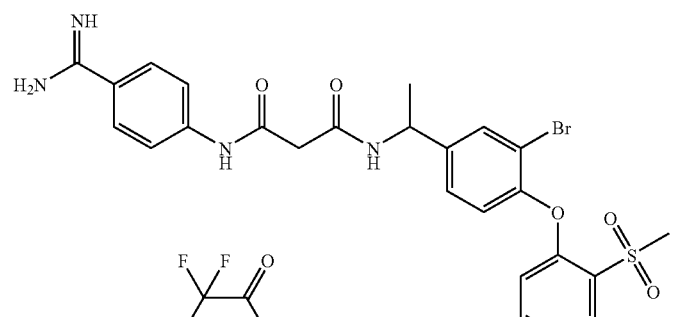 | 1.23 | 572.07 | E |
| 127 | 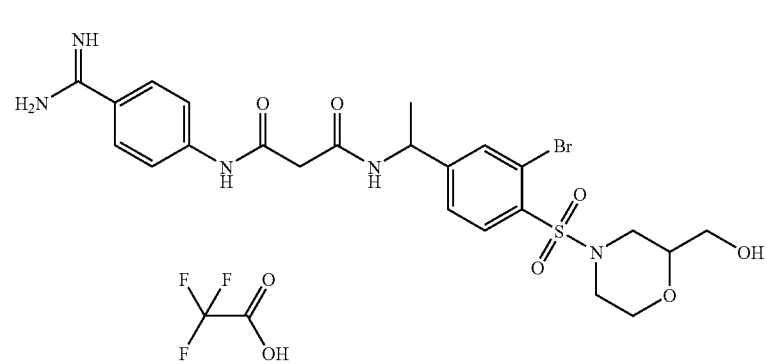 | 1.27 | 651.14 | E |
| 128 | 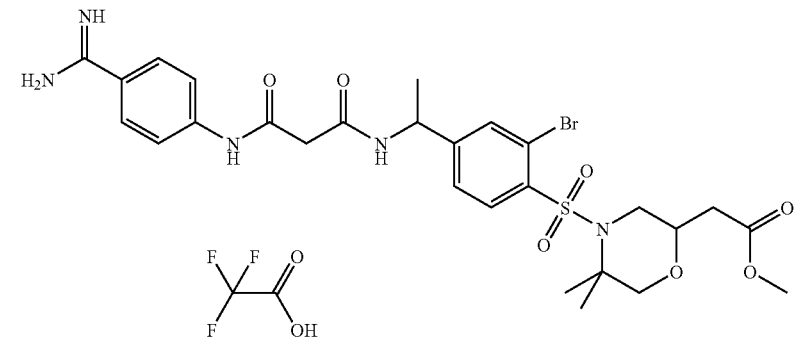 | 1.02 | 582.09 | E |

-continued
| Example No | Structural Formula | Rt (from LC/MS) | Mass (from LC/MS) | LC/MS Method |
|---|---|---|---|---|
| 129 | 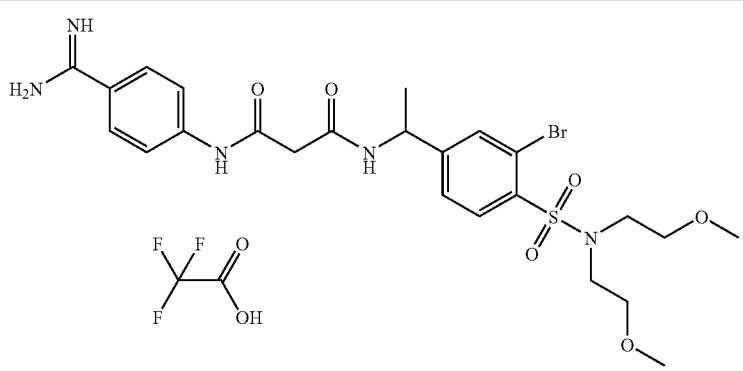 | 1.13 | 597.13 | E |
| 130 | 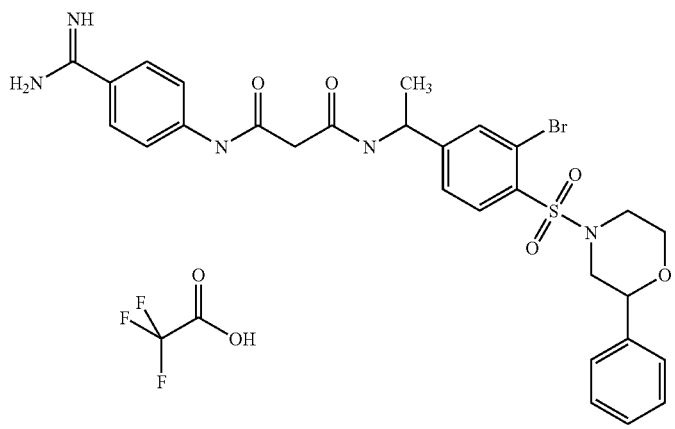 | 1.38 | 627.12 | E |
| 131 | 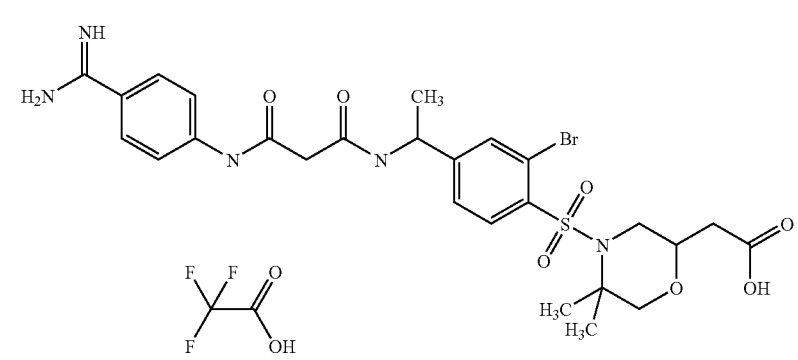 | 1.15 | 637.12 | E |
| 132 | 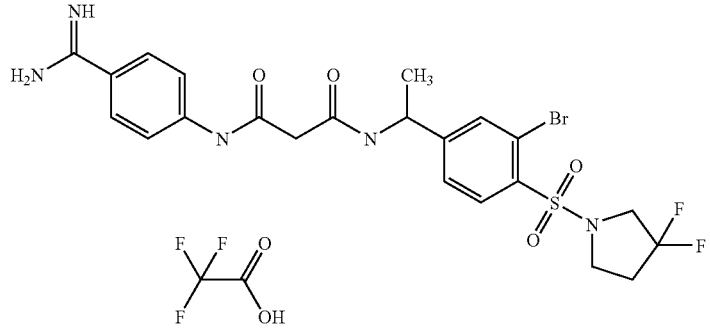 | 1.27 | 571.07 | E |

| Example No | Structural Formula | | Rt (from LC/MS) | Mass (from LC/MS) | LC/MS Method |
|---|---|---|---|---|---|
| 133 | 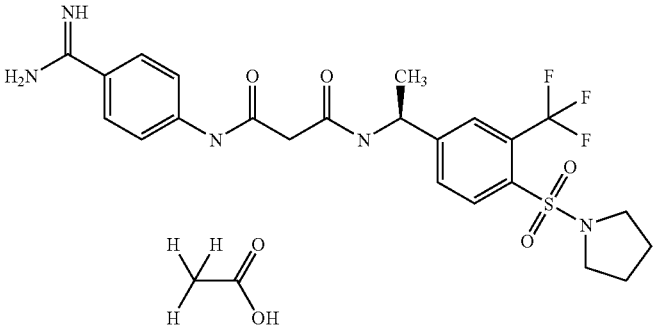 | Chiral | 1.22 | 525.17 | E |
| 134 | 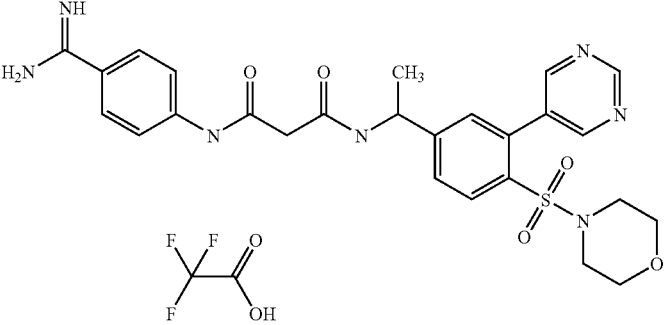 | | 1.04 | 551.20 | E |
| 135 | 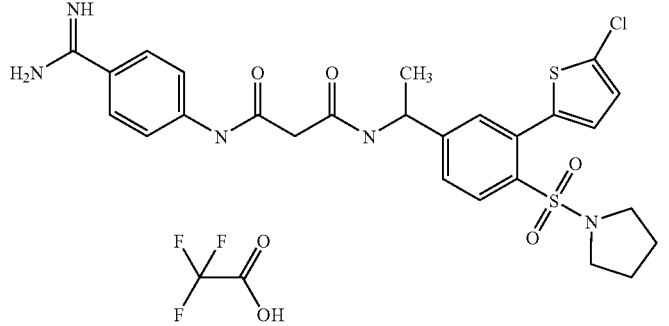 | | 1.4 | 573.13 | E |
| 136 | 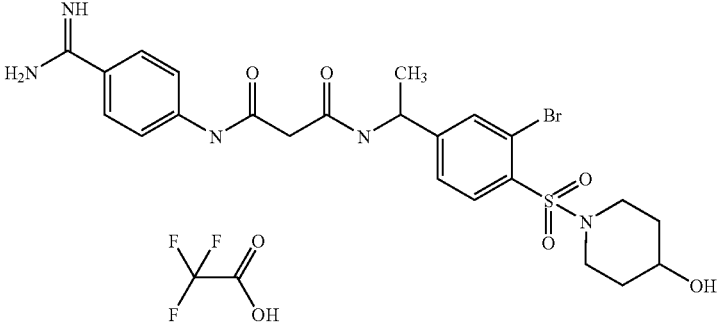 | | 1.08 | 565.10 | E |

| Example No | Structural Formula | | Rt (from LC/MS) | Mass (from LC/MS) | LC/MS Method |
|---|---|---|---|---|---|
| 137 | 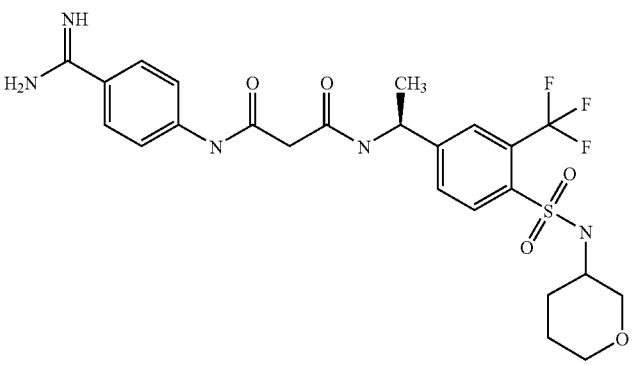 | | 1.14 | 555.18 | E |
| 138 | 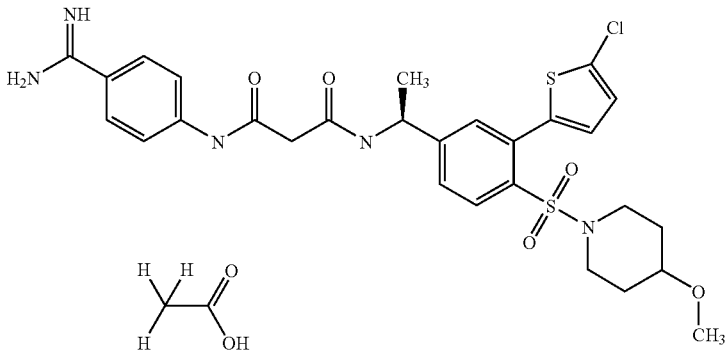 | Chiral | 1.38 | 617.15 | E |
| 139 | 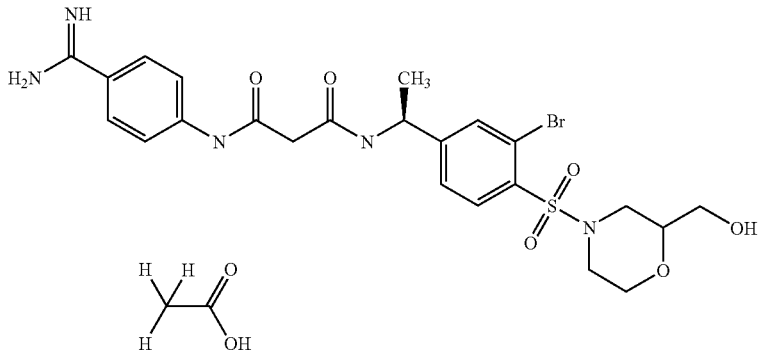 | Chiral | 1.08 | 581.09 | E |

-continued
| Example No | Structural Formula | | Rt (from LC/MS) | Mass (from LC/MS) | LC/MS Method |
|---|---|---|---|---|---|
| 140 | 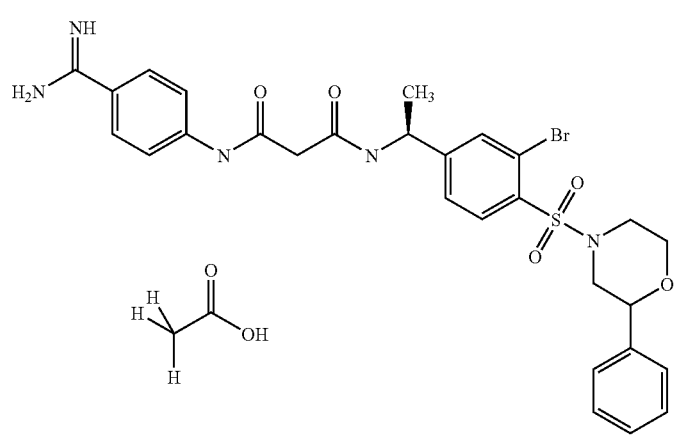 | Chiral | 1.40 | 627.12 | E |
| 141 | 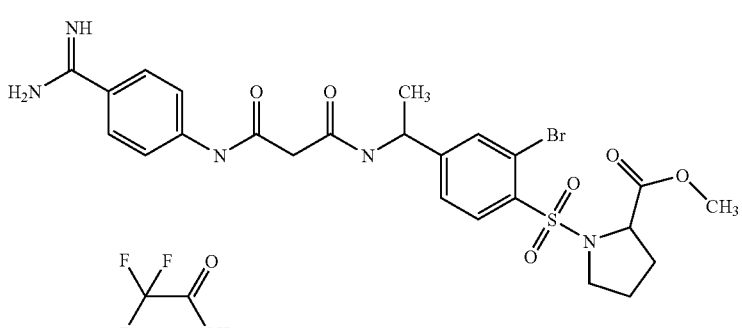 | | 1.23 | 593.09 | E |
| 142 | 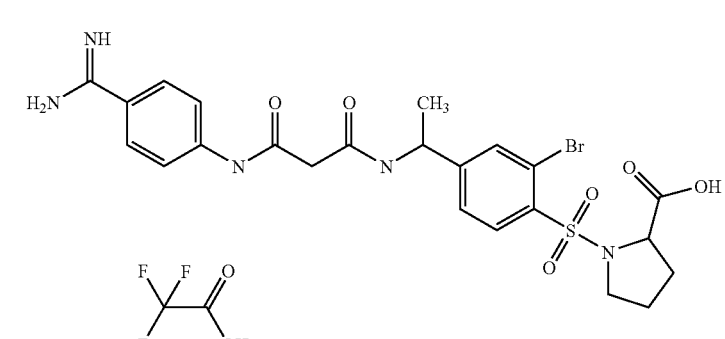 | | 1.04 | 579.08 | E |
| 143 | 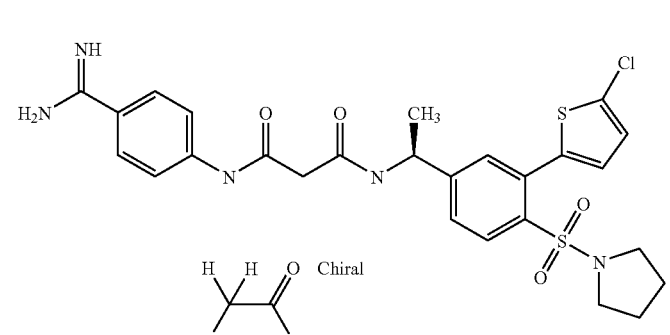 | Chiral | 1.52 | 573.13 | E |

-continued
| Example No | Structural Formula | Rt (from LC/MS) | Mass (from LC/MS) | LC/MS Method |
|---|---|---|---|---|
| 144 | 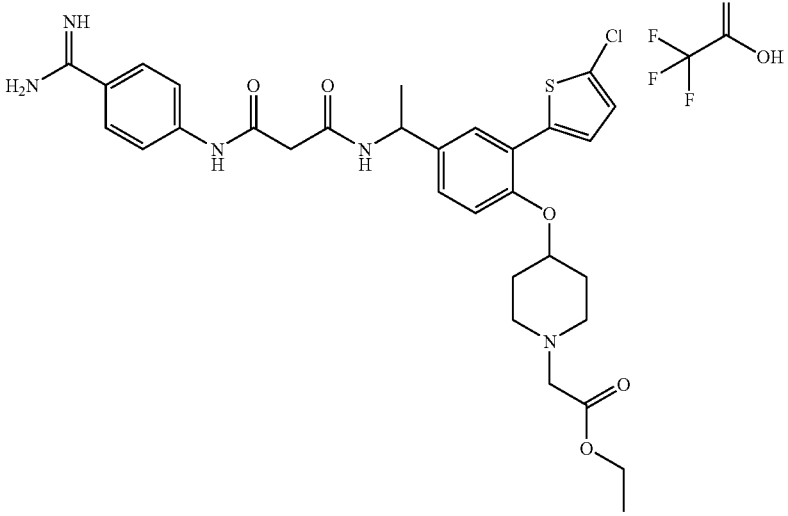 | 1.25 | 626.30 | A |
| 145 | 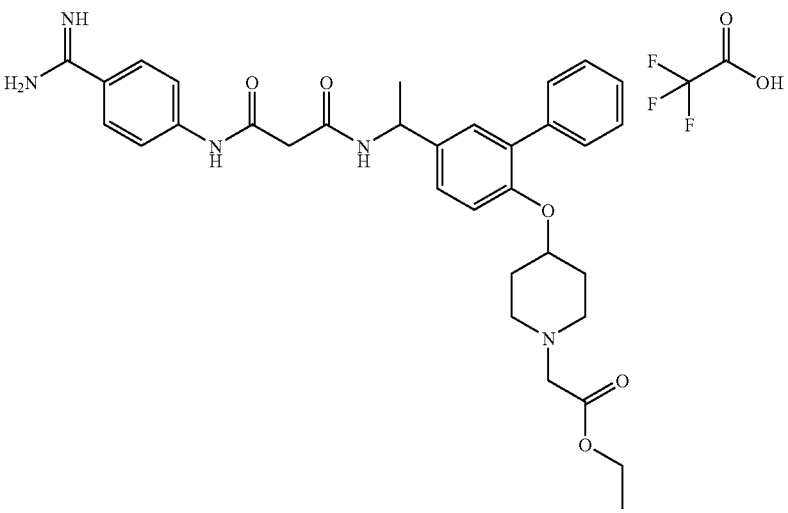 | 1.08 | 586.33 | A |
| 146 | 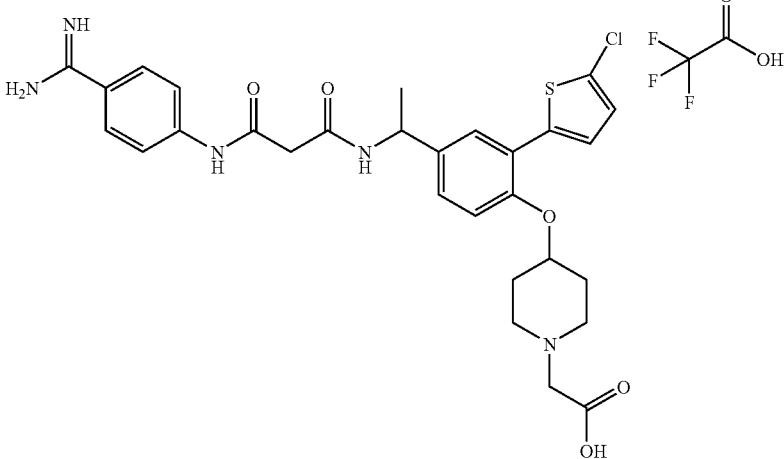 | 1.10 | 598.27 | A |

-continued
| Example No | Structural Formula | Rt (from LC/MS) | Mass (from LC/MS) | LC/MS Method |
|---|---|---|---|---|
| 147 | 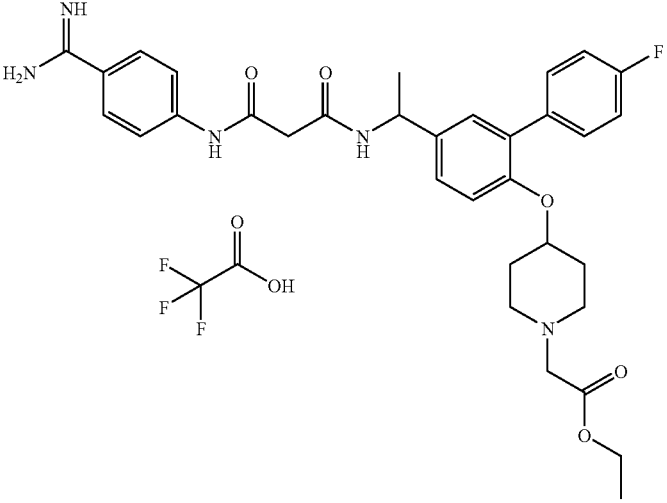 | 1.10 | 604.30 | A |
| 148 | 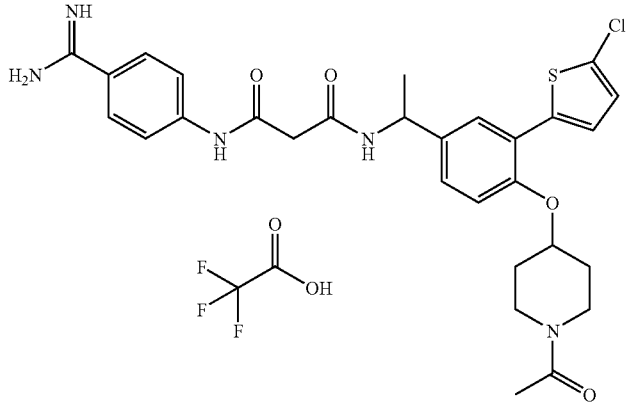 | 1.31 | 582.18 | A |
| 149 | 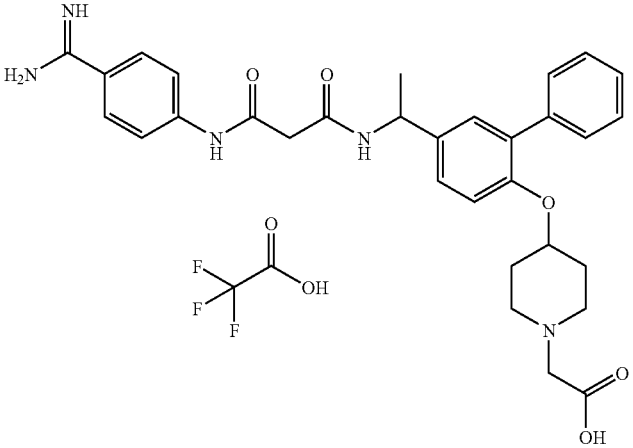 | 0.99 | 558.27 | A |

-continued
| Example No | Structural Formula | Rt (from LC/MS) | Mass (from LC/MS) | LC/MS Method |
|---|---|---|---|---|
| 150 | 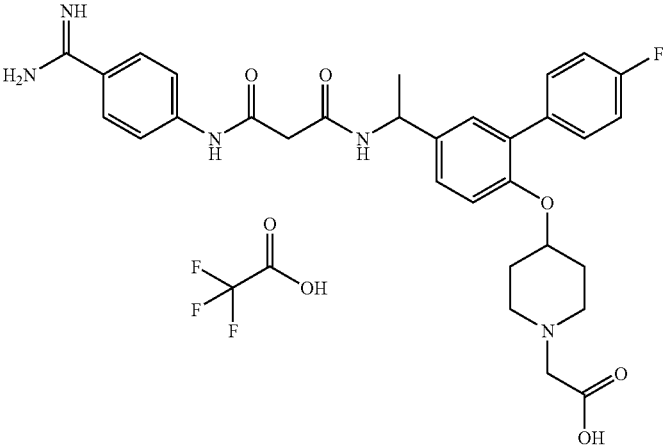 | 1.01 | 576.28 | A |
| 151 | 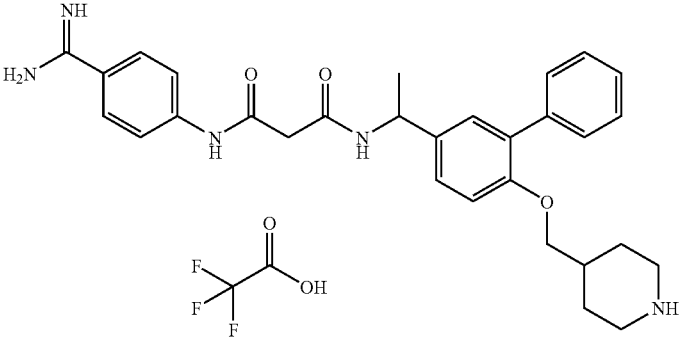 | 2.42 | 514.26 | B |
| 152 | 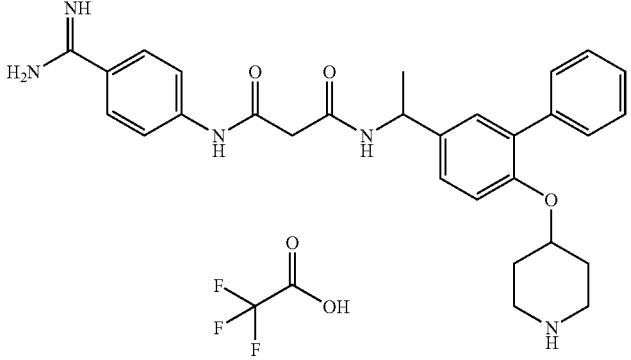 | 2.32 | 500.25 | B |
| 153 | 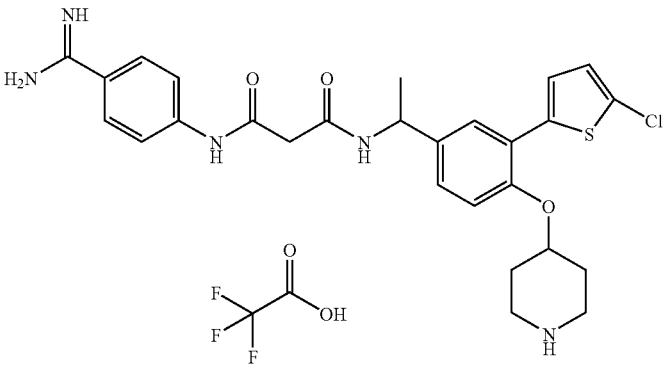 | 1.87 | 540.21 | B |

| Example No | Structural Formula | Rt (from LC/MS) | Mass (from LC/MS) | LC/MS Method |
|---|---|---|---|---|
| 154 | 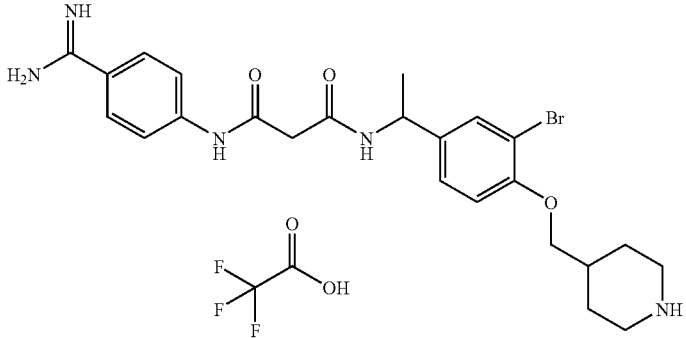 | 1.61 | 518.17 | B |
| 155 | 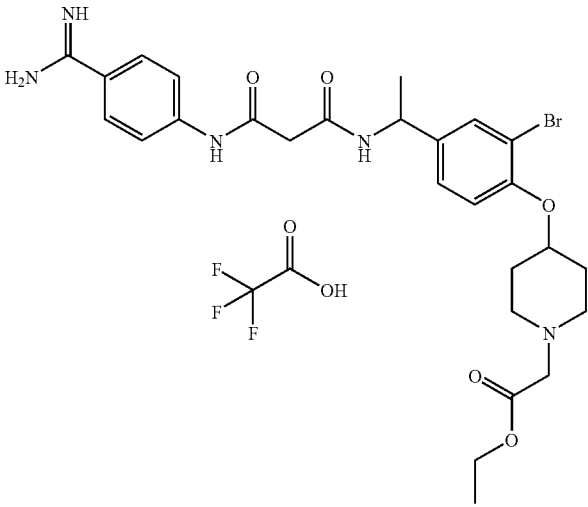 | 1.74 | 588.2 | B |
| 156 | 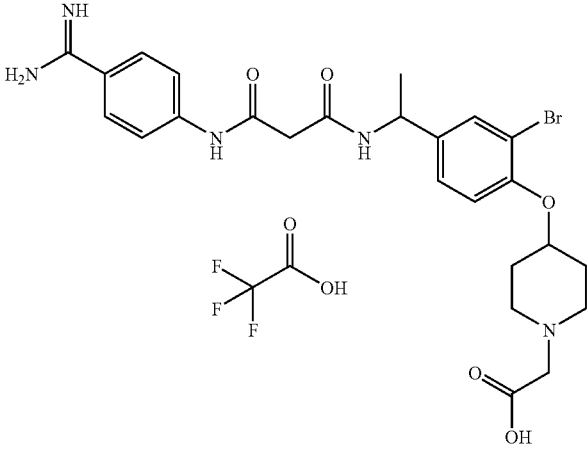 | 1.59 | 560.15 | B |

LC/MS spectra were recorded according to the following methods:

Method A: column: YMC J'shere H80 33×2.1 mm 4 μm
  solvent: ACN+0.05% TFA:H$_2$O+0.05% TFA (flow 1.3 mL/min)
  gradient: 5:95 (0 min) to 95:5 (2.5 min) to 95:5 (3.0 min)
  ionization: ESI$^+$ Method B: column: Synergi Hydro-RP 20×4.0 mm, 2 μm
  solvent: H2O+0.1% Fomic Acid:ACN+0.1% Fomic Acid
  gradient: 90:10 (0 min) to 10:90 (3 min) to 0:100 (5 min).
  MS methods: LCT system, scan range 100-1000
  ionization: ESI$^+$ Method D: column: YMC J'shere ODS H80 20×2.1 mm 4 μm
  solvent: ACN:H$_2$O+0.05% TFA (flow 1 mL/min)
  gradient: 4:96 (0 min) to 95:5 (2 min) to 95:5 (2.4 min) to 96:4 (2.45 min)
  ionization: ESI$^+$ Method E: column: YMC J'shere 33×2 mm, 4 μm
solvent: H$_2$O+0.05% TFA:ACN+0.05% TFA 95:5 (0 min) to 5:95 (2.5 min) to 95:5
MS method: LCT system, 0.33 s scan time for mass 170-1300
ionization: ESI$^+$ Method F: column: YMC J'shere 33×2 mm, 4 μm
solvent: H$_2$O+0.05% TFA:ACN+0.05% TFA 95:5 (0 min) to 5:95 (3.7 min)
MS method: MUX system 0.15 s scan time for mass 100-1500
ionization: ESI$^+$ Method L: column: (S,S) Whelk-O1, 250×4 mm,
solvent: Hep:EtOH:MeOH 1:1:1+0.1% NH4Ac
ionization: ESI$^+$ Preparative HPLC was performed according to the following method:
column: Waters Atlantis dC18 OBD 30×100 mm 5 μm
solvent: ACN:H$_2$O+0.1% TFA (flow 60 mL/min)
gradient: 10:90 (0 min) to 90:10 (10 min)

Pharmacological Testing

The ability of the compounds of the formulae I and Ia to inhibit factor VIIa or other enzymes like factor Xa, thrombin, plasmin, or trypsin can be assessed by determining the concentration of the compound of the formulae I and Ia that inhibits enzyme activity by 50%, i.e. the IC$_{50}$ value, which is related to the inhibition constant Ki. Purified enzymes are used in chromogenic assays. The concentration of inhibitor that causes a 50% decrease in the rate of substrate hydrolysis is determined by linear regression after plotting the relative rates of hydrolysis (compared to the uninhibited control) versus the log of the concentration of the compound of formulae I and Ia. For calculating the inhibition constant Ki, the IC$_{50}$ value is corrected for competition with substrate using the formula Ki=IC$_{50}$/{1+(substrate concentration/Km)} wherein Km is the Michaelis-Menten constant (Chen and Prusoff, Biochem. Pharmacol. 22 (1973), 3099-3108; I. H. Segal, Enzyme Kinetics, 1975, John Wiley & Sons, New York, 100-125; which are incorporated herein by reference).

Factor VIIa (FVIIa) Assay

The inhibitory activity (expressed as inhibition constant Ki(FVIIa)) of the compounds of formulae I and Ia towards factor VIIa/tissue factor activity was determined using a chromogenic assay essentially as described previously (J. A. Ostrem et al., Biochemistry 37 (1998) 1053-1059 which is incorporated herein by reference). Kinetic assays were conducted at 25° C. in half-area microtiter plates (Costar Corp., Cambridge, Ma.) using a kinetic plate reader (Molecular Devices Spectramax 250). A typical assay consisted of 25 μl human factor VIIa and TF (5 nM and 10 nM, respective final concentration) combined with 40 μl of inhibitor dilutions in 10% DMSO/TBS-PEG buffer (50 mM Tris, 15 mM NaCl, 5 mM CaCl$_2$, 0.05% PEG 8000, pH 8.15). Following a 15 minute preincubation period, the assay was initiated by the addition of 35 μl of the chromogenic substrate S-2288 (D-Ile-Pro-Arg-p-nitroanilide, Pharmacia Hepar Inc., 500 μM final concentration).

The following test results (inhibition constants Ki(FVIIa)) were obtained.

TABLE 2

| Example No. | K$_i$ (FVIIa) (μM) |
|---|---|
| 1. | 0.041 |
| 2. | 0.171 |

TABLE 2-continued

| Example No. | K$_i$ (FVIIa) (μM) |
|---|---|
| 3. | 0.169 |
| 10. | 0.024 |
| 24. | 0.061 |
| 26. | 0.047 |
| 28. | 0.055 |
| 44. | 0.078 |
| 50. | 0.080 |
| 51. | 0.122 |
| 52 | 0.087 |
| 61. | 0.087 |
| 67. | 0.588 |
| 74. | 0.036 |
| 75. | 0.037 |
| 76. | 0.027 |
| 77. | 0.099 |
| 112. | 0.029 |
| 113. | 0.007 |
| 117. | 0.030 |

What is claimed is:

1. A compound of formula I,

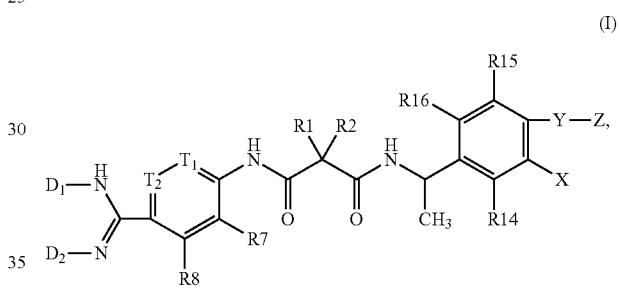

wherein

T1 and T2 independent from one another are selected from the group consisting of a carbon atom, which is substituted by R12, and a nitrogen atom, D1 and D2 independently from one another are
1) a hydrogen atom,
2) —C(O)—(C$_1$-C$_6$)-alkyl,
3) —C(O)—(C$_0$-C$_6$)-alkylene-aryl,
4) —C(O)—O—(C$_1$-C$_6$)-alkyl or
5) —C(O)—O—(C$_0$-C$_6$)-alkylene-aryl,
6) —C(O)—O—(C$_1$-C$_6$)-alkylene-O—C(O)—(C$_1$-C$_6$)-alkyl D1 is a hydrogen atom, when D2 is
1) —OH,
2) —O—C(O)—(C$_1$-C$_6$)-alkyl or
3) —O—C(O)—(C$_0$-C$_6$)-alkylene-aryl,
4) —C(O)—O—(C$_1$-C$_6$)-alkylene-O—C(O)—(C$_1$-C$_6$)-alkyl R1 and R2 independently of one another are
1) a hydrogen atom,
2) —OH or
3) —(C$_0$-C$_6$)-alkylene-T-(C$_0$-C$_6$)-alkylene-W, wherein T is an oxygen atom, a sulfur atom, —SO$_2$— or —N(R17)—, R17 is a hydrogen atom or —(C$_1$-C$_6$)-alkyl, wherein the alkyl is unsubstituted or mono-, di-, tri- or tetra-substituted independently of one another by R13, W is a hydrogen atom or aryl, wherein the aryl is unsubstituted or mono-, di-, tri- or tetra-substituted independently of one another by R13, R7, R8, R12, R14, R15 and R16 independently of one another are
1) a hydrogen atom,
2) —($C_1$-$C_6$)-alkyl,
3) —OH,
4) —O—($C_1$-$C_6$)-alkyl,
5) halogen or
6) —$NH_2$,
X is
1) halogen,
2) —($C_1$-$C_3$)-perfluoroalkyl,
3) —O—($C_1$-$C_3$)-perfluoroalkyl,
4) —S(O)$_n$—($C_1$-$C_3$)-perfluoroalkyl, wherein n is the integer 1 or 2,
5) —($C_0$-$C_4$)-alkylene-aryl, wherein aryl is unsubstituted or mono-, di-, tri- or tetra-substituted independently of one another by R13,
   wherein R13 is halogen, —($C_1$-$C_3$)-perfluoroalkyl, —($C_1$-$C_4$)-alkyl, —($C_0$-$C_6$)-alkylene-O—R6, —($C_0$-$C_6$)-alkylene-C(O)—R6, —($C_0$-$C_6$)-alkylene-C(O)—O—R6, —O—($C_1$-$C_3$)-perfluoroalkyl, —S(O)$_r$—($C_1$-$C_4$)-alkyl, wherein r is the integer 1 or 2 or —($C_0$-$C_4$)-alkylene-($C_3$-$C_7$)-cycloalkyl,
   wherein R6 is a hydrogen atom or —($C_1$-$C_6$)-alkyl,
6) —($C_0$-$C_4$)-alkylene-Het, wherein Het is a heterocycle consisting of 1, 2 or 3 rings, in which one or more of the 4 to 15 ring carbon atoms are replaced by at least 1 heteroatom selected from nitrogen, oxygen or sulfur and wherein Het is unsubstituted or mono-, di-, tri- or tetra-substituted independently of one another by R5,
wherein R5 is —($C_1$-$C_4$)-alkyl, halogen, =O, —($C_0$-$C_6$)-alkylene-O—R6, —($C_0$-$C_6$)-alkylene-C(O)—R6, —($C_0$-$C_6$)-alkylene-C(O)—O—R6, —($C_0$-$C_4$)-alkylene-($C_3$-$C_7$)-cycloalkyl, or —($C_0$-$C_4$)-alkylene-aryl, wherein aryl is unsubstituted or mono-, di-, tri- or tetra-substituted independently of one another by R13, or
7) a hydrogen atom,
Y is
1) —N(R4)—, wherein R4 is a hydrogen atom or —($C_1$-$C_6$)-alkyl,
2) —C(O)—,
3) —C(O)—N(R4)—,
4) —N(R4)—C(O)—,
5) —O—,
6) —S(O)$_n$—, wherein n is the integer zero, 1 or 2, or
7) —S(O)$_m$—N(R4)—, wherein m is the integer zero, 1 or 2,
Z is
1) —($C_0$-$C_4$)-alkylene-Het, wherein Het is unsubstituted or mono-, di-, tri- or tetra-substituted independently of one another by R5,
2) —($C_1$-$C_6$)-alkylene-C(O)—O—R6,
3) —($C_1$-$C_6$)-alkylene-O—R9,
wherein R9 is a hydrogen atom or —($C_1$-$C_6$)-alkyl,
4) —($C_1$-$C_6$)-alkylene-N(R10)-R11,
wherein R10 and R11 independently from one another are hydrogen atom, —($C_0$-$C_4$)-alkylene-C(O)—R6, —($C_0$-$C_4$)-alkylene-O—R6 or —($C_1$-$C_6$)-alkyl,
5) —($C_0$-$C_4$)-alkylene-C(O)—R6,
6) —($C_2$-$C_6$)-alkynyl,
7) —($C_1$-$C_3$)-perfluoroalkyl,
8) —($C_0$-$C_4$)-alkylene-($C_3$-$C_7$)-cycloalkyl-R5,
9) —($C_1$-$C_4$)-alkylene-aryl, wherein aryl is unsubstituted or mono-, di-, tri- or tetra-substituted independently of one another by R13,
10) phenyl, wherein phenyl is mono-, di-, tri- or tetra-substituted independently of one another by —($C_0$-$C_4$)-alkylene-($C_3$-$C_7$)-cycloalkyl, =O, —($C_0$-$C_6$)-alkylene-C(O)—O—R6, —($C_1$-$C_6$)-alkylene-O—R6 or —S(O)$_s$-($C_1$-$C_3$)-alkyl, wherein s is the integer zero, 1 or 2,
11) —S(O)$_r$—($C_1$-$C_3$)-alkyl, wherein r is the integer zero, 1 or 2, provided Y is —N(R4)—, or
12) —($C_1$-$C_3$)-perfluoroalkyl, or
Y and Z together are a hydrogen atom and X is
1) —($C_1$-$C_3$)-alkyl-CN,
2) —($C_1$-$C_3$)-perfluoroalkyl,
3) —O—($C_1$-$C_3$)—,
4) —S(O)$_m$—($C_1$-$C_3$)-perfluoroalkyl, wherein m is the integer 1 or 2,
5) —($C_0$-$C_4$)-alkylene-Het, wherein Het is mono-, di-, tri- or tetra-substituted independently of one another by aryl, or
6) phenyl substituted by —N(R3)—S(O)$_p$, wherein R3 is a hydrogen atom or —($C_1$-$C_6$)-alkyl and p is the integer 1 or 2,
in all its stereoisomeric forms and mixtures thereof in any ratio, and its physiologically tolerable salts.

2. A compound as claimed in claim 1 of formula Ia, (Ia)

wherein
D1 and D2 are each a hydrogen atom,
X is
1) halogen, selected from fluorine, chlorine, bromine or iodine,
2) —($C_1$-$C_3$)-perfluoroalkyl,
3) —O—($C_1$-$C_3$)-perfluoroalkyl,
4) —S(O)$_n$—($C_1$-$C_3$)-perfluoroalkyl, wherein n is the integer 1 or 2,
5) —($C_0$-$C_4$)-alkylene-aryl, wherein aryl is selected from phenyl, naphthyl, biphenylyl, anthryl or fluorenyl unsubstituted or mono-, di-, tri- or tetra-substituted independently of one another by R13,
   wherein R13 is halogen, —($C_1$-$C_3$)-perfluoroalkyl, —($C_1$-$C_4$)-alkyl, —($C_0$-$C_6$)-alkylene-O—R6, —($C_0$-$C_6$)-alkylene-C(O)—R6, —($C_0$-$C_6$)-alkylene-C(O)—O—R6, —O—($C_1$-$C_3$)-perfluoroalkyl, —S(O)$_r$—($C_1$-$C_4$)-alkyl, wherein r is the integer 1 or 2 or —($C_0$-$C_4$)-alkylene-($C_3$-$C_7$)-cycloalkyl,
   wherein R6 is a hydrogen atom or —($C_1$-$C_6$)-alkyl,
6) —($C_0$-$C_4$)-alkylene-Het, wherein Het is selected from acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-arbazolyl, carbolinyl, chromanyl, chromenyl, cinnolinyl, decahydrochinolinyl, 4,5-dihydrooxazolyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl or xanthenyl, and wherein Het is unsubstituted or mono-, di-, tri- or tetra-substituted independently of one another by R5, wherein R5 is $-(C_1-C_4)$-alkyl, halogen, $=O$, $-(C_0-C_6)$-alkylene-O—R6, $-(C_0-C_6)$-alkylene-C(O)—R6, $-(C_0-C_6)$-alkylene-C(O)—O—R6, $-(C_0-C_4)$-alkylene-$(C_3-C_7)$-cycloalkyl, or $-(C_0-C_4)$-alkylene-aryl, wherein aryl is unsubstituted or mono-, di-, tri- or tetra-substituted independently of one another by R13, or 7) a hydrogen atom, Y is 1) —N(R4)—, wherein R4 is a hydrogen atom or $-(C_1-C_6)$-alkyl,
2) —C(O)—,
3) —C(O)—N(R4)—,
4) —N(R4)—C(O)—,
5) —O—,
6) —S(O)$_n$—, wherein n is the integer zero, 1 or 2, or
7) —S(O)$_m$—N(R4)—, wherein m is the integer zero, 1 or 2, Z is 1) $-(C_0-C_4)$-alkylene-Het, wherein Het is unsubstituted or mono-, di-, tri- or tetra-substituted independently of one another by R5,
2) $-(C_1-C_6)$-alkylene-C(O)—O—R6,
3) $-(C_1-C_6)$-alkylene-O—R9,
wherein R9 is a hydrogen atom or $-(C_1-C_6)$-alkyl,
4) $-(C_1-C_6)$-alkylene-N(R10)-R11, wherein R10 and R11 independently from one another are hydrogen atom, $-(C_0-C_4)$-alkylene-C(O)—R6, $-(C_0-C_4)$-alkylene-O—R6 or $-(C_1-C_6)$-alkyl,
5) $-(C_0-C_4)$-alkylene-C(O)—R6,
6) $-(C_2-C_6)$-alkynyl,
7) $-(C_1-C_3)$-perfluoroalkyl,
8) $-(C_0-C_4)$-alkylene-$(C_3-C_7)$-cycloalkyl-R5,
9) $-(C_1-C_4)$-alkylene-aryl, wherein aryl is as defined above and is unsubstituted or mono-, di-, tri- or tetra-substituted independently of one another by R13,
10) phenyl, wherein phenyl is mono-, di-, tri- or tetra-substituted independently of one another by $-(C_0-C_4)$-alkylene-$(C_3-C_7)$-cycloalkyl, $=O$, $-(C_0-C_6)$-alkylene-C(O)—O—R6, $-(C_1-C_6)$-alkylene-O—R6 or $-S(O)_s$—$(C_1-C_3)$-alkyl, wherein s is the integer zero, 1 or 2,
11) $-S(O)_r$—$(C_1-C_3)$-alkyl, wherein r is the integer zero, 1 or 2, provided Y is —N(R4)—, or
12) $-(C_1-C_3)$-perfluoroalkyl, or Y and Z together are hydrogen atom and X is 1) $-(C_1-C_3)$-alkyl-CN,
2) $-(C_1-C_3)$-perfluoroalkyl,
3) —O—$(C_1-C_3)$-perfluoroalkyl,
4) —S(O)$_m$—$(C_1-C_3)$-perfluoroalkyl, wherein m is the integer 1 or 2,
5) $-(C_0-C_4)$-alkylene-Het, wherein Het is mono-, di-, tri- or tetra-substituted independently of one another by aryl, wherein aryl is selected out of the group phenyl, naphthyl, biphenylyl, anthryl or fluorenyl, or
6) phenyl substituted by —N(R3)—S(O)$_p$, wherein R3 is a hydrogen atom or $-(C_1-C_6)$-alkyl and p is the integer 1 or 2, in all its stereoisomeric forms and mixtures thereof in any ratio, and its physiologically tolerable salts.

3. A compound as claimed in claim 2, wherein

D1 and D2 are each a hydrogen atom,

X is 1) chlorine, bromine or fluorine,
2) $-(C_1-C_3)$-perfluoroalkyl,
3) —O—$(C_1-C_3)$-perfluoroalkyl,
4) —S(O)$_n$—$(C_1-C_3)$-perfluoroalkyl, wherein n is the integer 1 or 2,
5) $-(C_0-C_4)$-alkylene-phenyl, wherein phenyl is unsubstituted or mono-, di-, tri- or tetra-substituted independently of one another by R13,
wherein R13 is chlorine, bromine, fluorine, $-(C_1-C_3)$-perfluoroalkyl, $-(C_1-C_4)$-alkyl, $-(C_0-C_6)$-alkylene-O—R6, $-(C_0-C_6)$-alkylene-C(O)—R6, $-(C_0-C_6)$-alkylene-C(O)—O—R6, —O—$(C_1-C_3)$-perfluoroalkyl, —S(O)$_r$—$(C_1-C_4)$-alkyl, wherein r is the integer 1 or 2; or $-(C_0-C_4)$-alkylene-$(C_3-C_7)$-cycloalkyl,
wherein R6 is a hydrogen atom or $-(C_1-C_4)$-alkyl,
6) $-(C_0-C_4)$-alkylene-Het, wherein Het is selected from acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4] oxathiazinyl, 6H-1,5,2-dithiazinyl, dihydrofuro[2,3b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl or xanthenyl, and wherein Het is unsubstituted or mono-, di-, tri- or tetra-substituted independently of one another by R5, wherein R5 is —$(C_1-C_4)$-alkyl, chlorine, bromine, fluorine, =O, —$(C_0-C_6)$-alkylene-O—R6, —$(C_0-C_6)$-alkylene-C(O)—R6, —$(C_0-C_6)$-alkylene-C(O)—O—R6, —$(C_0-C_4)$-alkylene-$(C_3-C_7)$-cycloalkyl, or —$(C_0-C_4)$-alkylene-phenyl, wherein phenyl is unsubstituted or mono-, di-, tri- or tetra-substituted independently of one another by R13, Y is
1) —N(R4)—, wherein R4 is hydrogen atom or —$(C_1-C_4)$-alkyl,
2) —C(O)—,
3) —C(O)—N(R4)—,
4) —N(R4)—C(O)—,
5) —O—,
6) —$S(O)_n$—, wherein n is the integer zero, 1 or 2, or
7) —$S(O)_m$—N(R4)—, wherein m is the integer zero, 1 or 2, Z is
1) —$(C_0-C_4)$-alkylene-Het, wherein Het is as defined above and wherein Het is unsubstituted or mono-, di-, tri- or tetra-substituted independently of one another by R5,
2) —$(C_1-C_6)$-alkylene-C(O)—O—R6,
3) —$(C_1-C_6)$-alkylene-O—R9,
wherein R9 is hydrogen atom or —$(C_1-C_6)$-alkyl,
4) —$(C_1-C_6)$-alkylene-N(R10)-R11, wherein R10 and R11 independently from one another are hydrogen atom, —$(C_0-C_4)$-alkylene-C(O)—R6, —$(C_0-C_4)$-alkylene-O—R6 or —$(C_1-C_6)$-alkyl,
5) —$(C_0-C_4)$-alkylene-C(O)—R6,
6) —$(C_0-C_4)$-alkylene-$(C_3-C_7)$-cycloalkyl-R5, or
7) —$(C_0-C_4)$-alkylene-aryl, wherein aryl is selected out of the group phenyl, naphthyl, biphenylyl, anthryl or fluorenyl and wherein aryl is mono-, di-, tri- or tetra-substituted independently of one another by R13,
wherein R13 is —$(C_0-C_4)$-alkylene-$(C_3-C_7)$-cycloalkyl, =O, —$(C_1-C_6)$-alkylene-C(O)—O—R6 or —$(C_1-C_4)$-alkylene-O—R6,
in all its stereoisomeric forms and mixtures thereof in any ratio, and its physiologically tolerable salts.

4. A compound as claimed in claim 2, wherein
D1 and D2 are each a hydrogen atom,
X is
1) chlorine, bromine or fluorine,
2) —$CF_3$,
3) —O—$CF_3$,
4) —O—$CH_2$—$CHF_2$,
5) —O—$CH_2$—$CH_2$—$CH_2F$,
6) —O—$CH_2$—$CF_3$,
7) phenyl, wherein the phenyl is unsubstituted or mono-ordi-substituted independently of one another by R13, wherein R13 is chlorine, bromine, fluorine, —O—$(C_1-C_3)$-perfluoroalkyl, —O—R6, —C(O)—O—R6 or —$S(O)_2$—$(C_1-C_2)$-alkyl
wherein R6 is hydrogen atom or —$(C_1-C_4)$-alkyl, or
8) $Het_1$, wherein $Het_1$ is selected out of the group pyridine, pyrimidine, thiazole or thienyl, and wherein $Het_1$ is unsubstituted or substituted by chlorine, bromine, fluorine or —C(O)—O—R6, Y is
1) —N(R4)—, wherein R4 is hydrogen atom or methyl,
2) —C(O)—,
3) —C(O)—N(R4)—,
4) —NH—C(O)—,
5) —O—,
6) —S(O)—,
7) —$S(O)_2$—, or
8) —$S(O)_2$—N(R4)—, Z is
1) —$(C_0-C_3)$-alkylene-Het, wherein Het is selected from 1,3-dioxolanyl, furanyl, morpholinyl, [1,4]-oxazepanyl, oxetanyl, piperazinyl, piperidinyl, pyrazinyl, pyridyl, pyrimidinyl, pyrrolidinyl, tetrahydrofuranyl, tetrahydropyranyl, thiazolyl orthienyl, and wherein Het is unsubstituted or mono-, di- or tri-substituted independently of one another by R5,
wherein R5 is a hydrogen atom, —$(C_1-C_2)$-alkyl, -cyclopropyl, =O, phenyl, fluorine, —$(C_0-C_2)$-alkylene-C(O)—O—R6, —O—R6, C(O)—R6, or —$(C_1-C_2)$-alkylene-O—R6,
wherein R6 a is hydrogen atom or —$(C_1-C_4)$-alkyl,
2) —$(C_1-C_6)$-alkylene-C(O)—O—R6,
3) —$(C_1-C_6)$-alkylene-O—R9,
wherein R9 is a hydrogen atom or —$(C_1-C_3)$-alkyl,
4) —$(C_1-C_4)$-alkylene-N(R10)-R11,
wherein R10 and R11 independently of one another are a hydrogen atom, —$(C_0-C_4)$-alkylene-O—R6 or —$(C_1-C_2)$-alkyl,
5) —$(C_0-C_2)$-alkylene-C(O)—R6, or
6) —$(C_0-C_2)$-alkylene-cyclohexyl-R5,
in all its stereoisomeric forms and mixtures thereof in any ratio, and its physiologically tolerable salts.

5. A compound as claimed in claim 2, wherein
D1 and D2 are each a hydrogen atom,
X is
1) chlorine, bromine or fluorine,
2) —$CF_3$,
3) —O—$CF_3$,
4) —O—$CH_2$—$CHF_2$,
5) —O—$CH_2$—$CH_2$—$CH_2F$,
6) —O—$CH_2$—$CF_3$,
7) phenyl, wherein the phenyl is unsubstituted or mono-ordi-substituted independently of one another by R13, wherein R13 is chlorine, bromine, fluorine, —O—$(C_1-C_3)$-perfluoroalkyl, —O—R6, —C(O)—O—R6 or —$S(O)_2$—$(C_1-C_2)$-alkyl
wherein R6 is hydrogen atom or —$(C_1-C_4)$-alkyl, or
8) $Het_1$, wherein $Het_1$ is selected out of the group pyridine, pyrimidine, thiazole or thienyl, and wherein $Het_1$ is unsubstituted or substituted by chlorine, bromine, fluorine or —C(O)—O—R6,
Y is —O—, Z is 1) —($C_0$-$C_3$)-alkylene-Het, wherein Het is selected from 1,3-dioxolanyl, furanyl, morpholinyl, [1,4]-oxazepanyl, oxetanyl, piperazinyl, piperidinyl, pyrazinyl, pyridyl, pyrimidinyl, pyrrolidinyl, tetrahydrofuranyl, tetrahydropyranyl, thiazolyl orthienyl, and wherein Het is unsubstituted or mono-, di- or tri-substituted independently of one another by R5, wherein R5 is hydrogen atom, —($C_1$-$C_2$)-alkyl, -cyclopropyl, =O, phenyl, fluorine, —($C_0$-$C_2$)-alkylene-C(O)—O—R6, —O—R6, C(O)—R6, or —($C_1$-$C_2$)-alkylene-O—R6, wherein R6 is hydrogen atom or —($C_1$-$C_4$)-alkyl,
2) —($C_1$-$C_6$)-alkylene-C(O)—O—R6,
3) —($C_1$-$C_6$)-alkylene-O—R9,
wherein R9 is a hydrogen atom or —($C_1$-$C_3$)-alkyl,
4) —($C_1$-$C_4$)-alkylene-N(R10)-R11,
wherein R10 and R11 independently of one another are a hydrogen atom, —($C_0$-$C_4$)-alkylene-O—R6 or —($C_1$-$C_2$)-alkyl,
5) —($C_0$-$C_2$)-alkylene-C(O)—R6, or
6) —($C_0$-$C_2$)-alkylene-cyclohexyl-R5,
in all its stereoisomeric forms and mixtures thereof in any ratio, and its physiologically tolerable salts.

6. A compound as claimed in claim 2, wherein
D1 and D2 are each a hydrogen atom,
X is
1) chlorine, bromine or fluorine,
2) —$CF_3$,
3) —O—$CF_3$,
4) —O—$CH_2$—$CHF_2$,
5) —O—$CH_2$—$CH_2$—$CH_2F$,
6) —O—$CH_2$—$CF_3$,
7) phenyl, wherein the phenyl is unsubstituted or mono- or di-substituted independently of one another by R13, wherein R13 is chlorine, bromine, fluorine, —O—($C_1$-$C_3$)-perfluoroalkyl, —O—R6, —C(O)—O—R6 or —S(O)$_2$—($C_1$-$C_2$)-alkyl
wherein R6 is a hydrogen atom or —($C_1$-$C_4$)-alkyl, or
8) Het$_1$, wherein Het$_1$ is selected from pyridine, pyrimidine, thiazole or thienyl, and wherein Het$_1$ is unsubstituted or substituted by chlorine, bromine, fluorine or —C(O)—O—R6,
Y is —S(O)$_2$—,
Z is
1) —($C_0$-$C_3$)-alkylene-Het, wherein Het is selected out of the group 1,3-dioxolanyl, furanyl, morpholinyl, [1,4]-oxazepanyl, oxetanyl, piperazinyl, piperidinyl, pyrazinyl, pyridyl, pyrimidinyl, pyrrolidinyl, tetrahydrofuranyl, tetrahydropyranyl, thiazolyl, thienyl and wherein Het is unsubstituted or mono-, di- or tri-substituted independently of one another by R5, wherein R5 is hydrogen atom, —($C_1$-$C_2$)-alkyl, -cyclopropyl, =O, phenyl, fluorine, —($C_0$-$C_2$)-alkylene-C(O)—O—R6, —O—R6, C(O)—R6, or —($C_1$-$C_2$)-alkylene-O—R6,
wherein R6 is hydrogen atom or —($C_1$-$C_4$)-alkyl,
2) —($C_1$-$C_6$)-alkylene-C(O)—O—R6,
3) —($C_1$-$C_6$)-alkylene-O—R9,
wherein R9 is hydrogen atom or —($C_1$-$C_3$)-alkyl,
4) —($C_1$-$C_4$)-alkylene-N(R10)-R11,
wherein R10 and R11 independently from one another are hydrogen atom, —($C_0$-$C_4$)-alkylene-O—R6 or —($C_1$-$C_2$)-alkyl,
5) —($C_0$-$C_2$)-alkylene-C(O)—R6, or
6) —($C_0$-$C_2$)-alkylene-cyclohexyl-R5,
in all its stereoisomeric forms and mixtures thereof in any ratio, and its physiologically tolerable salts.

7. A compound as claimed in claim 2, wherein
D1 and D2 are each hydrogen atom,
Y and Z together are hydrogen atom and
X is
1) —($C_1$-$C_3$)-alkyl-CN,
2) —$CF_2$—$CF_3$,
3) —O—$CF_2$—$CHF_2$,
4) —O—$CH_2$—$CF_3$,
5) —S(O)—$CF_3$,
6) —S(O)$_2$—$CF_3$,
7) imidazolyl, substituted by phenyl, or
8) phenyl substituted by —NH—S(O)$_2$-methyl,
in all its stereoisomeric forms and mixtures thereof in any ratio, and its physiologically tolerable salts.

8. A compound as claimed in claim 2, wherein
D1 and D2 are each a hydrogen atom,
X is a hydrogen atom,
Y is
1) —NH—,
2) —NH—C(O)—or
3) —S(O)$_2$—, and
Z is
1) Het, wherein Het is selected from morpholinyl or piperidinyl, or
2) —S(O)$_2$-methyl, provided Y is —NH—,
in all its stereoisomeric forms and mixtures thereof in any ratio, and its physiologically tolerable salts.

9. A process for the preparation of a compound of formula I as claimed in claim 1, comprising linking the building blocks of the formulae III, IV, and V

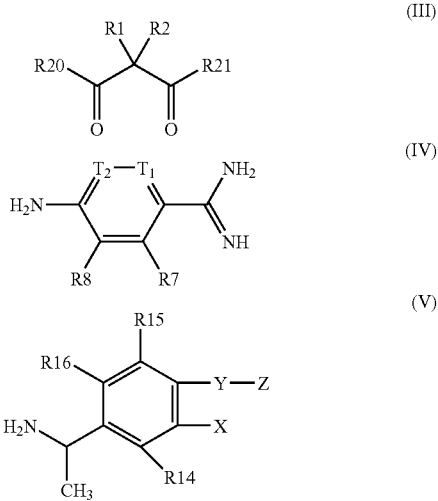

wherein R20 and R21 are independently of each other —OH, F, Cl or together with the carbonyl group form an ester, or an activated ester, or a mixed anhydride, or any other activated species resulting from the reaction of the carboxylic acid with coupling reagents, and R1, R2, R7, R8, R14, R15, R16, T1, T2, X, Y and Z are as defined in claim 1,
by means of forming an amide bond between the carboxylic acid derivative depicted in formula III and the $NH_2$-group depicted in formula IV and an amide bond or ester bond between the carboxylic acid derivative depicted in formula III and the $NH_2$-group depicted in formula V.

10. A pharmaceutical composition comprising at least one compound as claimed in claim 1 and a pharmaceutically acceptable carrier.

* * * * *